(12) United States Patent  (10) Patent No.: US 8,507,426 B2
Min et al.  (45) Date of Patent: *Aug. 13, 2013

(54) PEPTIDES AND RELATED MOLECULES THAT BIND TO TALL-1

(75) Inventors: Hosung Min, Newbury Park, CA (US); Hailing Hsu, Moorpark, CA (US); Fei Xiong, Thousand Oaks, CA (US)

(73) Assignee: Amgen, Inc., Thousand Oaks, CA (US)

( * ) Notice: Subject to any disclaimer, the term of this patent is extended or adjusted under 35 U.S.C. 154(b) by 304 days.

This patent is subject to a terminal disclaimer.

(21) Appl. No.: 12/788,137

(22) Filed: May 26, 2010

(65) Prior Publication Data

US 2010/0240590 A1  Sep. 23, 2010

Related U.S. Application Data

(60) Continuation of application No. 11/272,521, filed on Nov. 10, 2005, now Pat. No. 7,737,111, which is a division of application No. 10/145,206, filed on May 13, 2002, now Pat. No. 7,259,137.

(60) Provisional application No. 60/290,196, filed on May 11, 2001.

(51) Int. Cl.
*A61K 38/10* (2006.01)

(52) U.S. Cl.
USPC ........... 514/1.1; 514/21.3; 514/21.2; 530/324

(58) Field of Classification Search
None
See application file for complete search history.

(56) References Cited

U.S. PATENT DOCUMENTS

| | | | |
|---|---|---|---|
| 4,496,689 A | 1/1985 | Mitra | |
| 5,223,409 A | 6/1993 | Ladner et al. | |
| 5,338,665 A | 8/1994 | Schatz et al. | |
| 5,432,018 A | 7/1995 | Dower et al. | |
| 5,498,530 A | 3/1996 | Schatz et al. | |
| 5,514,582 A | 5/1996 | Capon et al. | |
| 5,733,731 A | 3/1998 | Schatz et al. | |
| 5,922,545 A | 7/1999 | Mattheakis et al. | |
| 5,969,102 A | 10/1999 | Bram et al. | |
| 6,323,323 B1 | 11/2001 | Sledziewski et al. | |
| 6,331,415 B1 | 12/2001 | Cabilly et al. | |
| 6,403,770 B1 | 6/2002 | Yu et al. | |
| 6,869,605 B2 | 3/2005 | Browning et al. | |
| 7,118,872 B2 | 10/2006 | Beltzer et al. | |
| 7,317,089 B2 | 1/2008 | Kikly | |
| 7,728,109 B2 | 6/2010 | Kikly | |
| 7,737,111 B2 * | 6/2010 | Min et al. | 424/178.1 |
| 2006/0084608 A1 | 4/2006 | Beltzer et al. | |
| 2009/0110676 A1 | 4/2009 | Mackay et al. | |
| 2010/0144058 A1 | 6/2010 | Beltzer et al. | |

FOREIGN PATENT DOCUMENTS

| EP | 0784680 | 7/1997 |
|---|---|---|
| EP | 0526452 | 2/2001 |
| EP | 0939804 | 8/2005 |
| WO | WO 96/40987 | 12/1996 |
| WO | WO 98/15833 | 4/1998 |
| WO | WO 98/18921 | 5/1998 |
| WO | WO 98/27114 | 6/1998 |
| WO | WO 0869180 | 10/1998 |
| WO | WO 98/55620 | 12/1998 |
| WO | WO 98/55621 | 12/1998 |
| WO | WO 99/11791 | 3/1999 |
| WO | WO 99/12964 | 3/1999 |
| WO | WO 99/25044 | 5/1999 |
| WO | WO 99/35170 | 7/1999 |
| WO | WO 99/62951 | 12/1999 |
| WO | WO 00/24782 | 5/2000 |
| WO | WO 00/40716 | 7/2000 |
| WO | WO 00/47740 | 8/2000 |
| WO | WO 00/67034 | 11/2000 |
| WO | WO 00/68378 | 11/2000 |

(Continued)

OTHER PUBLICATIONS

Becker, K. G., et al., "Rapid Isolation and Characterization of 118 Novel C2H2-Type Zinc Finger cDNAs Expressed in Human Brain," *Hum. Mol. Genet.* 4:685-691 (1995).

(Continued)

*Primary Examiner* — Anish Gupta
(74) *Attorney, Agent, or Firm* — Perkins Coie LLP; Patrick D. Morris

(57) ABSTRACT

The present invention concerns therapeutic agents that modulate the activity of TALL-1. In accordance with the present invention, modulators of TALL-1 may comprise an amino acid sequence $Dz^2Lz^4$ wherein $z^2$ is an amino acid residue and $z^4$ is threonyl or isoleucyl. Exemplary molecules comprise a sequence of the formulae $$a^1a^2a^3CDa^6La^8a^9a^{10}Ca^{12}a^{13}a^{14}, \quad \text{(SEQ ID NO: 100)}$$

$$b^1b^2b^3Cb^5b^6Db^8Lb^{10}b^{11}b^{12}b^{13}b^{14}Cb^{16}b^{17}b^{18} \quad \text{(SEQ ID NO: 104)}$$

$$c^1c^2c^3Cc^5DC^7Lc^9c^{10}c^{11}c^{12}c^{13}c^{14}Cc^{16}c^{17}c^{18} \quad \text{(SEQ ID NO: 105)}$$

$$d^1d^2d^3Cd^5d^6d^7WDd^{10}Ld^{13}d^{14}d^{15}Ld^{16}d^{17}d^{18} \quad \text{(SEQ ID NO: 106)}$$

$$e^1e^2e^3Ce^5e^6e^7De^9Le^{11}Ke^{13}Ce^{15}e^{16}e^{17}e^{18} \quad \text{(SEQ ID NO: 107)}$$

$$f^1f^2f^3Kf^5Df^7Lf^9f^{10}Qf^{12}f^{13}f^{14} \quad \text{(SEQ ID NO: 109)}$$

wherein the substituents are as defined in the specification. The invention further comprises compositions of matter of the formula $$(X^1)_a\text{-}V^1\text{-}(X^2)_b$$

wherein V1 is a vehicle that is covalently attached to one or more of the above TALL-1 modulating compositions of matter. The vehicle and the TALL-1 modulating composition of matter may be linked through the N- or C-terminus of the TALL-1 modulating portion. The preferred vehicle is an Fc domain, and the preferred Fc domain is an IgG Fc domain.

7 Claims, 39 Drawing Sheets

(56) References Cited

FOREIGN PATENT DOCUMENTS

| | | |
|---|---|---|
| WO | WO 01/02440 | 1/2001 |
| WO | WO 01/85782 | 11/2001 |
| WO | WO 02/16411 | 2/2002 |
| WO | WO 02/16412 | 2/2002 |

OTHER PUBLICATIONS

Cheema et al., "Increased B Lymphocyte Stimulator (BlyS™) Protein in HIV-Patients: Correlation wit Anti-Cardiolipin (aCL) and Anti-Phospholipid (aPL) Autoantibodies," abstract (2002).

Cheema et al., "Elevated Serum B Lymphocyte Stimulator Levels in Patients with Systemic Immune-Based Rheumatic Diseases," *Arthritis & Rheumatism* 44:1313-1319 (2001).

Chirinos-Rojas, C. L., et al., "A Phage-Displayed Mimotope Inhibits Tumour Necrosis Factor-Induced Cytotoxicity More Effectively Than the Free Mimotope," *Immunology* 96:109-113 (1999).

Cwirla et al., "Peptide Agoinist of the Thrombopoietin Receptor as Potent as the Natural Cytokine," *Science* 276:1696-1699 (1997).

Devlin et al., "Random Peptide Libraries: A Source of Specific Protein Binding Molecules," *Science* 249:404-406 (1990).

Gross et al., "TACI and BCMA are Receptors for a TNF Homologue Implicated in B-Cell Autoimmune Disease," *Nature* 404:995-999 (2000).

Gruss et al., "Tumor Necrosis Factor Ligand Superfamily: Involvement in the Pathology of Malignant Lymphomas," *Blood* 85:3378-3404 (1995).

Hatzoglou et al., "TNF Receptor Family Member BCMA (B Cell Maturation) Associates with TNF Receptor-Associated Factor (TRAF) 1, TRAF2, and TRAF3 and Activates NF-κB, Elk-1, c-Jun N-Terminal Kinase, and p38 Mitogen-Activated Protein Kinase," *J. of Immunology* 165:1322-1330 (2000).

Khare et al., "Severe B Cell Hyperplasia and Autoimmune Disease in TALL-1 Transgenic Mice," *PNAS* 97:3370-3375 (2000).

Lowman et al., "Bacteriophage Display and Discovery of Peptide Leads for Drug Development," *Ann. Rev. Biophys. Biomol. Struct.* 26:401-424 (1997).

Marsters et al., "Interaction of the TNF Homologues BlyS and APRIL with the TNF Receptor Homologues BCMA and TACI," *Current Biology* 10:785-788 (2000).

Mukhopadhyay et al., "Identifcation and Characterization of a Novel Cytokine, THANK, a TNF Homologue that Activates Apoptosis, Nuclear Factor-κB, and c-June $NH_2$ Terminal Kinase," *J. Biol. Chem.* 274:15978-15981 (1999).

Oren et al., "Structural Basis of BlyS Receptor Recognition," *Nature Structural Biology* 9:288-292 (2002).

Roberts & Szostak, "RNA-Peptide Fusions for the In Vitro Selection of Peptides and Proteins," *PNAS USA* 94:12297-12302 (1997).

Samoylova et al., "Phage probes for malignant glial cells," *Mol. Cancer Ther.* 2:1129-1137 (2003).

Scott et al., "Searching for Peptide Ligands with an Epitope Library," *Science* 249:386-390 (1990).

Sekut et al., "Characterization of a Human Monoclonal Antibody that Antagonizes B-Lymphocyte Stimulator Bioactivities," abstract (2002).

Shu et al., "B Cell Maturation Protein is a Receptor for the Tumor Necrosis Factor Family Member TALL-1," *PNAS* 97:9156-9161 (2000).

Shu et al., "TALL-1 is a Novel Member of the TNF Family that is Down-Regulated by Mitogens," *J. Leukocyte Biol.* 65:680-683 (1999).

Smith et al., "The TNF Receptor Superfamily of Cellular and Viral Proteins: Activation, Costimulation, and Death," *Cell* 76:959-962 (1994).

Takasaki et al., "Structure-Based Design and Characterization of Exocyclic Peptidomimetics that Inhibit TNFα Binding to its Receptor," *Nature Biotech.* 15:1266-1270 (1997).

Tan et al., "Local Production of B Lymphocyte Stimulator (BlyS™) Protein in Human Arthritic Joints," abstract (2002).

Thompson et al., "BAFF Binds to the Tumor Necrosis Factor Receptor-Like Molecule B Cell Maturation Antigen and is Important for Maintaining the Peripheral B Cell Population," *J. Exp. Med.* 192:129-135 (2000).

Ware, "APRIL and BAFF Connect Autoimmunity and Cancer," *J. Exp. Med.* 192:F35-F37 (2000).

Ware, "Decoy Receptors Thwart B Cells," *Nature* 404:949-950 (2000).

Wells & Lowman, "Rapid Evolution of Peptide and Protein Binding Properties In Vitro," *Curr. Opin. Biotechnol*, 3:355-362 (1992).

Xia et al., "TACI is a TRAF-Interacting Receptor for TALL-1, a Tumor Necrosis Factor Family Member Involved in B Cell Regulation," *J. Exp. Med.* 192:137-143 (2000).

Yu et al., "ARPIL and TALL-1 and Receptors BCMA and TACI: System for Regulating Humoral Immunity," *Nature Immunology* 1:252-256 (2000).

Zhang et al., "Cutting Edge: A Role for B Lymphocyte Stimulator in Systemic Lupus Erythematosus," *J. Immunology* 166:6-10 (2001).

\* cited by examiner

FIG. 1
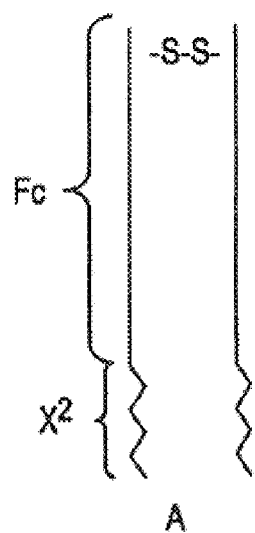
A
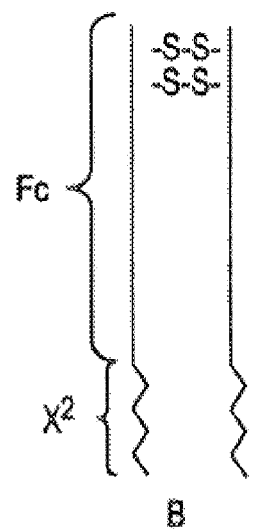
B
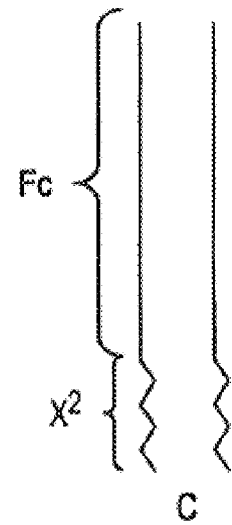
C
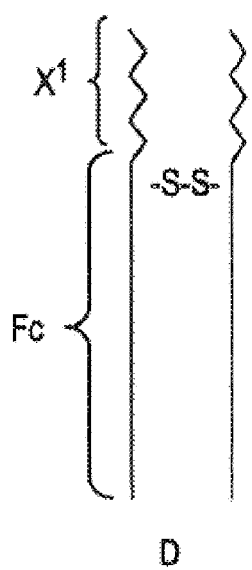
D
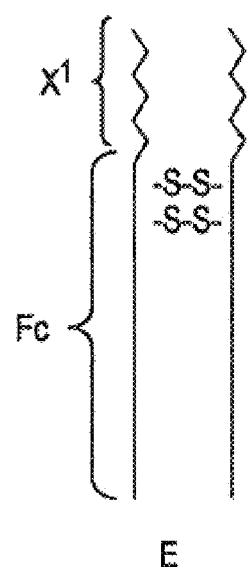
E
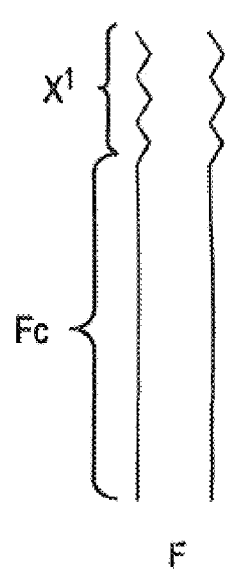
F

FIG. 2
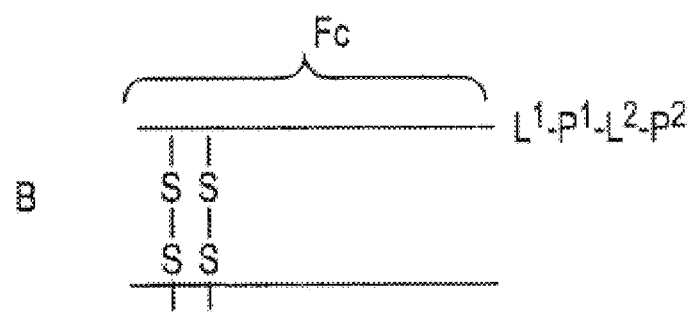
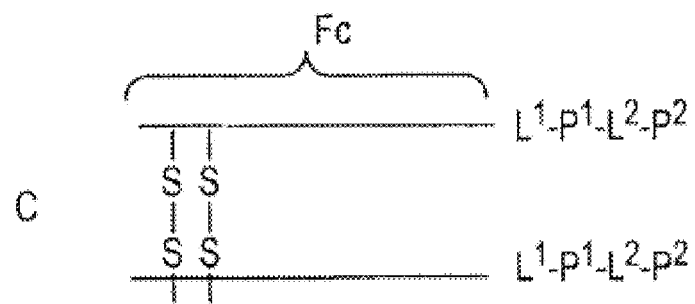

FIG. 3A

```
    ATGGACAAAACTCACACATGTCCACCTTGTCCAGCTCCGGAACTCCTGGGGACCGTCA   60
1   ---:---:---+---:---:---+---:---:---+---:---:---+---:---:---+
    TACCTGTTTTGAGTGTGTACAGGTGGAACAGGTCGAGGCCTTGAGGACCCCCTGGCAGT

M  D  K  T  H  T  C  P  P  C  P  A  P  E  L  L  G  G  P  S     -

GTCTTCCTCTTCCCCCCAAAACCCAAGGACACCCTCATGATCTCCCGGACCCCTGAGGTC  120
61  ---:---:---+---:---:---+---:---:---+---:---:---+---:---:---+
    CAGAAGGAGAAGGGGGGTTTTGGGTTCCTGTGGGAGTACTAGAGGGCCTGGGGACTCCAG

V  F  L  F  P  P  K  P  K  D  T  L  M  I  S  R  T  P  E  V     -

ACATGCGTGGTGGTGGACGTGAGCCACGAAGACCCTGAGGTCAAGTTCAACTGGTACGTG  180
121 ---:---:---+---:---:---+---:---:---+---:---:---+---:---:---+
    TGTACGCACCACCACCTGCACTCGGTGCTTCTGGGACTCCAGTTCAAGTTGACCATGCAC

T  C  V  V  V  D  V  S  H  E  D  P  E  V  K  F  N  W  Y  V     -

GACGGCGTGGAGGTGCATAATGCCAAGACAAAGCCGCGGGAGGAGCAGTACAACAGCACG  240
181 ---:---:---+---:---:---+---:---:---+---:---:---+---:---:---+
    CTGCCGCACCTCCACGTATTACGGTTCTGTTTCGGCGCCCTCCTCGTCATGTTGTCGTGC

D  G  V  E  V  H  N  A  K  T  K  P  R  E  E  Q  Y  N  S  T     -

TACCGTGTGGTGTCAGCTGTCCTCACCGTCCTGCACCAGGACTGGCTGAATGGCAAGGAGTAC  300
241 ---:---:---+---:---:---+---:---:---+---:---:---+---:---:---+
    ATGGCACACCAGTCGACAGGAGTGGCAGGACGTGGTCCTGACCGACTTACCGTTCCTCATG

Y  R  V  V  S  V  L  T  V  L  H  Q  D  W  L  N  G  K  E  Y     -

AAGTGCAAGGTCTCCAACAAAGCCCTCCCAGCCCCCATCGAGAAAACCATCTCCAAAGCC  360
301 ---:---:---+---:---:---+---:---:---+---:---:---+---:---:---+
    TTCACGTTCCAGAGGTTGTTTCGGGAGGGTCGGGGTAGCTCTTTTGGTAGAGGTTTCGG

```
361  AAGGGCAGCCCCGAGAACCACAGGTGTACACCCCTGCCCCCATCCCGGGATGAGCTGACC    420
     ----+----+----+----+----+----+----+----+----+----+----+----+
     TTTCCCGTCGGGGCTCTTGGTGTCCACATGTGGGACGGGGGTAGGGCCCTACTCGACTGG

K   G   Q   P   R   E   P   Q   V   Y   T   L   P   P   S   R   D   E   L   T

421  AAGAACCAGGTCAGCCTGACCTGCCTGGTCAAAGGCTTCTATCCCAGCGACATCGCCGTG    480
     ----+----+----+----+----+----+----+----+----+----+----+----+
     TTCTTGGTCCAGTCGGACTGGACGGACCAGTTTCCGAAGATAGGGTCGCTGTAGCGGCAC

K   N   Q   V   S   L   T   C   L   V   K   G   F   Y   P   S   D   I   A   V

481  GAGTGGGAGAGCAATGGGCAGCCGGAGAACAACTACAAGACCACGCCTCCCGTGCTGGAC    540
     ----+----+----+----+----+----+----+----+----+----+----+----+
     CTCACCCTCTCGTTACCCGTCGGCCTCTTGTTGATGTTCTGGTGCGGAGGGCACGACCTG

E   W   E   S   N   G   Q   P   E   N   N   Y   K   T   T   P   P   V   L   D

541  TCCGACGGCTCCTTCTTCCTCTACAGCAAGCTCACCGTGGACAAGAGCAGGTGGCAGCAG    600
     ----+----+----+----+----+----+----+----+----+----+----+----+
     AGGCTGCCGAGGAAGAAGGAGATGTCGTTCGAGTGGCACCTGTTCTCGTCCACCGTCGTC

S   D   G   S   F   F   L   Y   S   K   L   T   V   D   K   S   R   W   Q   Q

601  GGGAACGTCTTCTCATGCTCCGTGATGCATGAGGCTCTGCACAACCACTACACGCAGAAG    660
     ----+----+----+----+----+----+----+----+----+----+----+----+
     CCCTTGCAGAAGAGTACGAGGCACTACGTACTCCGAGACGTGTTGGTGATGTGCGTCTTC

G   N   V   F   S   C   S   V   M   H   E   A   L   H   N   H   Y   T   Q   K

661  AGCCTCTCCCTGTCTCCGGGTAAA    684
     ----+----+----+----+----
     TCGGAGAGGGACAGAGGCCCATTT

3) AGP3-8-4-a

```
         NdeI
         TATGGTTCCGTTCTGTGACCTGCTGACTAAACACTGTTTCGAAGCTGGTGGAGGCGGT
 1    ---+------------+---------+---------+---------+---------+  60
         ACCAAGGCAAGACACTGGACGACTGATTTGTGACAAAGCTTCGACCACCTCCGCCA

M  V  P  F  C  D  L  L  T  K  H  C  F  E  A  G  G  G  G  -

SalI
        GGGG
 61    -----  69
        CCCCAGCT

G  V  D  -
```

4) AGP3-12-4-a

November 6, 2000 12:53

```
         NdeI
         TATGGGTTCTCGTTGTAAATACAAATGGGACGTTCTGACTAAACAGTGTTTCCACCAC
 1    ---+------------+---------+---------+---------+---------+  60
         ACCCAAGAGCAACATTTATGTTTACCCTGCAAGACTGATTTGTCACAAGGTGGTG

M  G  S  R  C  K  Y  K  W  D  V  L  T  K  Q  C  F  H  H  -

SalI
         GGTGGAGGCGGTGGGG
 61    ---+-------------+--  81
         CCACCTCCGCCACCCCAGCT

5) AGP3-12-3-a
NdeI
```
   TATGCTGCCGGGTTGTAAATGGACCTGCTGATCAAACAGTGGGTTTGTGACCCGCTG
1  ----------+---------+---------+---------+---------+---------+  60
   ACGACGGCCCAACATTTACCCTGGACGACTAGTTTGTCACCCAAACACTGGGCGAC

M  L  P  G  C  K  W  D  L  L  I  K  Q  W  V  C  D  P  L  -
```
SalI
```
   GGTGGAGGCGGTGGGG
61 ----------+------  81
   CCACCTCCGCCACCCCAGCT

G  G  G  G  V  D  -
```

6) AGP3-12-5-a
NdeI
```
   TATGTCTGCTGACTGTTACTTCGACATCCTGACTAAATCTGACGTTTGTACTTCTTCT
1  ----------+---------+---------+---------+---------+---------+  60
   ACAGACGACTGACAATGAAGCTGTAGGACTGATTTAGACTGCAAACATGAAGAAGA

M  S  A  D  C  Y  F  D  I  L  T  K  S  D  V  C  T  S  S  -
```
SalI
```
   GGTGGAGGCGGTGGGG
61 ----------+------  81
   CCACCTCCGCCACCCCAGCT

7) AGP3-12-8-a

```
     NdeI
     ┌─────
     TATGTCTGACGACTGTATGTACGACCAGCTGACTCGTATGTTCATCGTGTTCTAACCTG    60
  1  ------+---------+---------+---------+---------+---------+-
     ACAGACTGCTGACATACATGCTGGTCGACTGAGCATACAAGTAGACAAGATTGGAC
         M   S   D   D   C   M   Y   D   Q   L   T   R   M   F   I   C   S   N   L   -

GGTGGAGGCGGTGGGG
 61  ------+--------    81
     CCACCTCCGCCACCCCAGCT
                      SalI
         G   G   G   G   V   D   -
```

8) AGP3-12-9-a

```
     NdeI
     ┌─────
     TATGGACCTGAACTGTAAATACGACGAACTGACTTACAAAGAATGGTGTCAGTTCAAC    60
  1  ------+---------+---------+---------+---------+---------+-
     ACCTGGACTTGACATTTATGCTGCTTGACTGAATGTTTCTTACCACAGTCAAGTTG
         M   D   L   N   C   K   Y   D   E   L   T   Y   K   E   W   C   Q   F   N   -

GGTGGAGGCGGTGGGG
 61  ------+--------    81
     CCACCTCCGCCACCCCAGCT
                      SalI
         G   G   G   G   V   D   -
```

FIG. 4E

9) AGP3-12-10-a
   NdeI
   TATGTTCCACGACTGTAAATACGACCTGCTGACTCGTCAGATGGTTTGTCACGGTCTG
1  ------+---------+---------+---------+---------+---------+  60
   ACAAGGTGCTGACATTTATGCTGGACGACTGAGCAGTCTACCAAACAGTGCCAGAC a   M  F  H  D  C  K  Y  D  L  L  T  R  Q  M  V  C  H  G  L  -

SalI
   GGTGGAGGCGGTGGGG
61 ------+-------+- 81
   CCACCTCCGCCACCCCAGCT a   G  G  G  G  V  D  -

10) AGP3-12-11-a
    NdeI
    TATGCGTAACCACTGTTTCTGGGACCACCTGCTGAAACAGGACATCTGTCCGTCTCCG
1   ------+---------+---------+---------+---------+---------+  60
    ACGCATTGGTGACAAAGACCCTGGTGGACGACTTTGTCCTGTAGACAGGCAGAGGC a   M  R  N  H  C  F  W  D  H  L  L  K  Q  D  I  C  P  S  P  -

SalI
   GGTGGAGGCGGTGGGG
61 ------+-------+- 81
   CCACCTCCGCCACCCCAGCT a   G  G  G  G  V  D  -

FIG. 4F

11) AGP3-12-14-a

```
         NdeI
    TATGGCTAACCAGTGTTGGTGGGACTCTCTGCTGAAAAAAACGTTTGTGAATTCTTC   60
1   ---------+---------+---------+---------+---------+---------+
    ACCGATTGGTCACAACCACCCTGAGAGACGACTTTTTTTGCAAACACTTAAGAAG
      M  A  N  Q  W  W  D  S  L  L  K  K  N  V  C  E  F  F   -
                                    SalI
    GGTGGAGGCGGTGGGG   81
61  ---------+------
    CCACCTCCGCCACCCCCAGCT
      G  G  G  G  V  D   -
```

12) AGP3 Consensus

```
         NdeI
    TATGTTCCACGACTGCAAATGGGACCTGCTGACCAAACAGTGGGTTTGCCACGGTCTG   60
1   ---------+---------+---------+---------+---------+---------+
    gtATACAAGGTGCTGACGTTTACCCTGGACGACTGGTTTGTCACCCAAACGGTGCCAGAC
      M  F  H  D  C  K  W  D  L  L  T  K  Q  W  V  C  H  G  L   -
                                    SalI
    GGTGGAGGCGGTGGGG   81
61  ---------+------
    CCACCTCCGCCACCCCCAGCT
      G  G  G  G  V  D   -
```

FIG. 5A

```
                                    P
                                    f
                                    l
                                    1
                                    1
                                    0
                                    8
                                    I
       GATCAGCAGTCCCCGGAACATCGTAGCTGACGCCTTCGCGTTGCTCAGTTGTCCAACCCC
  1    ---------+---------+---------+---------+---------+---------+  60
       CTAGTCGTCAGGGGCCTTGTAGCATCGACTGCGGAAGCGCAACGAGTCAACAGGTTGGGG

GGAAACGGGAAAAAGCAAGTTTTCCCCGCTCCCGGCGTTTCAATAACTGAAAACCATACT
  61   ---------+---------+---------+---------+---------+---------+  120
       CCTTTGCCCTTTTTCGTTCAAAAGGGGCGAGGGCCGCAAAGTTATTGACTTTTGGTATGA

B
                                                               g
                                                               l
                                                               I
                                                               I
       ATTTCACAGTTTAAATCACATTAAACGACAGTAATCCCCGTTGATTTGTGCGCCAACACA
  121  ---------+---------+---------+---------+---------+---------+  180
       TAAAGTGTCAAATTTAGTGTAATTTGCTGTCATTAGGGGCAACTAAACACGCGGTTGTGT

-35                      -10
                             -------                  ------
       ------ Promoter (PcopB) -------------------------------->
       GATCTTCGTCACAATTCTCAAGTCGCTGATTTCAAAAAACTGTAGTATCCTCTGCGAAAC
  181  ---------+---------+---------+---------+---------+---------+  240
       CTAGAAGCAGTGTTAAGAGTTCAGCGACTAAAGTTTTTTGACATCATAGGAGACGCTTTG
                                                         |-->
                                                         mRNA start GATCCCTGTTTGAGTATTGAGGAGGCGAGATGTCGCAGACAGAAAATGCAGTGACTTCCT
  241  ---------+---------+---------+---------+---------+---------+  300
       CTAGGGACAAACTCATAACTCCTCCGCTCTACAGCGTCTGTCTTTTACGTCACTGAAGGA
  c                                    M  S  Q  T  E  N  A  V  T  S  S  -
                                       --- copB protein --->

CATTGAGTCAAAAGCGGTTTGTGCGCAGAGGTAAGCCTATGACTGACTCTGAGAAACAAA
  301  ---------+---------+---------+---------+---------+---------+  360
       GTAACTCAGTTTTCGCCAAACACGCGTCTCCATTCGGATACTGACTGAGACTCTTTGTTT
  c      L  S  Q  K  R  F  V  R  R  G  K  P  M  T  D  S  E  K  Q  M  -

TGGCCGTTGTTGCAAGAAAACGTCTTACACACAAAGAGATAAAAGTTTTTGTCAAAAATC
  361  ---------+---------+---------+---------+---------+---------+  420
       ACCGGCAACAACGTTCTTTTGCAGAATGTGTGTTTCTCTATTTTCAAAAACAGTTTTTAG
  c       A  V  V  A  R  K  R  L  T  H  K  E  I  K  V  F  V  K  N  P  -

S
                         c
                         a
                         I
       CTCTGAAGGATCTCATGGTTGAGTACTGCGAGAGAGAGGGGATAACACAGGCTCAGTTCG
  421  ---------+---------+---------+---------+---------+---------+  480
       GAGACTTCCTAGAGTACCAACTCATGACGCTCTCTCTCCCTATTGTGTCCGAGTCAAGC
  c         L  K  D  L  M  V  E  Y  C  E  R  E  G  I  T  Q  A  Q  F  V  -
```

FIG. 5B

```
                                                                  -35
                                                                ------
                            ---- Promoter (PrepA) -------->
                                       |-- copB binding site --|
          TTGAGAAAATCATCAAAGATGAACTGCAAAGACTGGATATACTAAAGTAAAGACTTTACT
      481 ------------------------------------------------------------ 540
          AACTCTTTTAGTAGTTTCTACTTGACGTTTCTGACCTATATGATTTCATTTCTGAAATGA
        c      E  K  I  I  K  D  E  L  Q  R  L  D  I  L  K  *

-10
                     -------
          TTGTGGCGTAGCATGCTAGATTACTGATCGTTTAAGGAATTTTGTGGCTGGCCACGCCGT
      541 ------------------------------------------------------------ 600
          AACACCGCATCGTACGATCTAATGACTAGCAAATTCCTTAAAACACCGACCGGTGCGGCA
                                             |-- mRNA -->
                        D
                      B r
                      m d
                      n I
                      I I
          AAGGTGGCAAGGAACTGGTTCTGATGTGGATTTACAGGAGCCAGAAAAGCAAAAACCCCG
      601 ------------------------------------------------------------ 660
          TTCCACCGTTCCTTGACCAAGACTACACCTAAATGTCCTCGGTCTTTTCGTTTTTGGGGC
        c                   M  W  I  Y  R  S  Q  K  S  K  N  P  D -
                        --- copT (ORF) --->

<-------- copA RNAI --------------------------------
          ATAATCTTCTTCAACTTTTGCGAGTACGAAAAGATTACCGGGGCCCCACTTAAACCGTATA
      661 ------------------------------------------------------------ 720
          TATTAGAAGAAGTTGAAAACGCTCATGCTTTTCTAATGGCCCCGGGTGAATTTGGCATAT
        c      N  L  L  Q  L  L  R  V  R  K  D  Y  R  G  P  L  K  P  Y  S -

<------- Promoter (RNAI) ----------
                             -10                -35
                           -------            ------
          <--------------|
          GCCAACAATTCAGCTATGCGGGGAGTATAGTTATATGCCCGGAAAAGTTCAAGACTTCTT
      721 ------------------------------------------------------------ 780
          CGGTTGTTAAGTCGATACGCCCCTCATATCAATATACGGGCCTTTTCAAGTTCTGAAGAA
        c      Q  Q  F  S  Y  A  G  S  I  V  I  C  P  E  K  F  K  T  S  F -

TCTGTGCTCGCTCCTTCTGCGCATTGTAAGTGCAGGATGGTGTGACTGATCTTCACCAAA
      781 ------------------------------------------------------------ 840
          AGACACGAGCGAGGAAGACGCGTAACATTCACGTCCTACCACACTGACTAGAAGTGGTTT
        c       C  A  R  S  F  C  A  L  *        M  T  D  L  H  Q  T -
                                                --- repA1 protein --->
                                                       D
                                                       r
                                                       a
                                                       I
                                                       I
                                                       I
          CGTATTACCGCCAGGTAAAGAACCCGAATCCGGTGTTTACACCCCGTGAAGGTGCAGGAA
      841 ------------------------------------------------------------ 900
          GCATAATGGCGGTCCATTTCTTGGGCTTAGGCCACAAATGTGGGGCACTTCCACGTCCTT
        c      Y  Y  R  Q  V  K  N  P  N  P  V  F  T  P  R  E  G  A  G  T -

CGCTGAAGTTCTGCGAAAAACTGATGGAAAAGGCGGTGGGCTTCACTTCCCGTTTTGATT
      901 ------------------------------------------------------------ 960
          GCGACTTCAAGACGCTTTTTGACTACCTTTTCCGCCACCCGAAGTGAAGGGCAAAACTAA
        c      L  K  F  C  E  K  L  M  E  K  A  V  G  F  T  S  R  F  D  F -
```

FIG. 5C

```
                        B
                        s
                        t
                        B
                        I
         TCGCCATTCATGTGGCGCACGCCCGTTCGCGTGATCTGCGTCGCCGTATGCCACCAGTGC
    961  ---------+---------+---------+---------+---------+---------+ 1020
         AGCGGTAAGTACACCGCGTGCGGGCAAGCGCACTAGACGCAGCGGCATACGGTGGTCACG
    c       A  I  H  V  A  H  A  R  S  R  D  L  R  R  R  M  P  P  V  L -

TGCGTCGTCGGGCTATTGATGCGCTCTTGCAGGGGCTGTGTTTCCACTATGACCCGCTGG
   1021  ---------+---------+---------+---------+---------+---------+ 1080
         ACGCAGCAGCCCGATAACTACGCGAGAACGTCCCCGACACAAAGGTGATACTGGGCGACC
    c       R  R  R  A  I  D  A  L  L  Q  G  L  C  F  H  Y  D  P  L  A -

CCAACCGCGTCCAGTGCTCCATCACCACGCTGGCCATTGAGTGCGGACTGGCGACGGAGT
   1081  ---------+---------+---------+---------+---------+---------+ 1140
         GGTTGGCGCAGGTCACGAGGTAGTGGTGCGACCGGTAACTCACGCCTGACCGCTGCCTCA
    c       N  R  V  Q  C  S  I  T  T  L  A  I  E  C  G  L  A  T  E  S -
                                                A
                                                c
                                                e
                                                I
                                                I
                                                I
         CTGCTGCCGGAAAACTCTCCATCACCCGTGCCACCCGTGCCCTGACGTTCCTGTCAGAGC
   1141  ---------+---------+---------+---------+---------+---------+ 1200
         GACGACGGCCTTTTGAGAGGTAGTGGGCACGGTGGGCACGGGACTGCAAGGACAGTCTCG
    c       A  A  G  K  L  S  I  T  R  A  T  R  A  L  T  F  L  S  E  L -

TGGGACTGATTACCTACCAGACGGAATATGACCCGCTTATCGGGTGCTACATTCCGACCG
   1201  ---------+---------+---------+---------+---------+---------+ 1250
         ACCCTGACTAATGGATGGTCTGCCTTATACTGGGCGAATAGCCCACGATGTAAGGCTGGC
    c       G  L  I  T  Y  Q  T  E  Y  D  P  L  I  G  C  Y  I  P  T  D -

ATATCACGTTCACATCTGCACTGTTTGCTGCCCTCGATGTATCAGAGGAGGCAGTGGCCG
   1261  ---------+---------+---------+---------+---------+---------+ 1320
         TATAGTGCAAGTGTAGACGTGACAAACGACGGGAGCTACATAGTCTCCTCCGTCACCGGC
    c       I  T  F  T  S  A  L  F  A  A  L  D  V  S  E  E  A  V  A  A -

CCGCGCGCCGCAGCCGTGTGGTATGGGAAAAACAAACAACGCAAAAAGCAGGGGCTGGATA
   1321  ---------+---------+---------+---------+---------+---------+ 1380
         GGCGCGCGGCGTCGGCACACCATACCCTTTTGTTTGTTGCGTTTTTCGTCCCCGACCTAT
    c       A  R  R  S  R  V  V  W  E  N  K  Q  R  K  K  Q  G  L  D  T -

CCCTGGGCATGGATGAACTGATAGCGAAAGCCTGGCGTTTTGTTCGTGAGCGTTTTCGCA
   1381  ---------+---------+---------+---------+---------+---------+ 1440
         GGGACCCGTACCTACTTGACTATCGCTTTCGGACCGCAAAACAAGCACTCGCAAAAGCGT
    c       L  G  M  D  E  L  I  A  K  A  W  R  F  V  R  E  R  F  R  S -
                        A
                        f
                        l
                        I
                        I
         GTTATCAGACAGAGCTTAAGTCCCGTGGAATAAAGCGTGCCCGTGCGCGTCGTGATGCGG
   1441  ---------+---------+---------+---------+---------+---------+ 1500
         CAATAGTCTGTCTCGAATTCAGGGCACCTTATTTCGCACGGGCACGCGCAGCACTACGCC
    c       Y  Q  T  E  L  K  S  R  G  I  K  R  A  R  A  R  R  D  A  D -
```

FIG. 5D

```
     ACAGGGAACGTCAGGATATTGTCACCCTGGTGAAACGGCAGCTGACGCGCGAAATCGCGG
1501 ---------+---------+---------+---------+---------+---------+ 1560
     TGTCCCTTGCAGTCCTATAACAGTGGGACCACTTTGCCGTCGACTGCGCGCTTTAGCGCC
  c    R  E  R  Q  D  I  V  T  L  V  K  R  Q  L  T  R  E  I  A  E  -

AAGGGCGCTTCACTGCCAATCGTGAGGCGGTAAAACGCGAAGTTGAGCGTCGTGTGAAGG
1561 ---------+---------+---------+---------+---------+---------+ 1620
     TTCCCGCGAAGTGACGGTTAGCACTCCGCCATTTTGCGCTTCAACTCGCAGCACACTTCC
  c    G  R  F  T  A  N  R  E  A  V  K  R  E  V  E  R  R  V  K  E  -

AGCGCATGATTCTGTCACGTAACCGTAATTACAGCCGGCTGGCCACAGCTTCCCCCTGAA
1621 ---------+---------+---------+---------+---------+---------+ 1680
     TCGCGTACTAAGACAGTGCATTGGCATTAATGTCGGCCGACCGGTGTCGAAGGGGGACTT
  c    R  M  I  L  S  R  N  R  N  Y  S  R  L  A  T  A  S  P  *

AGTGACCTCCTCTGAATAATCCGGCCTGCGCCGGAGGCTTCCGCACGTCTGAAGCCCGAC
1681 ---------+---------+---------+---------+---------+---------+ 1740
     TCACTGGAGGAGACTTATTAGGCCGGACGCGGCCTCCGAAGGCGTGCAGACTTCGGGCTG
                                                              P
                                                              f
                                                              l
                                                              M
                                                              I
     AGCGCACAAAAAATCAGCACCACATACAAAAAACAACCTCATCATCCAGCTTCTGGTGCA
1741 ---------+---------+---------+---------+---------+---------+ 1800
     TCGCGTGTTTTTTAGTCGTGGTGTATGTTTTTTGTTGGAGTAGTAGGTCGAAGACCACGT

TCCGGCCCCCCCTGTTTTCGATACAAAACACGCCTCACAGACGGGGAATTTTGCTTATCC
1801 ---------+---------+---------+---------+---------+---------+ 1860
     AGGCCGGGGGGGACAAAAGCTATGTTTTGTGCGGAGTGTCTGCCCCTTAAAACGAATAGG

|------------------- ori ---------------------
     ACATTAAACTGCAAGGGACTTCCCCATAAGGTTACAACCGTTCATGTCATAAAGCGCCAT
1861 ---------+---------+---------+---------+---------+---------+ 1920
     TGTAATTTGACGTTCCCTGAAGGGGTATTCCAATGTTGGCAAGTACAGTATTTCGCGGTA ------------------- ori ---------------------
     CCGCCAGCGTTACAGGGTGCAATGTATCTTTTAAACACCTGTTTATATCTCCTTTAAACT
1921 ---------+---------+---------+---------+---------+---------+ 1980
     GGCGGTCGCAATGTCCCACGTTACATAGAAAATTTGTGGACAAATATAGAGGAAATTTGA ---------------------------|
     ACTTAATTACATTCATTTAAAAAGAAAACCTATTCACTGCCTGTCCTTGGACAGACAGAT
1981 ---------+---------+---------+---------+---------+---------+ 2040
     TGAATTAATGTAAGTAAATTTTTCTTTTGGATAAGTGACGGACAGGAACCTGTCTGTCTA ATGCACCTCCCACCGCAAGCGGCGGGCCCCTACCGGAGCCGCTTTAGTTACAACACTCAG
2041 ---------+---------+---------+---------+---------+---------+ 2100
     TACGTGGAGGGTGGCGTTCGCCGCCCGGGGATGGCCTCGGCGAAATCAATGTTGTGAGTC
  a    M  H  L  P  P  Q  A  A  G  P  Y  R  S  R  F  S  Y  N  T  Q  -
     --- repA4 protein --->                               |-------->

ACACAACCACCAGAAAAACCCCGGTCCAGCGCAGAACTGAAACCACAAAGCCCCTCCCTC
2101 ---------+---------+---------+---------+---------+---------+ 2160
     TGTGTTGGTGGTCTTTTTGGGGCCAGGTCGCGTCTTGACTTTGGTGTTTCGGGGAGGGAG
  a    T  Q  P  P  E  K  P  R  S  S  A  E  L  K  P  Q  S  P  S  L  -

ATAACTGAAAAGCGGCCCCGCCCCGGTCCGAAGGGCCGGAACAGAGTCGCTTTTAATTAT
2161 ---------+---------+---------+---------+---------+---------+ 2220
     TATTGACTTTTCGCCGGGGCGGGGCCAGGCTTCCCGGCCTTGTCTCAGCGAAAATTAATA
  a    I  T  E  K  R  P  R  P  G  P  K  G  R  N  R  V  A  F  N  Y  -
```

FIG. 5E

```
              GAATGTTGTAACTACTTCATCATCGCTGTCAGTCTTCTCGCTGGAAGTTCTCAGTACACG
     2221   ------------+---------+---------+---------+---------+---------+  2280
              CTTACAACATTGATGAAGTAGTAGCGACAGTCAGAAGAGCGACCTTCAAGAGTCATGTGC
     a         E  C  C  N  Y  F  I  I  A  V  S  L  L  A  G  S  S  Q  Y  T   -
                                        B S
                                        g f
                                        l l
                                        I I
                                         /
              CTCGTAAGCGGCCCTGACGGCCCGCTAACGCGGAGATACGCCCCGACTTCGGGTAAACCC
     2281   ------------+---------+---------+---------+---------+---------+  2340
              GAGCATTCGCCGGGACTGCCGGGCGATTGCGCCTCTATGCGGGGCTGAAGCCCATTTGGG
     a         L  V  S  G  P  D  G  P  L  T  R  R  Y  A  P  T  S  G  K  P   -

TCGTCGGACCACTCCGACCGCGCACAGAAGCTCTCTCATGGCTGAAAGCGGGTATGGTC
     2341   ------------+---------+---------+---------+---------+---------+  2400
              AGCAGCCCTGGTGAGGCTGGCGCGTGTCTTCGAGAGAGTACCGACTTTCGCCCATACCAG
     a         S  S  G  P  L  R  P  R  T  E  A  L  S  W  L  K  A  G  M  V   -

TGGCAGGGCTGGGGATGGGTAAGGTGAAATCTATCAATCAGTACCGGCTTACGCCGGGCT
     2401   ------------+---------+---------+---------+---------+---------+  2460
              ACCGTCCCGACCCCTACCCATTCCACTTTAGATAGTTAGTCATGGCCGAATGCGGCCCGA
     a         W  Q  G  W  G  W  V  R  *
                                                                  B
                                                                  s
                                                                  t
                                                                  E
                                                                  I
                                                                  I
              TCGGCGGTTTTACTCCTGTTTCATATATGAAACAACAGGTCACCGCCTTCCATGCCGCTG
     2461   ------------+---------+---------+---------+---------+---------+  2520
              AGCCGCCAAAATGAGGACAAAGTATATACTTTGTTGTCCAGTGGCGGAAGGTACGGCGAC
                                                        B
                                                        s
                                                        p
                                                        L
                                                        U
                                                        1
                                                        1
                                                        I
              ATGCGGCATATCCTGGTAACGATATCTGAATTGTTATACATGTGTATATACGTGGTAATG
     2521   ------------+---------+---------+---------+---------+---------+  2580
              TACGCCGTATAGGACCATTGCTATAGACTTAACAATATGTACACATATATGCACCATTAC

ACAAAAATAGGACAAGTTAAAAATTTACAGGCGATGCAATGATTCAAACACGTAATCAAT
     2581   ------------+---------+---------+---------+---------+---------+  2640
              TGTTTTTATCCTGTTCAATTTTTAAATGTCCGCTACGTTACTAAGTTTGTGCATTAGTTA

ATCGGGGGTGGGCGAAGAACTCCAGCATGAGATCCCCGCGCTGGAGGATCATCCAGCCGG
     2641   ------------+---------+---------+---------+---------+---------+  2700
              TAGCCCCCACCCGCTTCTTGAGGTCGTACTCTAGGGGCGCGACCTCCTAGTAGGTCGGCC

CGTCCGGAAAACGATTCCGAAGCCCAACCTTTCATAGAAGGCGGCGGTGGAATCGAAAT
     2701   ------------+---------+---------+---------+---------+---------+  2760
              GCAGGGCCTTTTGCTAAGGCTTCGGGTTGGAAAGTATCTTCCGCCGCCACCTTAGCTTTA
```

FIG. 5F

```
                                          N              B
                                          s              p
                                          p              l
                                          V              I
         CTCGTGATGGCAGGTTGGGCGTCGCTTGGTCGGTCATTTCGAACCCCAGAGTCCCGCTCA
    2761 ---------+---------+---------+---------+---------+---------+ 2820
         GAGCACTACCGTCCAACCCGCAGCGAACCAGCCAGTAAAGCTTGGGGTCTCAGGGCGAGT

GAAGAACTCGTCAAGAAGGCGATAGAAGGCGATGCGCTGCGAATCGGGAGCGGCGATACC
    2821 ---------+---------+---------+---------+---------+---------+ 2880
         CTTCTTGAGCAGTTCTTCCGCTATCTTCCGCTACGCGACGCTTAGCCCTCGCCGCTATGG
      f    *  F  F  E  D  L  L  R  Y  F  A  I  R  Q  S  D  F  A  A  I  G -
             <--- APHII protein [kanamycin resistance gene] ---

GTAAAGCACGAGGAAGCGGTCAGCCCATTCGCCGCCAAGCTCTTCAGCAATATCACGGGT
    2881 ---------+---------+---------+---------+---------+---------+ 2940
         CATTTCGTGCTCCTTCGCCAGTCGGGTAAGCGGCGGTTCGAGAAGTCGTTATAGTGCCCA
      f       Y  L  V  L  F  R  D  A  W  E  G  G  L  E  E  A  I  D  R  T -

AGCCAACGCTATGTCCTGATAGCGGTCCGCCACACCCAGCCGGCCACAGTCGATGAATCC
    2941 ---------+---------+---------+---------+---------+---------+ 3000
         TCGGTTGCGATACAGGACTATCGCCAGGCGGTGTGGGTCGGCCGGTGTCAGCTACTTAGG
      f       A  L  A  I  D  Q  Y  R  D  A  V  G  L  R  G  C  D  I  F  G -

AGAAAAGCGGCCATTTTCCACCATGATATTCGGCAAGCAGGCATCGCCATGAGTCACGAC
    3001 ---------+---------+---------+---------+---------+---------+ 3060
         TCTTTTCGCCGGTAAAAGGTGGTACTATAAGCCGTTCGTCCGTAGCGGTACTCAGTGCTG
      f       S  F  R  G  N  E  V  M  I  N  P  L  C  A  D  G  H  T  V  V -

GAGATCCTCGCCGTCGGGCATGCGCGCCTTGAGCCTGGCGAACAGTTCGGCTGGCGCGAG
    3061 ---------+---------+---------+---------+---------+---------+ 3120
         CTCTAGGAGCGGCAGCCCGTACGCGCGGAACTCGGACCGCTTGTCAAGCCGACCGCGCTC
      f       L  D  E  G  D  P  M  R  A  K  L  R  A  F  L  E  A  P  A  L -

CCCCTGATGCTCTTCGTCCAGATCATCCTGATCGACAAGACCGGCTTCCATCCGAGTACG
    3121 ---------+---------+---------+---------+---------+---------+ 3180
         GGGGACTACGAGAAGCAGGTCTAGTAGGACTAGCTGTTCTGGCCGAAGGTAGGCTCATGC
      f       G  Q  H  E  E  D  L  D  D  Q  D  V  L  G  A  E  M  R  T  R -

TGCTCGCTCGATGCGATGTTTCGCTTGGTGGTCGAATGGGCAGGTAGCCGGATCAAGCGT
    3181 ---------+---------+---------+---------+---------+---------+ 3240
         ACGAGCGAGCTACGCTACAAAGCGAACCACCAGCTTACCCGTCCATCGGCCTAGTTCGCA
      f       A  R  E  I  R  H  K  A  Q  H  D  F  P  C  T  A  P  D  L  T -

ATGCAGCCGCCGCATTGCATCAGCCATGATGGATACTTTCTCGGCAGGAGCAAGGTGAGA
    3241 ---------+---------+---------+---------+---------+---------+ 3300
         TACGTCGGCGGCGTAACGTAGTCGGTACTACCTATGAAAGAGCCGTCCTCGTTCCACTCT
      f       H  L  R  R  M  A  D  A  M  I  S  V  K  E  A  P  A  L  H  S -

TGACAGGAGATCCTGCCCCGGCACTTCGCCCAATAGCAGCCAGTCCCTTCCCGCTTCAGT
    3301 ---------+---------+---------+---------+---------+---------+ 3360
         ACTGTCCTCTAGGACGGGGCCGTGAAGCGGGTTATCGTCGGTCAGGGAAGGGCGAAGTCA
      f       S  L  L  D  Q  G  P  V  E  G  L  L  W  D  R  G  A  E  T -

GACAACGTCGAGCACAGCTGCGCAAGGAACGCCCGTCGTGGCCAGCCACGATAGCCGCGC
    3361 ---------+---------+---------+---------+---------+---------+ 3420
         CTGTTGCAGCTCGTGTCGACGCGTTCCTTGCGGGCAGCACCGGTCGGTGCTATCGGCGCG
      f       V  V  D  L  V  A  A  C  P  V  G  T  T  A  L  W  S  L  R  A -

TGCCTCGTCCTGCAATTCATTCAGGACACCGGACAGGTCGGTCTTGACAAAAAGAACCGG
    3421 ---------+---------+---------+---------+---------+---------+ 3480
         ACGGAGCAGGACGTTAAGTAAGTCCTGTGGCCTGTCCAGCCAGAACTGTTTTTCTTGGCC
```

FIG. 5G

```
f       A   E   D   Q   L   E   N   L   V   G   S   L   D   T   K   V   F   L   V   P  -
        GCGCCCTGCGCTGACAGCCGGAACACGGCGGCATCAGAGCAGCCGATTGTCTGTTGTGC
3481    ---------+---------+---------+---------+---------+---------+ 3540
        CGCGGGGACGCGACTGTCGGCCTTGTGCCGCCGTAGTCTCGTCGGCTAACAGACAACACG
f           R   G   Q   A   S   L   R   F   V   A   A   D   S   C   G   I   T   Q   Q   A -
                                                            E
                                                            a
                                                            g
                                                            I
        CCAGTCATAGCCGAATAGCCTCTCCACCCAAGCGGCCGGAGAACCTGCGTGCAATCCATC
3541    ---------+---------+---------+---------+---------+---------+ 3600
        GGTCAGTATCGGCTTATCGGAGAGGTGGGTTCGCCGGCCTCTTGGACGCACGTTAGGTAG
f           W   D   Y   G   F   L   R   E   V   W   A   A   P   S   G   A   H   L   G   D -

TTGTTCAATCATGCGAAACGATCCTCATCCTGTCTCTTGATCTGATCTTGATCCCCTGCG
3601    ---------+---------+---------+---------+---------+---------+ 3660
        AACAAGTTAGTACGCTTTGCTAGGAGTAGGACAGAGAACTAGACTAGAACTAGGGGACGC
f           Q   E   I   M
<-- APHII (kanamycin resistance) protein --)
                                                                -10
                            <--- mRNA APHII ---|               ------
        CCATCAGATCCTTGGCGGCAAGAAAGCCATCCAGTTTACTTTGCAGGGCTTCCCAACCTT
3661    ---------+---------+---------+---------+---------+---------+ 3720
        GGTAGTCTAGGAACCGCCGTTCTTTCGGTAGGTCAAATGAAACGTCCCGAAGGGTTGGAA -35
                            ------
        <--------- Promoter (APHII) ------------------
        ACCAGAGGGCGCCCCAGCTGGCAATTCCGGTTCGCTTGCTGTCCATAAAACCGCCCAGTC
3721    ---------+---------+---------+---------+---------+---------+ 3780
        TGGTCTCCCGCGGGGTCGACCGTTAAGGCCAAGCGAACGACAGGTATTTTGGCGGGTCAG TAGCTATCGCCATGTAAGCCCACTGCAAGCTACCTGCTTTCTCTTTGCGCTTGCGTTTTC
3781    ---------+---------+---------+---------+---------+---------+ 3840
        ATCGATAGCGGTACATTCGGGTGACGTTCGATGGACGAAAGAGAAACGCGAACGCAAAAG CCTTGTCCAGATAGCCCAGTAGCTGACATTCATCCGGGGTCAGCACCGTTTCTGCGGACT
3841    ---------+---------+---------+---------+---------+---------+ 3900
        GGAACAGGTCTATCGGGTCATCGACTGTAAGTAGGCCCCAGTCGTGGCAAAGACGCCTGA GGCTTTCTACGTGTTCCGCTTCCTTTAGCAGCCCTTGCGCCCTGAGTGCTTGCGGCAGCG
3901    ---------+---------+---------+---------+---------+---------+ 3960
        CCGAAAGATGCACAAGGCGAAGGAAATCGTCGGGAACGCGGGACTCACGAACGCCGTCGC

|------ par locus ---------------------
        TGAAGCTACATATATGTGATCCGGGCAAATCGCTGAATATTCCTTTTGTCTCCGACCATC
3961    ---------+---------+---------+---------+---------+---------+ 4020
        ACTTCGATGTATATACACTAGGCCCGTTTAGCGACTTATAAGGAAAACAGAGGCTGGTAG
                                            B
                                            c
                                            g
                                            I
        ---------------------- par locus ------------------------
        AGGCACCTGAGTCGCTGTCTTTTTCGTGACATTCAGTTCGCTGCGCTCACGGCTCTGGCA
4021    ---------+---------+---------+---------+---------+---------+ 4080
        TCCGTGGACTCAGCGACAGAAAAAGCACTGTAAGTCAAGCGACGCGAGTGCCGAGACCGT ---------------------- par locus ------------------------
```

FIG. 5H

```
         GTGAATGGGGGTAAATGGCACTACAGGCGCCTTTTATGGATTCATGCAAGGAAACTACCC
4081    ------+---------+---------+---------+---------+---------+ 4140
         CACTTACCCCCATTTACCGTGATGTCCGCGGAAAATACCTAAGTACGTTCCTTTGATGGG

----------------- par locus -----------------
         ATAATACAAGAAAAGCCCGTCACGGGCTTCTCAGGGCGTTTTATGGCGGGTCTGCTATGT
4141    ------+---------+---------+---------+---------+---------+ 4200
         TATTATGTTCTTTTCGGGCAGTGCCCGAAGAGTCCCGCAAAATACCGCCCAGACGATACA ----------------- par locus -----------------
         GGTGCTATCTGACTTTTTGCTGTTCAGCAGTTCCTGCCCTCTGATTTTCCAGTCTGACCA
4201    ------+---------+---------+---------+---------+---------+ 4260
         CCACGATAGACTGAAAAACGACAAGTCGTCAAGGACGGGAGACTAAAAGGTCAGACTGGT ----------------- par locus -----------------
         CTTCGGATTATCCCGTGACAGGTCATTCAGACTGGCTAATGCACCCAGTAAGGCAGCGGT
4261    ------+---------+---------+---------+---------+---------+ 4320
         GAAGCCTAATAGGGCACTGTCCAGTAAGTCTGACCGATTACGTGGGTCATTCCGTCGCCA N    B
                                                              s    s
                                                              i    a
                                                              I    I
         ---------------------------------------|
         ATCATCAACAGGCTTACCCGTCTTACTGTCGAAGACGTGCGTAACGTATGCATGGTCTCC
4321    ------+---------+---------+---------+---------+---------+ 4380
         TAGTAGTTGTCCGAATGGGCAGAATGACAGCTTCTGCACGCATTGCATACGTACCAGAGG T1 hairpin
                                            ---------------->   <----
         CCATGCGAGAGTAGCGGAACTGCCAGGCATCAAATAAAACGAAAGGCTCAGTCGAAAGACT
4381    ------+---------+---------+---------+---------+---------+ 4440
         GGTACGCTCTCATCGCCTTGACGGTCCGTAGTTTATTTTGCTTTCCGAGTCAGCTTTCTGA --------------|
         GGGCCTTTCGTTTTATCTGTTGTTTGTCGGTGAACGCTCTCCTGAGTAGGACAAATCCGC
4441    ------+---------+---------+---------+---------+---------+ 4500
         CCCGGAAAGCAAAATAGACAACAAACAGCCACTTGCGAGAGGACTCATCCTGTTTAGGCG
         -- T1 stop -->| p
                      a
                      p
                      i
                      4
                      0
                      6
                      1
         CGGGAGCGGATTTGAACGTTGCGAAGCAACGGCCCGGAGGGTGGCGGGCAGGACGCCCGC
4501    ------+---------+---------+---------+---------+---------+ 4560
         GCCCTCGCCTAAACTTGCAACGCTTCGTTGCCGGGCCTCCCACCGCCCGTCCTGCGGGCG

T2 hairpin
                                            ---------------->   <----
         CATAAACTGCCAGGCATCAAATTAAGCAGAAGGCCATCCTGACGGATGGCCTTTTTGCGT
4561    ------+---------+---------+---------+---------+---------+ 4620
         GTATTTGACGGTCCGTAGTTTAATTCGTCTTCCGGTAGGACTGCCTACCGGAAAAACGCA
                                            ---- T2 stop ---->|
```

FIG. 5I

```
                                                                    A
                                                                    a
                                                                    t
                                                                    I
                                                                    I
         TTCTACAAACTCTTTTGTTTATTTTTCTAAATACATTCAAATATGGACGTCGTACTTAAC
    4621 ---------+---------+---------+---------+---------+---------+ 4680
         AAGATGTTTGAGAAAACAAATAAAAAGATTTATGTAAGTTTATACCTGCAGCATGAATTG
                                                                    *

TTTTAAAGTATGGGCAATCAATTGCTCCTGTTAAAATTGCTTTAGAAATACTTTGGCAGC
    4681 ---------+---------+---------+---------+---------+---------+ 4740
         AAAATTTCATACCCGTTAGTTAACGAGGACAATTTTAACGAAATCTTTATGAAACCGTCG
      d  *  S  K  F  Y  P  C  D  I  A  G  T  L  I  A  K  S  I  S  Q  C    -
         |<--- luxR protein ---

GGTTTGTTGTATTGAGTTTCATTTGCGCATTGGTTAAATGGAAAGTGACCGTGCGCTTAC
    4741 ---------+---------+---------+---------+---------+---------+ 4800
         CCAAACAACATAACTCAAAGTAAACGCGTAACCAATTTACCTTTCACTGGCACGCGAATG
      d     R  N  T  T  N  L  K  M  Q  A  N  T  L  H  F  T  V  T  R  K    -

TACAGCCTAATATTTTTGAAATATCCCAAGAGCTTTTTCCTTCGCATGCCCACGCTAAAC
    4801 ---------+---------+---------+---------+---------+---------+ 4860
         ATGTCGGATTATAAAAACTTTATAGGGTTCTCGAAAAAGGAAGCGTACGGGTGCGATTTG
      d     S  C  G  L  I  K  S  I  D  W  S  S  K  G  E  C  A  W  A  L    -

ATTCTTTTTCTCTTTTGGTTAAATCGTTGTTTGATTTATTATTTGCTATATTTATTTTTC
    4861 ---------+---------+---------+---------+---------+---------+ 4920
         TAAGAAAAAGAGAAAACCAATTTAGCAACAAACTAAATATAAACGATATAAATAAAAAG
      d     C  E  K  E  R  K  T  L  D  N  N  S  K  N  N  A  I  N  I  K    -

GATAATTATCAACTAGAGAAGGAACAATTAATGGTATGTTCATACACGCATGTAAAAATA
    4921 ---------+---------+---------+---------+---------+---------+ 4980
         CTATTAATAGTTGATCTCTTCCTTGTTAATTACCATACAAGTATGTGCGTACATTTTTAT
      d     R  Y  N  D  V  L  S  P  V  I  L  P  I  N  M  C  A  H  L  F    -

B
                                                                    s
                                                                    m
                                                                    I
         AACTATCTATATAGTTGTCTTTCTCTGAATGTGCAAAACTAAGCATTCCGAAGCCATTAT
    4981 ---------+---------+---------+---------+---------+---------+ 5040
         TTGATAGATATATCAACAGAAAGAGACTTACACGTTTTGATTCGTAAGGCTTCGGTAATA
      d     L  S  D  I  Y  N  D  K  E  S  H  A  F  S  L  M  G  F  G  N    -

TAGCAGTATGAATAGGGAAACTAAACCCAGTGATAAGACCTGATGATTTCGCTTCTTTAA
    5041 ---------+---------+---------+---------+---------+---------+ 5100
         ATCGTCATACTTATCCCTTTGATTTGGGTCACTATTCTGGACTACTAAAGCGAAGAAATT
      d     N  A  T  H  I  P  F  S  G  T  I  L  G  S  S  K  A  E  K       -

TTACATTTGGAGATTTTTTATTTACAGCATTGTTTTCAAATATATTCCAATTAATCGGTG
    5101 ---------+---------+---------+---------+---------+---------+ 5160
         AATGTAAACCTCTAAAAAATAAATGTCGTAACAAAAGTTTATATAAGGTTAATTAGCCAC
      d     I  V  N  P  S  K  K  N  V  A  N  N  E  F  I  N  W  N  I  P    -

AATGATTGGAGTTAGAATAATCTACTATAGGATCATATTTTATTAAATTAGCGTCATCAT
    5161 ---------+---------+---------+---------+---------+---------+ 5220
         TTACTAACCTCAATCTTATTAGATGATATCCTAGTATAAAATAATTTAATCGCAGTAGTA
      d     S  H  N  S  N  S  Y  D  V  I  P  D  Y  K  I  L  N  A  D  D    -
```

FIG. 5J

```
      AATATTGCCTCCATTTTTTAGGGTAATTATCCAGAATTGAAATATCAGATTTAACCATAG
5221  ---------+---------+---------+---------+---------+---------+  5280
      TTATAACGGAGGTAAAAAATCCCATTAATAGGTCTTAACTTTATAGTCTAAATTGGTATC
d      Y  Y  Q  R  W  K  K  P  Y  N  D  L  I  S  I  D  S  K  V  M  -

N
                        r
                        u
                        I
      AATGAGGATAAATGATCGCGAGTAAATAATATTCACAATGTACCATTTTAGTCATATCAG
5281  ---------+---------+---------+---------+---------+---------+  5340
      TTACTCCTATTTACTAGCGCTCATTTATTATAAGTGTTACATGGTAAAATCAGTATAGTC
       S  H  P  Y  I  I  A  L  L  Y  Y  E  C  H  V  M  K  T  M  D  -

ATAAGCATTGATTAATATCATTATTGCTTCTACAGGCTTTAATTTTATTAATTATTCTGT
5341  ---------+---------+---------+---------+---------+---------+  5400
      TATTCGTAACTAATTATAGTAATAACGAAGATGTCCGAAATTAAAATAATTAATAAGACA
       S  L  C  Q  N  I  D  N  N  S  R  C  A  K  I  K  N  I  I  R  -

AAGTGTCGTCGGCATTTATGTCTTTCATACCCATCTCTTTATCCTTACCTATTGTTTGTC
5401  ---------+---------+---------+---------+---------+---------+  5460
      TTCACAGCAGCCGTAAATACAGAAAGTATGGGTAGAGAAATAGGAATGGATAACAAACAG
       Y  T  D  D  A  N  I  D  K  M
          <---- luxR protein ---|

GCAAGTTTTGCGTGTTATATATCATTAAAACGGTAATAGATTGACATTTGATTCTAATAA
5461  ---------+---------+---------+---------+---------+---------+  5520
      CGTTCAAAACGCACAATATATAGTAATTTTGCCATTATCTAACTGTAAACTAAGATTATT
   <------|   <----|  <----|         <---- Promoter (luxPL) -------- luxR mRNA start sites

CRP Binding Site
   --------------------                                      -----
      ATTGGATTTTTGTCACACTATTATATCGCTTGAAATACAATTGTTTAACATAAGTACCTG
5521  ---------+---------+---------+---------+---------+---------+  5580
      TAACCTAAAAACAGTGTGATAATATAGCGAACTTTATGTTAACAAATTGTATTCATGGAC C      B
                   ----- Promoter (luxPR) ------->         l      b
   lux operator site  -35                    -10           a      a
   ---------  --------|----|                |----|         I      I
      TAGGATCGTACAGGTTTACGCAAGAAAATGGTTTGTTATAGTCGATTAATCGATTTGATT
5581  ---------+---------+---------+---------+---------+---------+  5640
      ATCCTAGCATGTCCAAATGCGTTCTTTTACCAAACAATATCAGCTAATTAGCTAAACTAA
             |---- 1209-85 ---------->                |-- mRNA start --
  >

NdeI
                                    |
      CTAGATTTGTTTTAACTAATTAAAGGAGGAATAACATATGATCGCTCCACCATGCACCAG
5641  ---------+---------+---------+---------+---------+---------+  5700
      GATCTAAACAAAATTGATTAATTTCCTCCTTATTGTATACTAGCGAGGTGGTACGTGGTC
  b                                           M  I  A  P  P  C  T  S  -
                                              |-- RANK -->

TGAGAAGCATTATGAGCATCTGGGACGGTGCTGTAACAAATGTGAACCAGGAAAGTACAT
5701  ---------+---------+---------+---------+---------+---------+  5760
      ACTCTTCGTAATACTCGTAGACCCTGCCACGACATTGTTTACACTTGGTCCTTTCATGTA
  b    E  K  H  Y  E  H  L  G  R  C  C  N  K  C  E  P  G  K  Y  M  -
```

FIG. 5K

```
         GTCTTCTAAATGCACTACTACCTCTGACAGTGTATGTCTGCCCTGTGGCCCGGATGAATA
   5761  ------------+---------+---------+---------+---------+---------+ 5820
         CAGAAGATTTACGTGATGATGGAGACTGTCACATACAGACGGGACACCGGGCCTACTTAT b       S  S  K  C  T  T  T  S  D  S  V  C  L  P  C  G  P  D  E  Y  -

CTTGGATAGCTGGAATGAAGAAGATAAATGCTTGCTGCATAAAGTTTGTGATACAGGCAA
   5821  ------------+---------+---------+---------+---------+---------+ 5880
         GAACCTATCGACCTTACTTCTTCTATTTACGAACGACGTATTTCAAACACTATGTCCGTT b       L  D  S  W  N  E  E  D  K  C  L  L  H  K  V  C  D  T  G  K  -

ApaLI
                                                                |
         GGCCCTGGTGGCCGTGGTCGCCGGCAACAGTACGACCCCCGGCGCTGCGCGTGCACGGC
   5881  ------------+---------+---------+---------+---------+---------+ 5940
         CCGGGACCACCGGCACCAGCGGCCGTTGTCATGCTGGGGGCCGCGACGCGCACGTGCCG b       A  L  V  A  V  V  A  G  N  S  T  T  P  R  R  C  A  C  T  A  -

KpnI
         Acc65I
             |  |
         TGGGTACCACTGGAGCCAGGACTGCGAGTGCTGCCGCCGCAACACCGAGTGCGCGCCGGG
   5941  ------------+---------+---------+---------+---------+---------+ 6000
         ACCCATGGTGACCTCGGTCCTGACGCTCACGACGGCGGCGTTGTGGCTCACGCGCGGCCC b       G  Y  H  W  S  Q  D  C  E  C  C  R  R  N  T  E  C  A  P  G  -

CCTGGGCGCCCAGCACCCGTTGCAGCTCAACAAGGACACAGTGTGCAAACCTTGCCTTGC
   6001  ------------+---------+---------+---------+---------+---------+ 6060
         GGACCCGCGGGTCGTGGGCAACGTCGAGTTGTTCCTGTGTCACACGTTTGGAACGGAACG b       L  G  A  Q  H  P  L  Q  L  N  K  D  T  V  C  K  P  C  L  A  -

AGGCTACTTCTCTGATGCCTTTTCCTCCACGGACAAATGCAGACCCTGGACCAACTGTAC
   6061  ------------+---------+---------+---------+---------+---------+ 6120
         TCCGATGAAGAGACTACGGAAAAGGAGGTGCCTGTTTACGTCTGGGACCTGGTTGACATG b       G  Y  F  S  D  A  F  S  S  T  D  K  C  R  P  W  T  N  C  T  -

CTTCCTTGGAAAGAGAGTAGAACATCATGGGACAGAGAAATCCGATGTGGTTTGCAGTTC
   6121  ------------+---------+---------+---------+---------+---------+ 6180
         GAAGGAACCTTTCTCTCATCTTGTAGTACCCTGTCTCTTTAGGCTACACCAAACGTCAAG b       F  L  G  K  R  V  E  H  H  G  T  E  K  S  D  V  V  C  S  S  -

AccI
                                                        SalI
                                                          | |
         TTCTCTGCCAGCTAGAAAACCACCAAATGAACCCCATGTTTACGTCGACAAAACTCACAC
   6181  ------------+---------+---------+---------+---------+---------+ 6240
         AAGAGACGGTCGATCTTTTGGTGGTTTACTTGGGGTACAAATGCAGCTGTTTTGAGTGTG b       S  L  P  A  R  K  P  P  N  E  P  H  V  Y  V  D  K  T  H  T  -
                                   <-- end RANK --||--start Fc-->
```

FIG. 5L

```
                BspEI                   AhdI
           ATGTCCACCTTGTCCAGCTCCGGAACTCCTGGGGGGACCGTCAGTCTTCCTCTTCCCCCC
     6241  ------------+---------+---------+---------+---------+---------+  6300
           TACAGGTGGAACAGGTCGAGGCCTTGAGGACCCCCCTGGCAGTCAGAAGGAGAAGGGGGG b      C  P  P  C  P  A  P  E  L  L  G  G  P  S  V  F  L  F  P  P  -

BspHI
           AAAACCCAAGGACACCCTCATGATCTCCCGGACCCCTGAGGTCACATGCGTGGTGGTGGA
     6301  ------------+---------+---------+---------+---------+---------+  6360
           TTTTGGGTTCCTGTGGGAGTACTAGAGGGCCTGGGGACTCCAGTGTACGCACCACCACCT b      K  P  K  D  T  L  M  I  S  R  T  P  E  V  T  C  V  V  V  D  -

CGTGAGCCACGAAGACCCTGAGGTCAAGTTCAACTGGTACGTGGACGGCGTGGAGGTGCA
     6361  ------------+---------+---------+---------+---------+---------+  6420
           GCACTCGGTGCTTCTGGGACTCCAGTTCAAGTTGACCATGCACCTGCCGCACCTCCACGT b      V  S  H  E  D  P  E  V  K  F  N  W  Y  V  D  G  V  E  V  H  -

TAATGCCAAGACAAAGCCGCGGGAGGAGCAGTACAACAGCACGTACCGTGTGGTCAGCGT
     6421  ------------+---------+---------+---------+---------+---------+  6480
           ATTACGGTTCTGTTTCGGCGCCCTCCTCGTCATGTTGTCGTGCATGGCACACCAGTCGCA b      N  A  K  T  K  P  R  E  E  Q  Y  N  S  T  Y  R  V  V  S  V  -

EcoNI
           CCTCACCGTCCTGCACCAGGACTGGCTGAATGGCAAGGAGTACAAGTGCAAGGTCTCCAA
     6481  ------------+---------+---------+---------+---------+---------+  6540
           GGAGTGGCAGGACGTGGTCCTGACCGACTTACCGTTCCTCATGTTCACGTTCCAGAGGTT b      L  T  V  L  H  Q  D  W  L  N  G  K  E  Y  K  C  K  V  S  N  -

CAAAGCCCTCCCAGCCCCCATCGAGAAAACCATCTCCAAAGCCAAAGGGCAGCCCCGAGA
     6541  ------------+---------+---------+---------+---------+---------+  6600
           GTTTCGGGAGGGTCGGGGGTAGCTCTTTTGGTAGAGGTTTCGGTTTCCCGTCGGGGCTCT b      K  A  L  P  A  P  I  E  K  T  I  S  K  A  K  G  Q  P  R  E  -

SmaI
                  BsrGI   BmaI |              SexAI
           ACCACAGGTGTACACCCTGCCCCCATCCCGGGATGAGCTGACCAAGAACCAGGTCAGCCT
     6601  ------------+---------+---------+---------+---------+---------+  6660
           TGGTGTCCACATGTGGGACGGGGGTAGGGCCCTACTCGACTGGTTCTTGGTCCAGTCGGA b      P  Q  V  Y  T  L  P  P  S  R  D  E  L  T  K  N  Q  V  S  L  -

GACCTGCCTGGTCAAAGGCTTCTATCCCAGCGACATCGCCGTGGAGTGGGAGAGCAATGG
     6661  ------------+---------+---------+---------+---------+---------+  6720
           CTGGACGGACCAGTTTCCGAAGATAGGGTCGCTGTAGCGGCACCTCACCCTCTCGTTACC b      T  C  L  V  K  G  F  Y  P  S  D  I  A  V  E  W  E  S  N  G  -

GCAGCCGGAGAACAACTACAAGACCACGCCTCCCGTGCTGGACTCCGACGGCTCCTTCTT
     6721  ------------+---------+---------+---------+---------+---------+  6780
           CGTCGGCCTCTTGTTGATGTTCTGGTGCGGAGGGCACGACCTGAGGCTGCCGAGGAAGAA
```

FIG. 5M

```
b         Q   P   E   N   N   Y   K   T   T   P   P   V   L   D   S   D   G   S   F   P   -
          CCTCTACAGCAAGCTCACCGTGGACAAGAGCAGGTGGCAGCAGGGGAACGTCTTCTCATG
    6781  ------------+------------+------------+------------+------------+------------+  6840
          GGAGATGTCGTTCGAGTGGCACCTGTTCTCGTCCACCGTCGTCCCCTTGCAGAAGAGTAC b         L   Y   S   K   L   T   V   D   K   S   R   W   Q   Q   G   N   V   F   S   C   -
          CTCCGTGATGCATGAGGCTCTGCACAACCACTACACGCAGAAGAGCCTCTCCCTGTCTCC
    6841  ------------+------------+------------+------------+------------+------------+  6900
          GAGGCACTACGTACTCCGAGACGTGTTGGTGATGTGCGTCTTCTCGGAGAGGGACAGAGG b         S   V   M   H   E   A   L   H   N   H   Y   T   Q   K   S   L   S   L   S   P   -
                          BamHI
                            |
          GGGTAAATAATGGATCCGCGGAAAGAAGAAGAAGAAGAAGAAAGCCCGAAAGGAAGCTGA
    6901  ------------+------------+------------+------------+------------+------------+  6960
          CCCATTTATTACCTAGGCGCCTTTCTTCTTCTTCTTCTTCTTTCGGGCTTTCCTTCGACT b         G   K   *
                        BlpI
                         |                                        T7 hairpin
                                                               ----------------->  <----
          GTTGGCTGCTGCCACCGCTGAGCAATAACTAGCATAACCCCTTGGGGCCTCTAAACGGGT
    6961  ------------+------------+------------+------------+------------+------------+  7020
          CAACCGACGACGGTGGCGACTCGTTATTGATCGTATTGGGGAACCCCGGAGATTTGCCCA
                                                                              --->
          <-----------
          CTTGAGGGGTTTTTTGCTGAAAGGAGGAACCGCTCTTCACGCTCTTCACGCGGATAAATA
    7021  ------------+------------+------------+------------+------------+------------+  7080
          GAACTCCCCAAAAAACGACTTTCCTCCTTGGCGAGAAGTGCGAGAAGTGCGCCTATTTAT
          -T7 stop ---->| toop hairpin
                                                                    ---------->
          AGTAACGATCCGGTCCAGTAATGACCTCAGAACTCCATCTGGATTTGTTCAGAACGCTCG
    7081  ------------+------------+------------+------------+------------+------------+  7140
          TCATTGCTAGGCCAGGTCATTACTGGAGTCTTGAGGTAGACCTAAACAAGTCTTGCGAGC toop hairpin
          <----------
          GTTGCCGCCGGGCGTTTTTTATTGGTGAGAATCGCAGCAACTTGTCGCGCCAATCGAGCC
    7141  ------------+------------+------------+------------+------------+------------+  7200
          CAACGGCGGCCCGCAAAAAATAACCACTCTTAGCGTCGTTGAACAGCGCGGTTAGCTCGG
              -- toop stop -->|

ATGTCGTCGTCAACGACCCCCCATTCAAGAACAGCAAGCAGCATTGAGAACTTTGGAATC
    7201  ------------+------------+------------+------------+------------+------------+  7260
          TACAGCAGCAGTTGCTGGGGGTAAGTTCTTGTCGTTCGTCGTAACTCTTGAAACCTTAG

CAGTCCCTCTTCCACCTGCTGACCG
    7261  ------------+------------+------  7285
          GTCAGGGAGAAGGTGGACGACTGGC
```

FIG. 6A

```
[AatII sticky end]                    5'    GCGTAACGTATGCATGGTCTCC-
(position #4358 in pAMG21)            3' TGCACGCATTGCATACGTACCAGAGG- -CCATGCGAGAGTAGGGAACTGCCAGGCATCAAATAAAACGAAAGGCTCAGTCGAAAGACT-
-GGTACGCTCTCATCCCTTGACGGTCCGTAGTTTATTTTGCTTTCCGAGTCAGCTTTCTGA- -GGGCCTTTCGTTTTATCTGTTGTTTGTCGGTGAACGCTCTCCTGAGTAGGACAAATCCGC-
-CCCGGAAAGCAAAATAGACAACAAACAGCCACTTGCGAGAGGACTCATCCTGTTTAGGCG- -CGGGAGCGGATTTGAACGTTGCGAAGCAACGGCCCGGAGGGTGGCGGGCAGGACGCCCGC-
-GCCCTCGCCTAAACTTGCAACGCTTCGTTGCCGGGCCTCCCACCGCCCGTCCTGCGGGCG- -CATAAACTGCCAGGCATCAAATTAAGCAGAAGGCCATCCTGACGGATGGCCTTTTTGCGT-
-GTATTTGACGGTCCGTAGTTTAATTCGTCTTCCGGTAGGACTGCCTACCGGAAAAACGCA- AatII
-TTCTACAAACTCTTTTGTTTATTTTTCTAAATACATTCAAATATGGACGTCGTACTTAAC-
-AAGATGTTTGAGAAAACAAATAAAAGATTTATGTAAGTTTATACCTGCAGCATGAATTG- -TTTTAAAGTATGGGCAATCAATTGCTCCTGTTAAAATTGCTTTAGAAATACTTTGGCAGC-
-AAAATTTCATACCCGTTAGTTAACGAGGACAATTTTAACGAAATCTTTATGAAACCGTCG- -GGTTTGTTGTATTGAGTTTCATTTGCGCATTGGTTAAATGGAAAGTGACCGTGCGCTTAC-
-CCAAACAACATAACTCAAAGTAAACGCGTAACCAATTTACCTTTCACTGGCACGCGAATG- -TACAGCCTAATATTTTTGAAATATCCCAAGAGCTTTTTCCTTCGCATGCCCACGCTAAAC-
-ATGTCGGATTATAAAAACTTTATAGGGTTCTCGAAAAAGGAAGCGTACGGGTGCGATTTG- -ATTCTTTTTCTCTTTTGGTTAAATCGTTGTTTGATTTATTATTTGCTATATTTATTTTTC-
-TAAGAAAAAGAGAAAACCAATTTAGCAACAAACTAAATAATAAACGATATAAATAAAAAG- -GATAATTATCAACTAGAGAAGGAACAATTAATGGTATGTTCATACACGCATGTAAAAATA-
-CTATTAATAGTTGATCTCTTCCTTGTTAATTACCATACAAGTATGTGCGTACATTTTTAT- -AACTATCTATATAGTTGTCTTTCTCTGAATGTGCAAAACTAAGCATTCCGAAGCCATTAT-
-TTGATAGATATATCAACAGAAAGAGACTTACACGTTTTGATTCGTAAGGCTTCGGTAATA- -TAGCAGTATGAATAGGGAAACTAAACCCAGTGATAAGACCTGATGATTTCGCTTCTTTAA-
-ATCGTCATACTTATCCCTTTGATTTGGGTCACTATTCTGGACTACTAAAGCGAAGAAATT- -TTACATTTGGAGATTTTTTATTTACAGCATTGTTTTCAAATATATTCCAATTAATCGGTG-
-AATGTAAACCTCTAAAAAATAAATGTCGTAACAAAAGTTTATATAAGGTTAATTAGCCAC- -AATGATTGGAGTTAGAATAATCTACTATAGGATCATATTTTATTAAATTAGCGTCATCAT-
-TTACTAACCTCAATCTTATTAGATGATATCCTAGTATAAAATAATTTAATCGCAGTAGTA- -AATATTGCCTCCATTTTTTAGGGTAATTATCCAGAATTGAAATATCAGATTTAACCATAG-
-TTATAACGGAGGTAAAAAATCCCATTAATAGGTCTTAACTTTATAGTCTAAATTGGTATC- -AATGAGGATAAATGATCGCGAGTAAATAATATTCACAATGTACCATTTTAGTCATATCAG-
-TTACTCCTATTTACTAGCGCTCATTTATTATAAGTGTTACATGGTAAAATCAGTATAGTC- -ATAAGCATTGATTAATATCATTATTGCTTCTACAGGCTTTAATTTTATTAATTATTCTGT-
-TATTCGTAACTAATTATAGTAATAACGAAGATGTCCGAAATTAAAATAATTAATAAGACA- -AAGTGTCGTCGGCATTTATGTCTTTCATACCCATCTCTTTATCCTTACCTATTGTTTGTC-
-TTCACAGCAGCCGTAAATACAGAAAGTATGGGTAGAGAAATAGGAATGGATAACAAACAG- -GCAAGTTTTGCGTGTTATATATCATTAAAAACGGTAATAGATTGACATTTGATTCTAATAA-
-CGTTCAAAACGCACAATATATAGTAATTTTGCCATTATCTAACTGTAAACTAAGATTATT-
```

FIG. 6B

```
-ATTGGATTTTTGTCACACTATTATATCGCTTGAAATACAATTGTTTAACATAAGTACCTG-
-TAACCTAAAAACAGTGTGATAATATAGCGAACTTTATGTTAACAAATTGTATTCATGGAC-

-TAGGATCGTACAGGTTTACGCAAGAAAATGGTTTGTTATAGTCGATTAATCGATTTGATT-
-ATCCTAGCATGTCCAAATGCGTTCTTTTACCAAACAATATCAGCTAATTAGCTAAACTAA-

-CTAGATTTGTTTTAACTAATTAAAGGAGGAATAACATATGGTTAACGCGTTGGAATTCGA-
-GATCTAAACAAAATTGATTAATTTCCTCCTTATTGTATACCAATTGCGCAACCTTAAGCT-

SacII
-GCTCACTAGTGTCGACCTGCAGGGTACCATGGAAGCTTACTCGAGGATCCGCGGAAAGAA-
-CGAGTGATCACAGCTGGACGTCCCATGGTACCTTCGAATGAGCTCCTAGGCGCCTTTCTT-

-GAAGAAGAAGAAGAAAGCCCGAAAGGAAGCTGAGTTGGCTGCTGCCACCGCTGAGCAATA-
-CTTCTTCTTCTTCTTTCGGGCTTTCCTTCGACTCAACCGACGACGGTGGCGACTCGTTAT-

-ACTAGCATAACCCCTTGGGGCCTCTAAACGGGTCTTGAGGGGTTTTTTGCTGAAAGGAGG-
-TGATCGTATTGGGGAACCCCGGAGATTTGCCCAGAACTCCCCAAAAAACGACTTTCCTCC-

-AACCGCTCTTCACGCTCTTCACGC 3'         [SacII sticky end]
-TTGGCGAGAAGTGCGAGAAGTG   5'         (position #5904 in pAMG21)
```

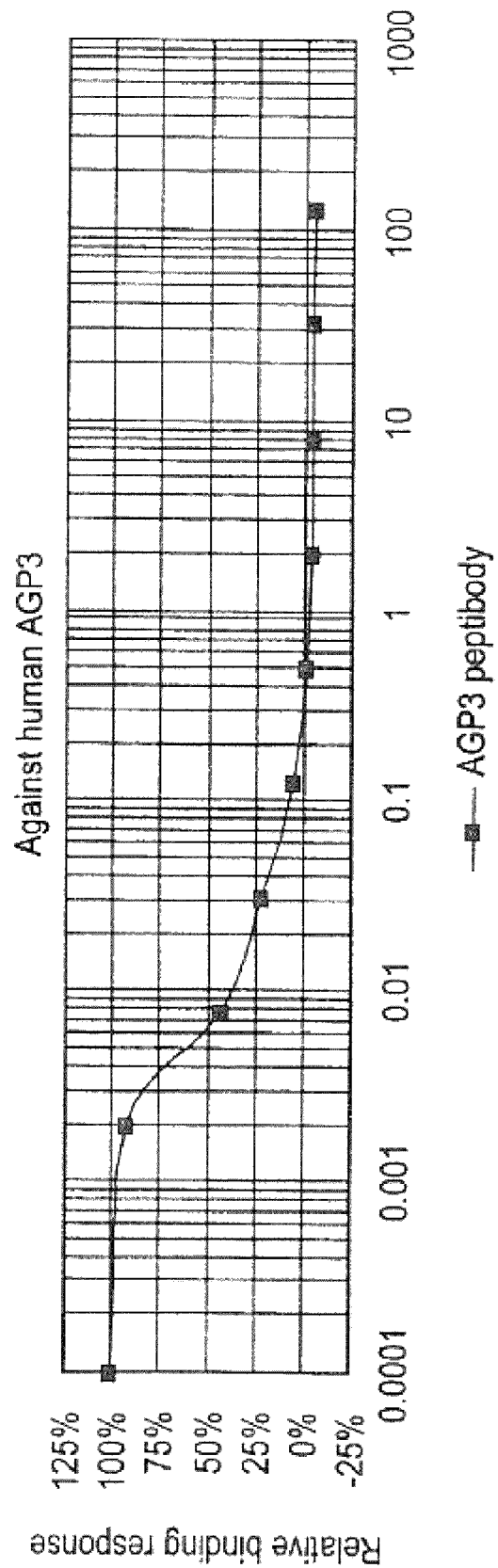

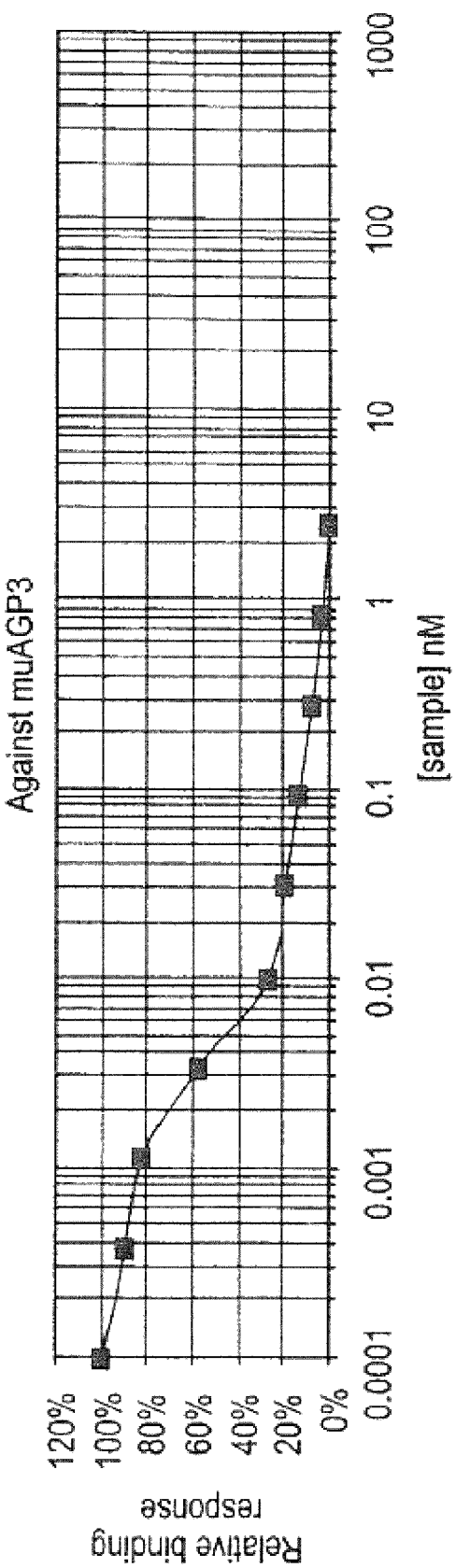

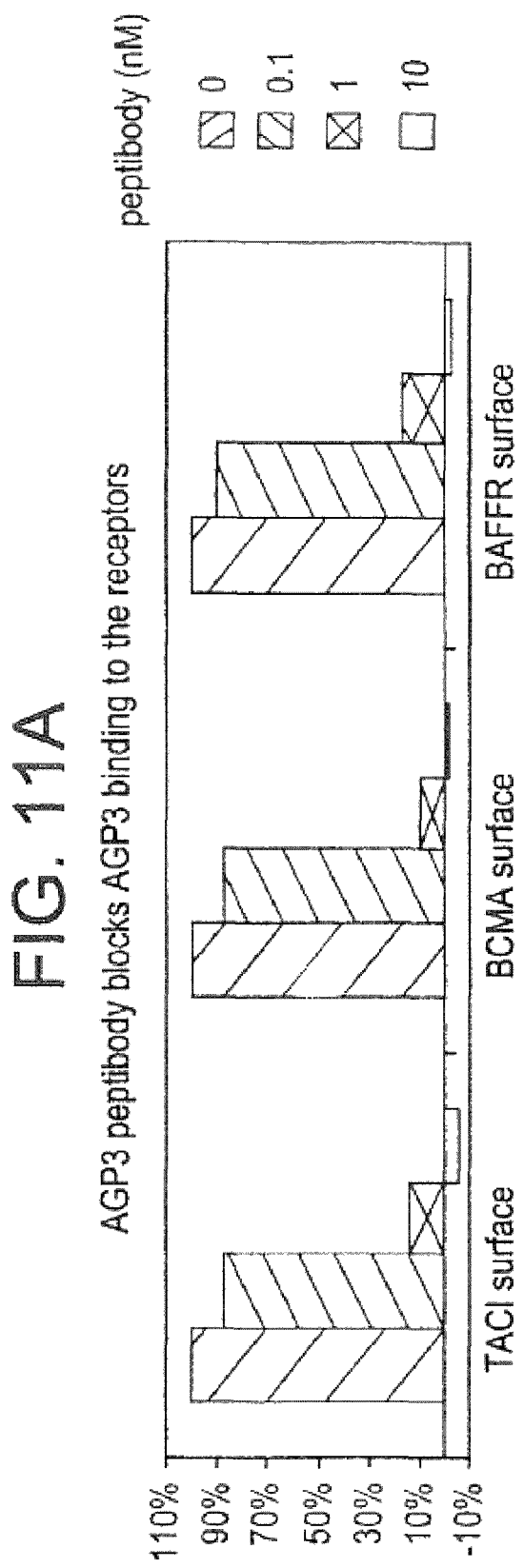

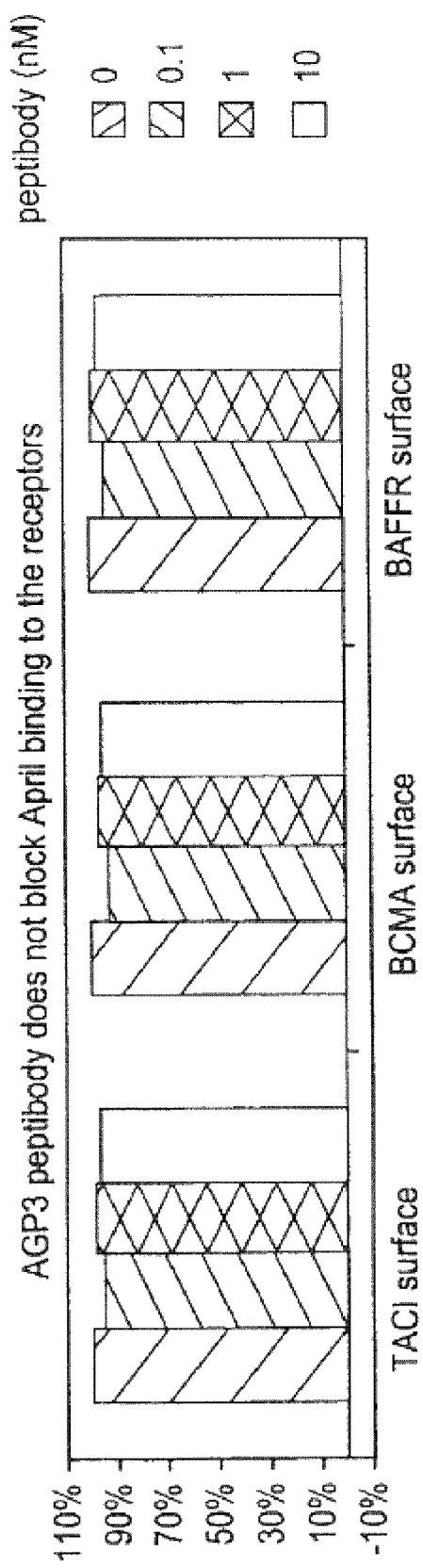

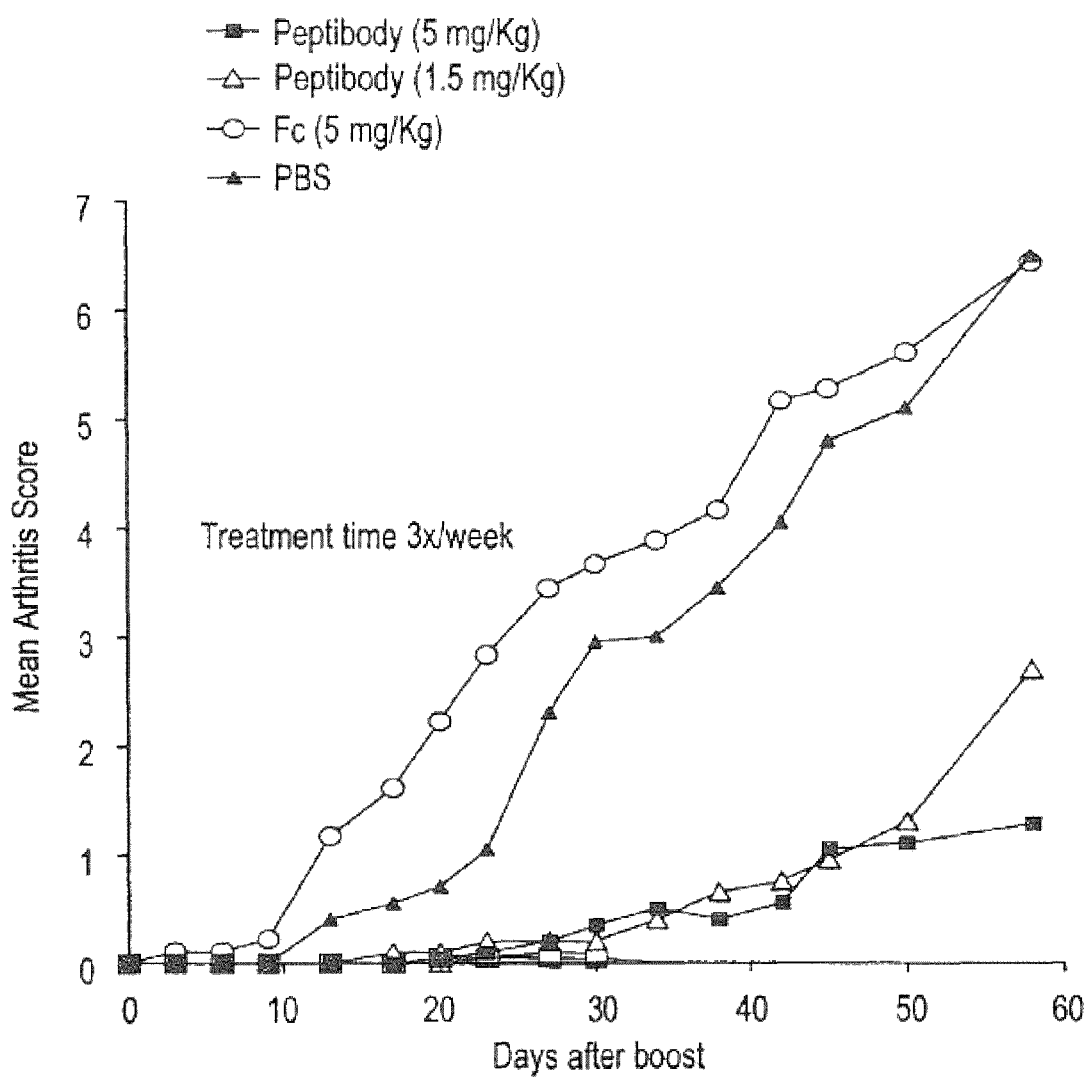

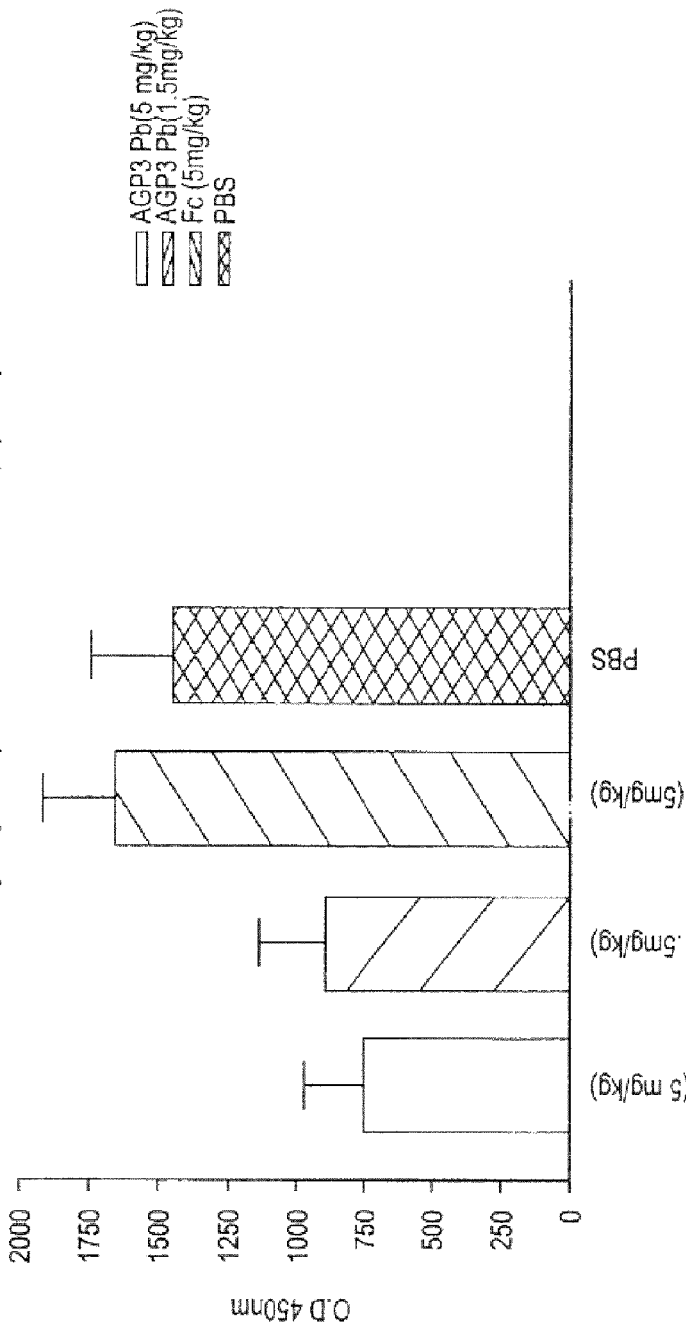

Delayed proteinuria with AGP3 protein blockers

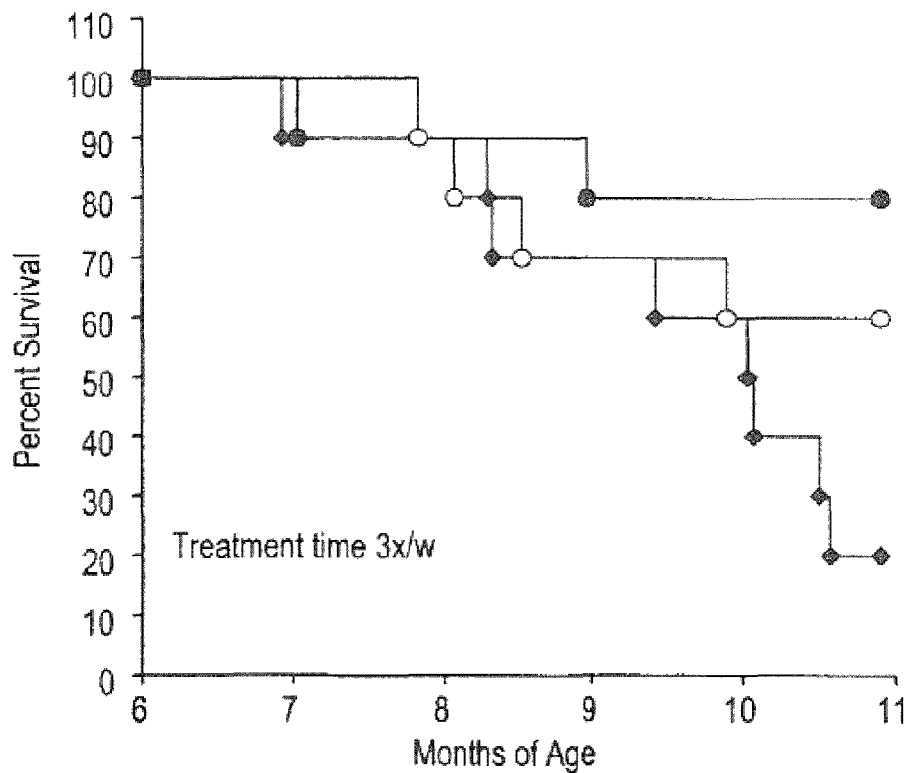

FIG. 16A

```
                                                         BamHI
                                                           |
    ATGCTTCCAGGCTGCAAGTGGGATCTTCTTATTAAGCAATGGGTATGCGATCCACTTGGA
  1 ---------+---------+---------+---------+---------+---------+  60
    TACGAAGGTCCGACGTTCACCCTAGAAGAATAATTCGTTACCCATACGCTAGGTGAACCT

M   L   P   G   C   K   W   D   L   L   I   K   Q   W   V   C   D   P   L   G   -

TCCGGTTCTGCTACTGGTGGTTCCGGCTCCACCGCAAGCTCTGGTTCAGGCAGTGCGACT
 61 ---------+---------+---------+---------+---------+---------+ 120
    AGGCCAAGACGATGACCACCAAGGCCGAGGTGGCGTTCGAGACCAAGTCCGTCACGCTGA

S   G   S   A   T   G   G   S   G   S   T   A   S   S   G   S   G   S   A   T   -

NdeI
    |
    CATATGCTGCCGGGTTGTAAATGGGACCTGCTGATCAAACAGTGGGTTTGTGACCCGCTG
121 ---------+---------+---------+---------+---------+---------+ 180
    GTATACGACGGCCCAACATTTACCCTGGACGACTAGTTTGTCACCCAAACACTGGGCGAC

H   M   L   P   G   C   K   W   D   L   L   I   K   Q   W   V   C   D   P   L   -

SalI
               |
    GGTGGAGGCGGTGGGGTCGACAAAACTCACACATGTCCACCTTGTCCAGCTCCGGAACTC
181 ---------+---------+---------+---------+---------+---------+ 240
    CCACCTCCGCCACCCCAGCTGTTTTGAGTGTGTACAGGTGGAACAGGTCGAGGCCTTGAG

G   G   G   G   V   D   K   T   H   T   C   P   P   C   P   A   P   E   L   -

CTGGGGGGACCGTCAGTCTTCCTCTTCCCCCCAAAAACCCAAGGACACCCTCATGATCTCC
241 ---------+---------+---------+---------+---------+---------+ 300
    GACCCCCCTGGCAGTCAGAAGGAGAAGGGGGGTTTTGGGTTCCTGTGGGAGTACTAGAGG

L   G   G   P   S   V   F   L   F   P   P   K   P   K   D   T   L   M   I   S   -

CGGACCCCTGAGGTCACATGCGTGGTGGTGGACGTGAGCCACGAAGACCCTGAGGTCAAG
301 ---------+---------+---------+---------+---------+---------+ 360
    GCCTGGGGACTCCAGTGTACGCACCACCACCTGCACTCGGTGCTTCTGGGACTCCAGTTC

R   T   P   E   V   T   C   V   V   V   D   V   S   H   E   D   P   E   V   K   -

TTCAACTGGTACGTGGACGGCGTGGAGGTGCATAATGCCAAGACAAAGCCGCGGGAGGAG
361 ---------+---------+---------+---------+---------+---------+ 420
    AAGTTGACCATGCACCTGCCGCACCTCCACGTATTACGGTTCTGTTTCGGCGCCCTCCTC

F   N   W   Y   V   D   G   V   E   V   H   N   A   K   T   K   P   R   E   E   -

CAGTACAACAGCACGTACCGTGTGGTCAGCGTCCTCACCGTCCTGCACCAGGACTGGCTG
421 ---------+---------+---------+---------+---------+---------+ 480
    GTCATGTTGTCGTGCATGGCACACCAGTCGCAGGAGTGGCAGGACGTGGTCCTGACCGAC

```
     AATGGCAAGGAGTACAAGTGCAAGGTCTCCAACAAAGCCCTCCCAGCCCCCATCGAGAAA
481  ---------+---------+---------+---------+---------+---------+ 540
     TTACCGTTCCTCATGTTCACGTTCCAGAGGTTGTTTCGGGAGGGTCGGGGGTAGCTCTTT

N  G  K  E  Y  K  C  K  V  S  N  K  A  L  P  A  P  I  E  K  -

ACCATCTCCAAAGCCAAAGGGCAGCCCCGAGAACCACAGGTGTACACCCTGCCCCCATCC
541  ---------+---------+---------+---------+---------+---------+ 600
     TGGTAGAGGTTTCGGTTTCCCGTCGGGGCTCTTGGTGTCCACATGTGGGACGGGGGTAGG

T  I  S  K  A  K  G  Q  P  R  E  P  Q  V  Y  T  L  P  P  S  -

CGGGATGAGCTGACCAAGAACCAGGTCAGCCTGACCTGCCTGGTCAAAGGCTTCTATCCC
601  ---------+---------+---------+---------+---------+---------+ 660
     GCCCTACTCGACTGGTTCTTGGTCCAGTCGGACTGGACGGACCAGTTTCCGAAGATAGGG

R  D  E  L  T  K  N  Q  V  S  L  T  C  L  V  K  G  F  Y  P  -

AGCGACATCGCCGTGGAGTGGGAGAGCAATGGGCAGCCGGAGAACAACTACAAGACCACG
661  ---------+---------+---------+---------+---------+---------+ 720
     TCGCTGTAGCGGCACCTCACCCTCTCGTTACCCGTCGGCCTCTTGTTGATGTTCTGGTGC

S  D  I  A  V  E  W  E  S  N  G  Q  P  E  N  N  Y  K  T  T  -

CCTCCCGTGCTGGACTCCGACGGCTCCTTCTTCCTCTACAGCAAGCTCACCGTGGACAAG
721  ---------+---------+---------+---------+---------+---------+ 780
     GGAGGGCACGACCTGAGGCTGCCGAGGAAGAAGGAGATGTCGTTCGAGTGGCACCTGTTC

P  P  V  L  D  S  D  G  S  F  F  L  Y  S  K  L  T  V  D  K  -

AGCAGGTGGCAGCAGGGGAACGTCTTCTCATGCTCCGTGATGCATGAGGCTCTGCACAAC
781  ---------+---------+---------+---------+---------+---------+ 840
     TCGTCCACCGTCGTCCCCTTGCAGAAGAGTACGAGGCACTACGTACTCCGAGACGTGTTG

S  R  W  Q  Q  G  N  V  F  S  C  S  V  M  H  E  A  L  H  N  -

CACTACACGCAGAAGAGCCTCTCCCTGTCTCCGGGTAAATAA
841  ---------+---------+---------+---------+-- 882
     GTGATGTGCGTCTTCTCGGAGAGGGACAGAGGCCCATTTATT

H  Y  T  Q  K  S  L  S  L  S  P  G  K  *   -
```

PEPTIDES AND RELATED MOLECULES THAT BIND TO TALL-1

RELATED APPLICATIONS

The present application is a Continuation of U.S. patent application Ser. No. 11/272,521, filed Nov. 10, 2005, now U.S. Pat. No. 7,737,111 which is a divisional of U.S. patent application Ser. No. 10/145,206, filed May 13, 2002, issued as U.S. Pat. No. 7,259,137, issued Aug. 21, 2007, which claims priority to U.S. Provisional Application No. 60/290, 196, filed May 11, 2001, the disclosures of which are incorporated by reference herein in their entirety, including drawings.

BACKGROUND OF THE INVENTION

After years of study in necrosis of tumors, tumor necrosis factors (TNFs) α and β were finally cloned in 1984. The ensuing years witnessed the emergence of a superfamily of TNF cytokines, including fas ligand (FasL), CD27 ligand (CD27L), CD30 ligand (CD30L), CD40 ligand (CD40L), TNF-related apoptosis-inducing ligand (TRAIL, also designated AGP-1), osteoprotegerin binding protein (OPG-BP or OPG ligand), 4-1BB ligand, LIGHT, APRIL, and TALL-1. Smith et al. (1994), Cell 76: 959-962; Lacey et al. (1998), Cell 93: 165-176; Chichepotiche et al. (1997), J. Biol. Chem. 272: 32401-32410; Mauri et al. (1998), Immunity 8: 21-30; Hahne et al. (1998), J. Exp. Med. 188: 1185-90; Shu et al. (1999), J. Leukocyte Biology 65: 680-3. This family is unified by its structure, particularly at the C-terminus. In addition, most members known to date are expressed in immune compartments, although some members are also expressed in other tissues or organs, as well. Smith et al. (1994), Cell 76: 959-62. All ligand members, with the exception of LT-α, are type II transmembrane proteins, characterized by a conserved 150 amino acid region within C-terminal extracellular domain. Though restricted to only 20-25% identity, the conserved 150 amino acid domain folds into a characteristic β-pleated sheet sandwich and trimerizes. This conserved region can be proteolytically released, thus generating a soluble functional form. Banner et al. (1993), Cell 73: 431-445.

Many members within this ligand family are expressed in lymphoid enriched tissues and play important roles in the immune system development and modulation. Smith et al. (1994). For example, TNFα is mainly synthesized by macrophages and is an important mediator for inflammatory responses and immune defenses. Tracey & Cerami (1994), Ann. Rev. Med. 45: 491-503. Fas-L, predominantly expressed in activated T cell, modulates TCR-mediated apoptosis of thymocytes. Nagata, S. & Suda, T. (1995) Immunology Today 16: 39-43; Castrim et al. (1996), Immunity 5: 617-27. CD40L, also expressed by activated T cells, provides an essential signal for B cell survival, proliferation and immunoglobulin isotype switching. Noelle (1996), Immunity 4: 415-9.

The cognate receptors for most of the TNF ligand family members have been identified. These receptors share characteristic multiple cysteine-rich repeats within their extracellular domains, and do not possess catalytic motifs within cytoplasmic regions. Smith et al. (1994). The receptors signal through direct interactions with death domain proteins (e.g. TRADD, FADD, and RIP) or with the TRAF proteins (e.g. TRAF2, TRAF3, TRAF5, and TRAF6), triggering divergent and overlapping signaling pathways, e.g. apoptosis, NF-$_K$B activation, or JNK activation. Wallach et al. (1999), Annual Review of Immunology 17: 331-67. These signaling events lead to cell death, proliferation, activation or differentiation. The expression profile of each receptor member varies. For example, TNFR1 is expressed on a broad spectrum of tissues and cells, whereas the cell surface receptor of OPGL is mainly restricted to the osteoclasts. Hsu et al. (1999) Proc. Natl. Acad. Sci. USA 96: 3540-5.

A number of research groups have recently identified TNF family ligands with the same or substantially similar sequence. The ligand has been variously named neutrokine a (WO 98/18921, published May 7, 1998), 63954 (WO 98/27114, published Jun. 25, 1998), TL5 (EP 869 180, published Oct. 7, 1998), NTN-2 (WO 98/55620 and WO 98/55621, published Dec. 10, 1998), TNRL1-alpha (WO 9911791, published Mar. 11, 1999), kay ligand (WO99/12964, published Mar. 18, 1999), and AGP-3 (U.S. Prov. App. Nos. 60/119,906, filed Feb. 12, 1999 and 60/166,271, filed Nov. 18, 1999, respectively); and TALL-1 (WO 00/68378, published Nov. 16, 2000). Each of these references is hereby incorporated by reference. Hereinafter, the ligands reported therein are collectively referred to as TALL-1.

TALL-1 is a member of the TNF ligand superfamily that is functionally involved in B cell survival and proliferation. Transgenic mice overexpressing TALL-1 had severe B cell hyperplasia and lupus-like autoimmune disease. Khare et al. (2000) PNAS 97(7):3370-3375). Both TACI and BCMA serve as cell surface receptors for TALL-1. Gross et al. (2000), Nature 404: 995-999; Ware (2000), J. Exp. Med. 192(11): F35-F37; Ware (2000), Nature 404: 949-950; Xia et al. (2000), J. Exp. Med. 192(1):137-143; Yu et al. (2000), Nature Immunology 1(3):252-256; Marsters et al. (2000), Current Biology 10:785-788; Hatzoglou et al. (2000) J. of Immunology 165:1322-1330; Shu et al. (2000) PNAS 97(16): 9156-9161; Thompson et al. (2000) J. Exp. Med. 192(1):129-135; Mukhopadhyay et al. (1999) J. Biol. Chem. 274(23): 15978-81; Shu et al. (1999) J. Leukocyte Biol. 65:680-683; Gruss et al. (1995) Blood 85(12): 3378-3404; Smith et al. (1994), Cell 76: 959-962; U.S. Pat. No. 5,969,102, issued Oct. 19, 1999; WO 00/67034, published Nov. 9, 2000; WO 00/40716, published Jul. 13, 2000; WO 99/35170, published Jul. 15, 1999. Both receptors are expressed on B cells and signal through interaction with TRAF proteins. In addition, both TACI and BCMA also bind to another TNF ligand family member, APRIL. Yu et al. (2000), Nature Immunology 1(3): 252-256. APRIL has also been demonstrated to induce B cell proliferation.

To date, no recombinant or modified proteins employing peptide modulators of TALL-1 have been disclosed. Recombinant and modified proteins are an emerging class of therapeutic agents. Useful modifications of protein therapeutic agents include combination with the "Fc" domain of an antibody and linkage to polymers such as polyethylene glycol (PEG) and dextran. Such modifications are discussed in detail in a patent application entitled, "Modified Peptides as Therapeutic Agents," publicshed WO 00/24782, which is hereby incorporated by reference in its entirety.

A much different approach to development of therapeutic agents is peptide library screening. The interaction of a protein ligand with its receptor often takes place at a relatively large interface. However, as demonstrated for human growth hormone and its receptor, only a few key residues at the interface contribute to most of the binding energy. Clackson et al. (1995), Science 267: 383-6. The bulk of the protein ligand merely displays the binding epitopes in the right topology or serves functions unrelated to binding. Thus, molecules of only "peptide" length (2 to 40 amino acids) can bind to the receptor protein of a given large protein ligand. Such peptides may mimic the bioactivity of the large protein ligand ("peptide agonists") or, through competitive binding, inhibit the bioactivity of the large protein ligand ("peptide antagonists").

Phage display peptide libraries have emerged as a powerful method in identifying such peptide agonists and antagonists. See, for example, Scott et al. (1990), Science 249: 386; Devlin et al. (1990), Science 249: 404; U.S. Pat. No. 5,223,409, issued Jun. 29, 1993; U.S. Pat. No. 5,733,731, issued Mar. 31, 1998; U.S. Pat. No. 5,498,530, issued Mar. 12, 1996; U.S. Pat. No. 5,432,018, issued Jul. 11, 1995; U.S. Pat. No. 5,338,665, issued Aug. 16, 1994; U.S. Pat. No. 5,922,545, issued Jul. 13, 1999; WO 96/40987, published Dec. 19, 1996; and WO 98/15833, published Apr. 16, 1998 (each of which is incorporated by reference in its entirety). In such libraries, random peptide sequences are displayed by fusion with coat proteins of filamentous phage. Typically, the displayed peptides are affinity-eluted against an immobilized target protein. The retained phages may be enriched by successive rounds of affinity purification and repropagation. The best binding peptides may be sequenced to identify key residues within one or more structurally related families of peptides. See, e.g., Cwirla et al. (1997), Science 276: 1696-9, in which two distinct families were identified. The peptide sequences may also suggest which residues may be safely replaced by alanine scanning or by mutagenesis at the DNA level. Mutagenesis libraries may be created and screened to further optimize the sequence of the best binders. Lowman (1997), Ann. Rev. Biophys. Biomol. Struct. 26: 401-24.

Structural analysis of protein-protein interaction may also be used to suggest peptides that mimic the binding activity of large protein ligands. In such an analysis, the crystal structure may suggest the identity and relative orientation of critical residues of the large protein ligand, from which a peptide may be designed. See, e.g., Takasaki et al. (1997), Nature Biotech. 15: 1266-70. These analytical methods may also be used to investigate the interaction between a receptor protein and peptides selected by phage display, which may suggest further modification of the peptides to increase binding affinity.

Other methods compete with phage display in peptide research. A peptide library can be fused to the carboxyl terminus of the lac repressor and expressed in E. coli. Another E. coli-based method allows display on the cell's outer membrane by fusion with a peptidoglycan-associated lipoprotein (PAL). Hereinafter, these and related methods are collectively referred to as "E. coli display." In another method, translation of random RNA is halted prior to ribosome release, resulting in a library of polypeptides with their associated RNA still attached. Hereinafter, this and related methods are collectively referred to as "ribosome display." Other methods employ peptides linked to RNA; for example, PROfusion technology, Phylos, Inc. See, for example, Roberts & Szostak (1997), Proc. Natl. Acad. Sci. USA, 94: 12297-303. Hereinafter, this and related methods are collectively referred to as "RNA-peptide screening." Chemically derived peptide libraries have been developed in which peptides are immobilized on stable, non-biological materials, such as polyethylene rods or solvent-permeable resins. Another chemically derived peptide library uses photolithography to scan peptides immobilized on glass slides. Hereinafter, these and related methods are collectively referred to as "chemical-peptide screening." Chemical-peptide screening may be advantageous in that it allows use of D-amino acids and other unnatural analogues, as well as non-peptide elements. Both biological and chemical methods are reviewed in Wells & Lowman (1992), Curr. Opin. Biotechnol. 3: 355-62. Conceptually, one may discover peptide mimetics of any protein using phage display, RNA-peptide screening, and the other methods mentioned above.

SUMMARY OF THE INVENTION

The present invention concerns therapeutic agents that modulate the activity of TALL-1. In accordance with the present invention, modulators of TALL-1 may comprise an amino acid sequence $Dz^2Lz^4$ (SEQ ID NO: 108) wherein $z^2$ is an amino acid residue and $z^4$ is threonyl or isoleucyl. Such modulators of TALL-1 comprise molecules of the following formulae:

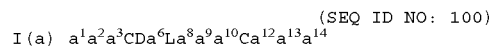

I(a) $a^1a^2a^3CDa^6La^8a^9a^{10}Ca^{12}a^{13}a^{14}$ (SEQ ID NO: 100)

wherein:
- $a^1$, $a^2$, $a^3$ are each independently absent or amino acid residues;
- $a^6$ is an amino acid residue;
- $a^9$ is a basic or hydrophobic residue;
- $a^8$ a is threonyl or isoleucyl;
- $a^{12}$ is a neutral hydrophobic residue; and
- $a^{13}$ and $a^{14}$ are each independently absent or amino acid residues.

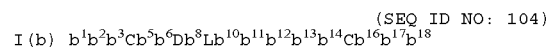

I(b) $b^1b^2b^3Cb^5b^6Db^8Lb^{10}b^{11}b^{12}b^{13}b^{14}Cb^{16}b^{17}b^{18}$ (SEQ ID NO: 104)

wherein:
- $b^1$ and $b^2$ are each independently absent or amino acid residues;
- $b^3$ is an acidic or amide residue;
- $b^5$ is an amino acid residue;
- $b^6$ is an aromatic residue;
- $b^8$ is an amino acid residue;
- $b^{10}$ is T or I;
- $b^{11}$ is a basic residue;
- $b^{12}$ and $b^{13}$ are each independently amino acid residues;
- $b^{14}$ is a neutral hydrophobic residue; and
- $b^{16}$, $b^{17}$, and $b^{18}$ are each independently absent or amino acid residues.

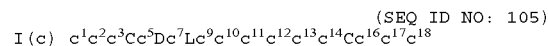

I(c) $c^1c^2c^3Cc^5Dc^7Lc^9c^{10}c^{11}c^{12}c^{13}c^{14}Cc^{16}c^{17}c^{18}$ (SEQ ID NO: 105)

wherein:
- $c^1$, $c^2$, and $c^3$ are each independently absent or amino acid residues;
- $c^5$ is an amino acid residue;
- $c^7$ is an amino acid residue;
- $c^9$ is T or I;
- $c^{10}$ is a basic residue;
- $c^{11}$ and $c^{12}$ are each independently amino acid residues;
- $c^{13}$ is a neutral hydrophobic residue;
- $c^{14}$ is an amino acid residue;
- $c^{16}$ is an amino acid residue;
- $c^{17}$ is a neutral hydrophobic residue; and
- $c^{18}$ is an amino acid residue or is absent.

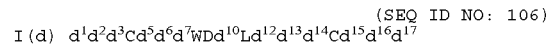

I(d) $d^1d^2d^3Cd^5d^6d^7WDd^{10}Ld^{12}d^{13}d^{14}Cd^{15}d^{16}d^{17}$ (SEQ ID NO: 106)

wherein:
- $d^1$, $d^2$, and $d^3$ are each independently absent or amino acid residues;

$d^5$, $d^6$, and $d^7$ are each independently amino acid residues;
$d^{10}$ is an amino acid residue;
$d^{13}$ is T or I;
$d^{14}$ is an amino acid residue; and
$d^{16}$, $d^{17}$, and $d^{18}$ are each independently absent or amino acid residues.

I(e)  $e^1e^2e^3Ce^5e^6e^7De^9Le^{11}Ke^{13}Ce^{15}e^{16}e^{17}e^{18}$ (SEQ ID NO: 107)

wherein:
$e^1$, $e^2$, and $e^3$ are each independently absent or amino acid residues;
$e^5$, $e^6$, $e^7$, $e^9$, and $e^{13}$ are each independently amino acid residues;
$e^{11}$ is T or I; and
$e^{15}$, $e^{16}$, and $e^{17}$ are each independently absent or amino acid residues.

I(f)  $f^1f^2f^3Kf^5Df^7Lf^9f^{10}Qf^{12}f^{13}f^{14}$ (SEQ ID NO: 109)

wherein:
$f^1$, $f^2$, and $f^3$ are absent or are amino acid residues (with one of $f^1$, $f^2$, and $f^3$ preferred to be C when one of $f^{12}$, $f^{13}$, and $f^{14}$ is C);
$f^5$ is W, Y, or F (W preferred);
$f^7$ is an amino acid residue (L preferred);
$f^9$ is T or I (T preferred);
$f^{10}$ is K, R, or H (K preferred);
$f^{12}$ is C, a neutral hydrophobic residue, or a basic residue (W, C, or R preferred);
$f^{13}$ is C, a neutral hydrophobic residue or is absent (V preferred); and
$f^{14}$ is any amino acid residue or is absent;
provided that only one of $f^1$, $f^2$, and $f^3$ may be C, and only one of $f^{12}$, f13, and $f^{14}$ may be C.

Compounds of formulae I(a) through I(f) above incorporate $Dz^2Lz^4$, as well as SEQ ID NO: 63 hereinafter. The sequence of I(f) was derived as a consensus sequence as described in Example 1 hereinbelow. Of compounds within formula I(f), those within the formula I(f')  $f^1f^2f^3KWDf^7Lf^9KQf^{12}f^{13}f^{14}$ (SEQ ID NO: 125)

are preferred. Compounds falling within formula I(f') include SEQ ID NOS: 32, 58, 60, 62, 63, 66, 67, 69, 70, 114, 115, 122, 123, 124, 147-150, 152-177, 179, 180, 187.

Also in accordance with the present invention are compounds having the consensus motif:

PFPWE (SEQ ID NO: 110)

which also bind TALL-1.

Further in accordance with the present invention are compounds of the formulae:

I(g)  $g^1g^2g^3Cg^5PFg^8Wg^{10}Cg^{11}g^{12}g^{13}$ (SEQ ID NO: 101)

wherein:
$g^1$, $g^2$ and $g^3$ are each independently absent or amino acid residues;
$g^5$ is a neutral hydrophobic residue;
$g^8$ is a neutral hydrophobic residue;
$g^{10}$ is an acidic residue;

I(h)  $h^1h^2h^3CWh^6h^7WGh^{10}Ch^{12}h^{13}h^{14}$ (SEQ ID NO: 102)

wherein:
$h^1$, $h^2$, and $h^3$ are each independently absent or amino acid residues;
$h^6$ is a hydrophobic residue;
$h^7$ is a hydrophobic residue;
$h^{10}$ is an acidic or polar hydrophobic residue; and
$h^{12}$, $h^{13}$ and $h^{14}$ are each independently absent or amino acid residues.

I(i)  $i^1i^2i^3Ci^5i^6i^7i^8i^9i^{10}Ci^{12}i^{13}i^{14}$ (SEQ ID NO: 103)

wherein:
$i^1$ is absent or is an amino acid residue;
$i^2$ is a neutral hydrophobic residue;
$i^3$ is an amino acid residue;
$i^5$, $i^6$, $i^7$, and $i^8$ are each independently amino acid residues;
$i^9$ is an acidic residue;
$i^{10}$ is an amino acid residue;
$i^{12}$ and $i^{13}$ are each independently amino acid residues; and
$i^{14}$ is a neutral hydrophobic residue.

The compounds defined by formulae I(g) through I(i) also bind TALL-1.

Further in accordance with present invention, modulators of TALL-1 comprise:
a) a TALL-1 modulating domain (e.g., an amino acid sequence of Formulae I(a) through I(i)), preferably the amino acid sequence $Dz^2Lz^4$, or sequences derived therefrom by phage display, RNA-peptide screening, or the other techniques mentioned above; and
b) a vehicle, such as a polymer (e.g., PEG or dextran) or an Fc domain, which is preferred;

wherein the vehicle is covalently attached to the TALL-1 modulating domain. The vehicle and the TALL-1 modulating domain may be linked through the N- or C-terminus of the TALL-1 modulating domain, as described further below. The preferred vehicle is an Fc domain, and the preferred Fc domain is an IgG Fc domain. Such Fc-linked peptides are referred to herein as "peptibodies." Preferred TALL-1 modulating domains comprise the amino acid sequences described hereinafter in Tables 1 and 2. Other TALL-1 modulating domains can be generated by phage display, RNA-peptide screening and the other techniques mentioned herein.

Further in accordance with the present invention is a process for making TALL-1 modulators, which comprises:
a. selecting at least one peptide that binds to TALL-1; and
b. covalently linking said peptide to a vehicle.

The preferred vehicle is an Fc domain. Step (a) is preferably carried out by selection from the peptide sequences in Table 2 hereinafter or from phage display, RNA-peptide screening, or the other techniques mentioned herein.

The compounds of this invention may be prepared by standard synthetic methods, recombinant DNA techniques, or any other methods of preparing peptides and fusion proteins. Compounds of this invention that encompass non-peptide portions may be synthesized by standard organic chemistry reactions, in addition to standard peptide chemistry reactions when applicable.

The primary use contemplated for the compounds of this invention is as therapeutic or prophylactic agents. The vehicle-linked peptide may have activity comparable to—or even greater than—the natural ligand mimicked by the peptide.

The compounds of this invention may be used for therapeutic or prophylactic purposes by formulating them with appropriate pharmaceutical carrier materials and administering an effective amount to a patient, such as a human (or other mammal) in need thereof. Other related aspects are also included in the instant invention.

Numerous additional aspects and advantages of the present invention will become apparent upon consideration of the figures and detailed description of the invention.

BRIEF DESCRIPTION OF THE FIGURES

FIG. 1 shows exemplary Fc dimers that may be derived from an IgG1 antibody. "Fc" in the figure represents any of the Fc variants within the meaning of "Fc domain" herein. "X$^1$" and "X$^2$" represent peptides or linker-peptide combinations as defined hereinafter. The specific dimers are as follows: A, D: Single disulfide-bonded dimers. IgG1 antibodies typically have two disulfide bonds at the hinge region of the antibody. The Fc domain in FIGS. 1A and 1D may be formed by truncation between the two disulfide bond sites or by substitution of a cysteinyl residue with an unreactive residue (e.g., alanyl). In FIG. 1A, the Fc domain is linked at the amino terminus of the peptides; in 1D, at the carboxyl terminus. B, E: Doubly disulfide-bonded dimers. This Fc domain may be formed by truncation of the parent antibody to retain both cysteinyl residues in the Fc domain chains or by expression from a construct including a sequence encoding such an Fc domain. In FIG. 1B, the Fc domain is linked at the amino terminus of the peptides; in 1E, at the carboxyl terminus. C, F: Noncovalent dimers. This Fc domain may be formed by elimination of the cysteinyl residues by either truncation or substitution. One may desire to eliminate the cysteinyl residues to avoid impurities formed by reaction of the cysteinyl residue with cysteinyl residues of other proteins present in the host cell. The noncovalent bonding of the Fc domains is sufficient to hold together the dimer. Other dimers may be formed by using Fc domains derived from different types of antibodies (e.g., IgG2, IgM).

FIG. 2 shows the structure of preferred compounds of the invention that feature tandem repeats of the pharmacologically active peptide. FIG. 2A shows a single chain molecule and may also represent the DNA construct for the molecule. FIG. 2B shows a dimer in which the linker-peptide portion is present on only one chain of the dimer. FIG. 2C shows a dimer having the peptide portion on both chains. The dimer of FIG. 2C will form spontaneously in certain host cells upon expression of a DNA construct encoding the single chain shown in FIG. 3A. In other host cells, the cells could be placed in conditions favoring formation of dimers or the dimers can be formed in vitro.

FIG. 3 shows exemplary nucleic acid and amino acid sequences (SEQ ID NOS: 1 and 2, respectively) of human IgG1 Fc that may be used in this invention.

FIGS. 4A through 4F show the nucleotide and amino acid sequences (SEQ ID NOS: 3-27) S of NdeI to SalI fragments encoding peptide and linker.

FIGS. 5A through 5M show the nucleotide sequence (SEQ ID NO: 28) of pAMG21-RANK-Fc vector, which was used to construct Fc-linked molecules of the present invention. These figures identify a number of features of the nucleic acid, including:
promoter regions PcopB, PrepA, RNAI, APHII, luxPR, and luxPL;
mRNA for APHII, luxR;
coding sequences and amino acid sequences for the proteins copB protein, copT, repAI, repA4, APHII, luxR, RANK, and Fc;
binding sites for the proteins copB, CRP;
hairpins T1, T2, T7, and toop;
operator site for lux protein;
enzyme restriction sites for Pfl1108I, BglII, ScaI, BmnI, DrdII, DraIII, BstBI, AceIII, AflII, PflMI, BglI, SfiI, BstEII, BspLulII, NspV, BplI, EagI, BcgI, NsiI, BsaI, Psp1406I, AatII, BsmI, NruI, NdeI, ApaLI, Acc65I, KpnI, SalI, AccI, BspEI, AhdI, BspHI, EconI, BsrGI, BmaI, SmaI, SexAI, BamHI, and BlpI.

FIGS. 6A and 6B show the DNA sequence (SEQ ID NO: 97) inserted into pCFM1656 between the unique AatII (position #4364 in pCFM1656) and SacII (position #4585 in pCFM1656) restriction sites to form expression plasmid pAMG21 (ATCC accession no. 98113).

FIGS. 10A and 10B. AGP3 peptibody blocks both human and murine AGP3 in the Biacore competition assay. Soluble human TACI protein was immobilized to B1 chip. 1 nM of recombinant human AGP3 protein (upper panel) or 5 nM of recombinant murine AGP3 protein (lower panel) was incubated with indicated amount of AGP3 peptibody before injected over the surface of receptor. Relative human AGP3 and murine AGP3 (binding response was shown (SEQ ID NO: 123).

FIGS. 11A and 11B. AGP3 peptibody blocked AGP3 binding to all three receptors TACI, BCMA and BAFFR in Biacore competition assay. Recombinant soluble receptor TACI, BCMA and BAFFR proteins were immobilized to CM5 chip. 1 nM of recombinant human AGP3 (upper panel) were incubated with indicated amount of AGP3 peptibody before injected over each receptor surface. Relative binding of AGP3 was measured. Similarly, 1 nM of recombinant APRIL protein was incubated with indicated amount of AGP3 peptibody before injected over each receptor surface. AGP3 peptibody didn't inhibit APRIL binding to all three receptors (SEQ ID NO: 123).

FIG. 13. AGP3 peptibody treatment reduced arthritis severity in the mouse CIA model. Eight to 12 weeks old DBA/1 male mice were immunized with bovine collagen type II (bCII) emulsified in complete freunds adjuvant intradermally at the base of tail, and were boosted 3 weeks after the initial immunization with bCII emulsified in incomplete freunds adjuvant. Treatment with indicated dosage of AGP3 peptibody was begun from the day of booster immunization for 4 weeks. As described before (Khare et al., J. Immunol. 155: 3653-9, 1995), all four paws were individually scored from 0-3 for arthritis severity (SEQ ID NO: 123).

FIG. 14. AGP3 peptibody treatment inhibited anti-collagen antibody generation in the mouse CIA model. Serum samples were taken one week after final treatment (day 35) as described above. Serum anti-collagen II antibody level was determined by ELISA analysis (SEQ ID NO: 123).

FIGS. 15A and 15B. AGP3 peptibody treatment delayed proteinuria onset and improved survival in NZB/NZW lupus mice. Five-month-old lupus prone NZBx NZBWF1 mice were treated i.p. 3x/week for 8 weeks with PBS or indicated doses of AGP3 peptibody (SEQ ID NO: 123) or human Fc proteins. Protein in the urine was evaluated monthly throughout the life of the experiment with Albustix reagent strips (Bayer AG).

FIGS. 16A and 16B show the nucleic acid and amino acid sequences of a preferred TALL-1-binding peptibody (SEQ ID NOS: 189 and 123).

DETAILED DESCRIPTION OF THE INVENTION

Definition of Terms

Figure 4A:
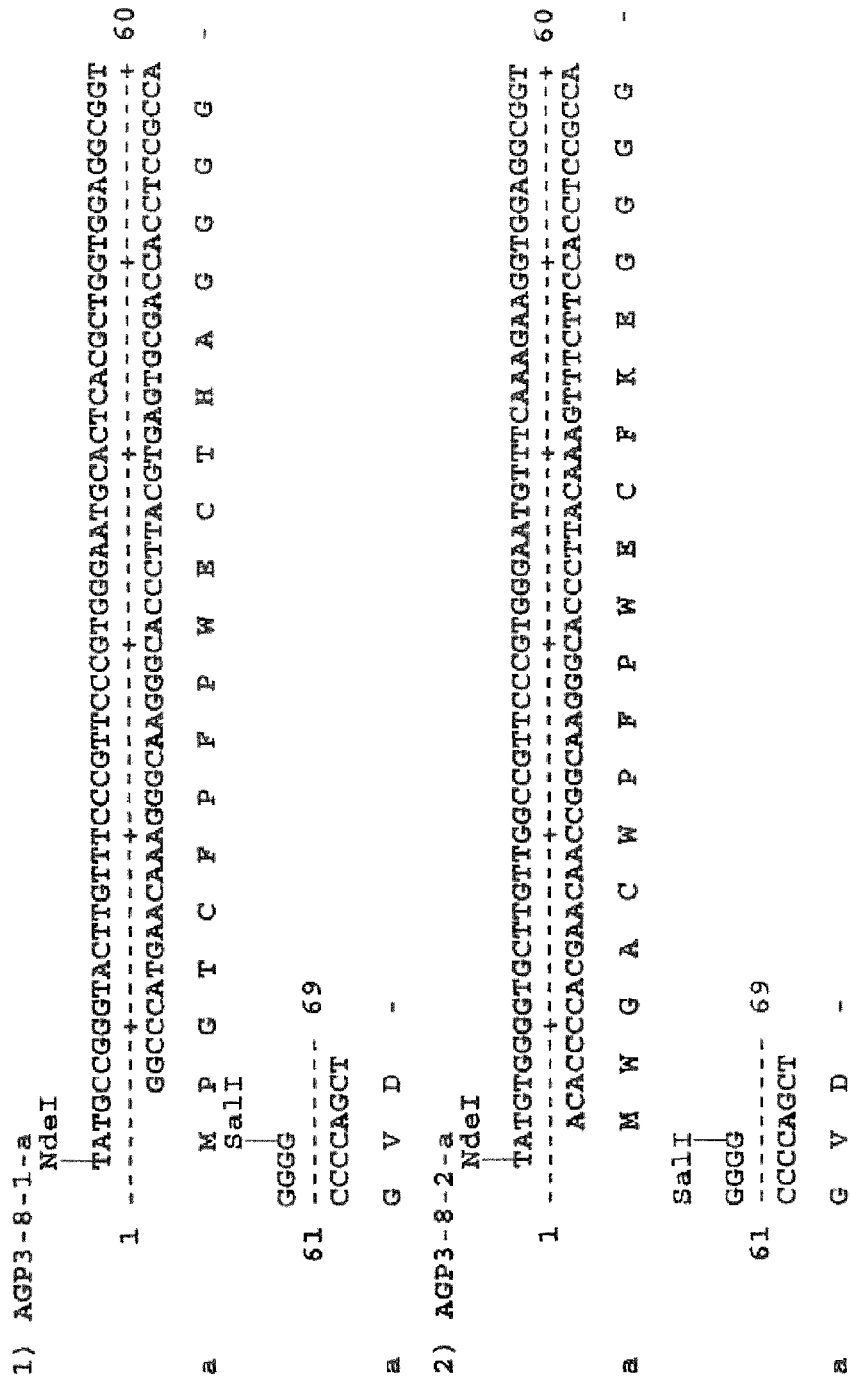
Figure 7:
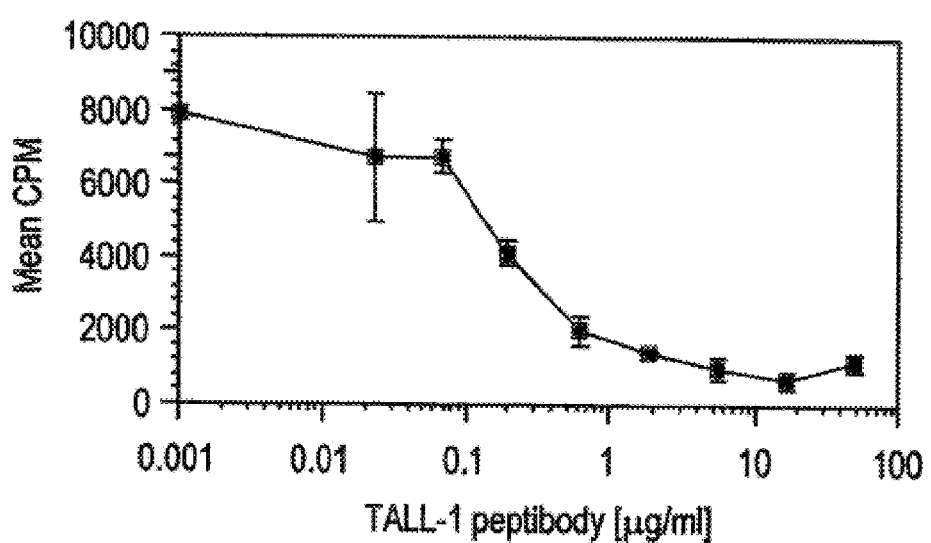
FIG. 7 shows that the TALL-1 peptibody (SEQ ID NO: 70) inhibits TALL-1-mediated B cell proliferation. Purified B cells (10$^5$) from B6 mice were cultured in triplicates in 96-well plated with the indicated amounts of TALL-1 consensus peptibody in the presence of 10 ng/ml TALL-1 plus 2 µg/ml anti-IgM antibody. Proliferation was measured by radioactive [$^3$H]thymidine uptake in the last 18 h of pulse. Data shown represent mean±SD triplicate wells.
Figure 8:
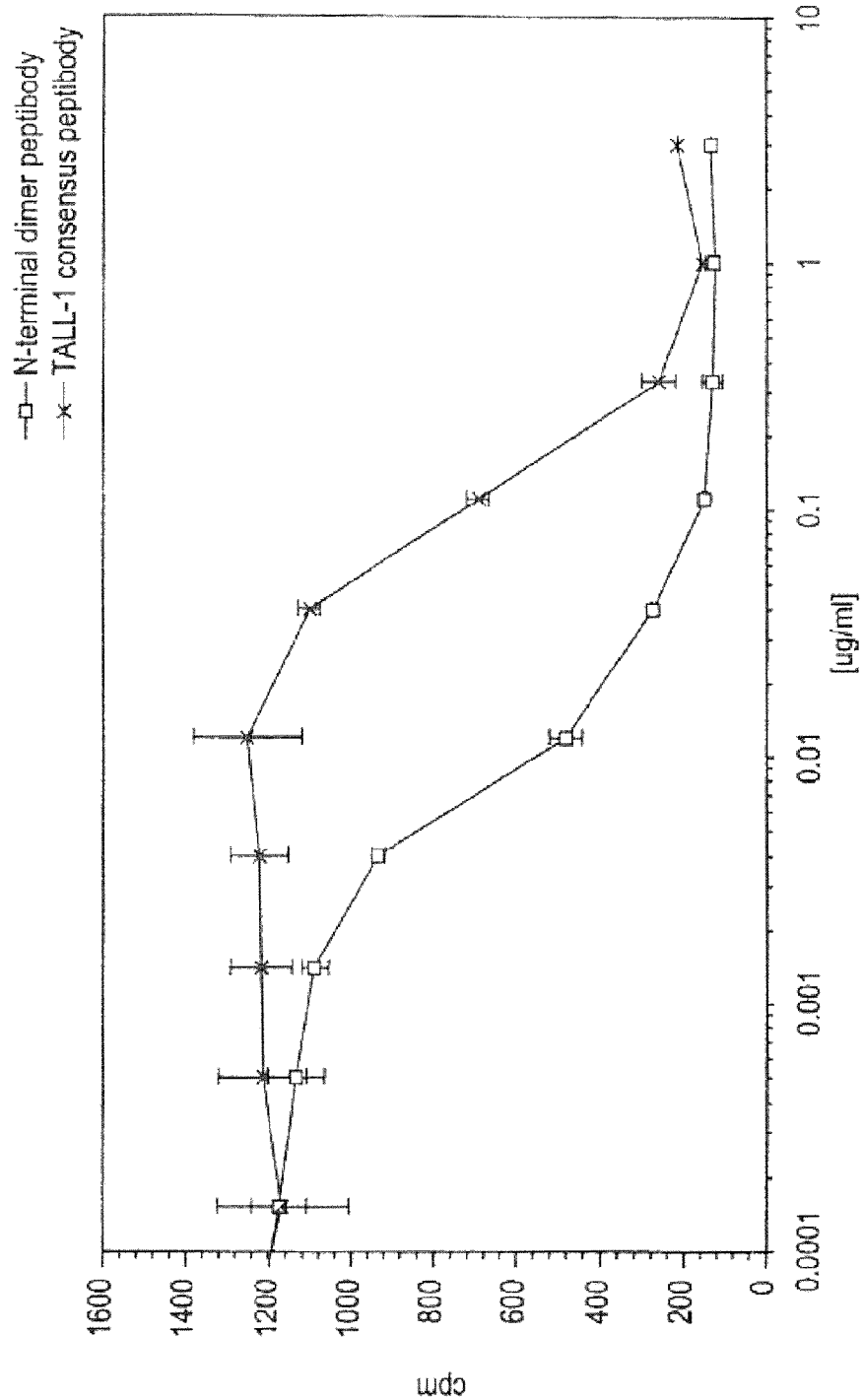
FIG. 8 shows that a TALL-1 N-terminal tandem dimer peptibodies (SEQ ID NO: 123, 124 in Table 5B hereinafter) are preferable for inhibition of TALL-1-mediated B cell proliferation. Purified B cells (10$^5$) from B6 mice were cultured in triplicates in 96-well plated with the indicated amounts of TALL-1 12-3 peptibody and TALL-1 consensus peptibody (SEQ ID NOS: 115 and 122 of Table 5B) or the related dimer peptibodies (SEQ ID NOS: 123, 124) in the presence of 10 µg/ml TALL-1 plus 2 µg/ml anti-IgM antibody. Proliferation was measured by radioactive [$^3$H]thymidine uptake in the last 18 h of pulse. Data shown represent mean±SD triplicate wells.

The terms used throughout this specification are defined as follows, unless otherwise limited in specific instances.

General Definitions

The term "comprising" means that a compound may include additional amino acids on either or both of the N- or C-termini of the given sequence. Of course, these additional amino acids should not significantly interfere with the activity of the compound.

Additionally, physiologically acceptable salts of the compounds of this invention are also encompassed herein. The term "physiologically acceptable salts" refers to any salts that are known or later discovered to be pharmaceutically acceptable. Some specific examples are: acetate; trifluoroacetate; hydrohalides, such as hydrochloride and hydrobromide; sulfate; citrate; tartrate; glycolate; and oxalate.

Amino Acids

The term "acidic residue" refers to amino acid residues in D- or L-form having sidechains comprising acidic groups. Exemplary acidic residues include D and E.

The term "amide residue" refers to amino acids in D- or L-form having sidechains comprising amide derivatives of acidic groups. Exemplary residues include N and Q.

The term "aromatic residue" refers to amino acid residues in D- or L-form having sidechains comprising aromatic groups. Exemplary aromatic residues include F, Y, and W.

The term "basic residue" refers to amino acid residues in D- or L-form having sidechains comprising basic groups. Exemplary basic residues include H, K, and R.

The term "hydrophilic residue" refers to amino acid residues in D- or L-form having sidechains comprising polar groups. Exemplary hydrophilic residues include C, S, T, N, and Q.

The term "nonfunctional residue" refers to amino acid residues in D- or L-form having sidechains that lack acidic, basic, or aromatic groups. Exemplary nonfunctional amino acid residues include M, G, A, V, I, L and norleucine (Nle).

The term "neutral hydrophobic residue" refers to amino acid residues in D- or L-form having sidechains that lack basic, acidic, or polar groups. Exemplary neutral hydrophobic amino acid residues include A, V, L, I, P, W, M, and F.

The term "polar hydrophobic residue" refers to amino acid residues in D- or L-form having sidechains comprising polar groups. Exemplary polar hydrophobic amino acid residues include T, G, S, Y, C, Q, and N.

The term "hydrophobic residue" refers to amino acid residues in D- or L-form having sidechains that lack basic or acidic groups. Exemplary hydrophobic amino acid residues include A, V, L, I, P, W, M, F, T, G, S, Y, C, Q, and N.

Peptides

The term "peptide" refers to molecules of 1 to 40 amino acids, with molecules of 5 to 20-amino acids preferred. Exemplary peptides may comprise the TALL-1 modulating domain of a naturally occurring molecule or comprise randomized sequences.

The term "randomized" as used to refer to peptide sequences refers to fully random sequences (e.g., selected by phage display methods or RNA-peptide screening) and sequences in which one or more residues of a naturally occurring molecule is replaced by an amino acid residue not appearing in that position in the naturally occurring molecule. Exemplary methods for identifying peptide sequences include phage display, E. coli display, ribosome display, RNA-peptide screening, chemical screening, and the like.

The term "TALL-1 modulating domain" refers to any amino acid sequence that binds to the TALL-1 and comprises naturally occurring sequences or randomized sequences. Exemplary TALL-1 modulating domains can be identified or derived by phage display or other methods mentioned herein.

The term "TALL-1 antagonist" refers to a molecule that binds to the TALL-1 and increases or decreases one or more assay parameters opposite from the effect on those parameters by full length native TALL-1. Such activity can be determined, for example, by such assays as described in the subsection entitled "Biological activity of AGP-3" in the Materials & Methods section of the patent application entitled, "TNF-RELATED PROTEINS", WO 00/47740, published Aug. 17, 2000.

Vehicles and Peptibodies

The term "vehicle" refers to a molecule that prevents degradation and/or increases half-life, reduces toxicity, reduces immunogenicity, or increases biological activity of a therapeutic protein. Exemplary vehicles include an Fc domain (which is preferred) as well as a linear polymer (e.g., polyethylene glycol (PEG), polylysine, dextran, etc.); a branched-chain polymer (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published 28 Oct. 1993); a lipid; a cholesterol group (such as a steroid); a carbohydrate or oligosaccharide (e.g., dextran); any natural or synthetic protein, polypeptide or peptide that binds to a salvage receptor; albumin, including human serum albumin (HSA), leucine zipper domain, and other such proteins and protein fragments. Vehicles are further described hereinafter.

The term "native Fc" refers to molecule or sequence comprising the sequence of a non-antigen-binding fragment resulting from digestion of whole antibody, whether in monomeric or multimeric form. The original immunoglobulin source of the native Fc is preferably of human origin and may be any of the immunoglobulin, although IgG1 and IgG2 are preferred. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), Nucleic Acids Res. 10: 4071-9). The term "native Fc" as used herein is generic to the monomeric, dimeric, and multimeric forms.

The term "Fc variant" refers to a molecule or sequence that is modified from a native Fc but still comprises a binding site for the salvage receptor, FcRn. International applications WO 97/34631 (published 25 Sep. 1997) and WO 96/32478 describe exemplary Fc variants, as well as interaction with the salvage receptor, and are hereby incorporated by reference in their entirety. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). Fc variants are described in further detail hereinafter.

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by other means.

The term "multimer" as applied to Fc domains or molecules comprising Fc domains refers to molecules having two or more polypeptide chains associated covalently, noncovalently, or by both covalent and non-covalent interactions. IgG molecules typically form dimers; IgM, pentamers; IgD, dimers; and IgA, monomers, dimers, trimers, or tetramers. Multimers may be formed by exploiting the sequence and resulting activity of the native Ig source of the Fc or by derivatizing (as defined below) such a native Fc.

The term "dimer" as applied to Fc domains or molecules comprising Fc domains refers to molecules having two polypeptide chains associated covalently or non-covalently. Thus, exemplary dimers within the scope of this invention are as shown in FIG. 1.

The terms "derivatizing" and "derivative" or "derivatized" comprise processes and resulting compounds respectively in which (1) the compound has a cyclic portion; for example, cross-linking between cysteinyl residues within the compound; (2) the compound is cross-linked or has a cross-linking site; for example, the compound has a cysteinyl residue and thus forms cross-linked dimers in culture or in vivo; (3) one or more peptidyl linkage is replaced by a non-peptidyl linkage; (4) the N-terminus is replaced by —$NRR^1$, $NRC(O)R^1$, —$NRC(O)OR^1$, —$NRS(O)_2R^1$, —$NHC(O)NHR$, a succinimide group, or substituted or unsubstituted benzyloxycarbonyl-NH—, wherein R and $R^1$ and the ring substituents are as defined hereinafter; (5) the C-terminus is replaced by —$C(O)R^2$ or —$NR^3$, $R^4$ wherein $R^2$, $R^3$ and $R^4$ are as defined hereinafter; and (6) compounds in which individual amino acid moieties are modified through treatment with agents capable of reacting with selected side chains or terminal residues. Derivatives are further described hereinafter.

The terms "peptibody" and "peptibodies" refer to molecules comprising an Fc domain and at least one peptide. Such peptibodies may be multimers or dimers or fragments thereof, and they may be derivatized. In the present invention, the molecules of formulae II through VI hereinafter are peptibodies when VI is an Fc domain.

Structure of Compounds

In General. The present inventors identified sequences capable of binding to and modulating the biological activity of TALL-1. These sequences can be modified through the techniques mentioned above by which one or more amino acids may be changed while maintaining or even improving the binding affinity of the peptide.

In the compositions of matter prepared in accordance with this invention, the peptide(s) may be attached to the vehicle through the peptide's N-terminus or C-terminus. Any of these peptides may be linked in tandem (i.e., sequentially), with or without linkers. Thus, the vehicle-peptide molecules of this invention may be described by the following formula:

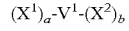            II wherein:

$V^1$ is a vehicle (preferably an Fc domain);

$X^1$ and $X^2$ are each independently selected from -$(L^1)_c$-$P^1$, -$(L^1)_c$-$P^1$-$(L^2)_d$-$P^2$, -$(L^1)_c$-$P^1$-$(L^2)_d$-p2-$(L^3)_e$-$P^3$, and -$(L^2)_c$-$P^1$-$(L^2)_d$-$P^2$-$(L^3)_e$-$P^3$-$(L^4)_f$-$P^4$ $P^1$, $p^2$, $P^3$, and $P^4$ are each independently sequences of TALL-1 modulating domains, such as those of Formulae I(a) through I(i);

$L^1$, $L^2$, $L^3$, and $L^4$ are each independently linkers; and a, b, c, d, e, and f are each independently 0 or 1, provided that at least one of a and b is 1.

Thus, compound II comprises preferred compounds of the formulae

            III and multimers thereof wherein $V^1$ is an Fc domain and is attached at the C-terminus of $A^1$;

            IV and multimers thereof wherein $V^1$ is an Fc domain and is attached at the N-terminus of $A^2$;

            V and multimers thereof wherein $V^1$ is an Fc domain and is attached at the N-terminus of -$(L^1)_c$—$P^1$; and

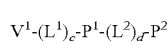            VI and multimers thereof wherein $V^1$ is an Fc domain and is attached at the N-terminus of -$L^1$-$P^1$-$L^2$-$P^2$.

Peptides. The peptides of this invention are useful as TALL-1 modulating peptides or as TALL-1 modulating domains in the molecules of formulae II through VI. Molecules of this invention comprising these peptide sequences may be prepared by methods known in the art.

Preferred peptide sequences are those of the foregoing formulae I(a) having the substituents identified below.

TABLE 1

Preferred peptide substituents

| | |
|---|---|
| Formula I (a) | $a^8$ is T;<br>$a^9$ is a basic residue (K most preferred); and<br>$a^{12}$ is a neutral hydrophobic residue (F most preferred). |
| Formula I (b) | $b^3$ is D, Q, or E;<br>$b^6$ is W or Y;<br>$b^{10}$ is T;<br>$b^{11}$ is K or R; and<br>$b^{14}$ is V or L. |
| Formula I (c) | $c^9$ is T;<br>$c^{10}$ is K or R;<br>$c^{13}$ is a I, L, or V; and<br>$c^{17}$ is A or L. |
| Formula I (d) | $d^{13}$ is T. |
| Formula I (e) | $e^{11}$ is T. |
| Formula I (f) | $f^6$ is T;<br>$f^7$ is K; and<br>$f^{10}$ is V. |
| Formula I (g) | $g^5$ is W;<br>$g^8$ is P;<br>$g^{10}$ is E; and<br>$g^{13}$ is a basic residue. |
| Formula I (h) | $h^1$ is G;<br>$h^6$ is A;<br>$h^7$ is a neutral hydrophobic residue; and<br>$h^{10}$ is an acidic residue. |
| Formula I (i) | $i^2$ is W; and<br>$i^{14}$ is W. |

Preferred peptide sequences appear in Table 2 below.

TABLE 2

Preferred TALL-1 modulating domains

| Sequence | SEQ ID NO: |
|---|---|
| PGTCFPFPWECTHA | 29 |
| WGACWPFPWECFKE | 30 |
| VPFCDLLTKHCFEA | 31 |
| GSRCKYKWDVLTKQCFHH | 32 |
| LPGCKWDLLIKQWVCDPL | 33 |
| SADCYFDILTKSDVCTSS | 34 |
| SDDCMYDQLTRMFICSNL | 35 |
| DLNCKYDELTYKEWCQFN | 36 |
| FHDCKYDLLTRQMVCHGL | 37 |
| RNHCFWDHLLKQDICPSP | 38 |
| ANQCWWDSLTKKNVCEFF | 39 |
| YKGRQMWDILTRSWVVSL | 126 |
| QDVGLWWDILTRAWMPNI | 127 |
| QNAQRVWDLLIRTWVYPQ | 128 |
| GWNEAWWDELTKIWVLEQ | 129 |
| RITCDTWDSLIKKCVPQS | 130 |
| GAIMQFWDSLTKTWLRQS | 131 |
| WLHSGWWDPLTKHWLQKV | 132 |
| SEWFFWFDPLTRAQLKFR | 133 |
| GVWFWWFDPLTKQWTQAG | 134 |
| MQCKGYYDILTKWCVTNG | 135 |
| LWSKEVWDILTKSWVSQA | 136 |
| KAAGWWFDWLTKVWVPAP | 137 |
| AYQTWFWDSLTRLWLSTT | 138 |
| SGQHFWWDLLTRSWTPST | 139 |
| LGVGQKWDPLTKQWVSRG | 140 |
| VGKMCQWDPLIKRTVCVG | 141 |
| CRQGAKFDLLTKQCLLGR | 142 |
| GQAIRHWDVLTKQWVDSQ | 143 |
| RGPCGSWDLLTKHCLDSQ | 144 |
| WQWKQQWDLLTKQMVWVG | 145 |
| PITICRKDLLTKQVVCLD | 146 |
| KTCNGKWDLLTKQCLQQA | 147 |
| KCLKGKWDLLTKQCVTEV | 148 |
| RCWNGKWDLLTKQCIHPW | 149 |
| NRDMRKWDPLIKQWIVRP | 150 |
| QAAAATWDLLTKQWLVPP | 151 |
| PEGGPKWDPLTKQFLPPV | 152 |
| QTPQKKWDLLTKQWFTRN | 153 |
| IGSPCKWDLLTKQMICQT | 154 |
| CTAAGKWDLLTKQCIQEK | 155 |
| VSQCMKWDLLTKQCLQGW | 156 |
| VWGTWKWDLLTKQYLPPQ | 157 |
| GWWEMKWDLLTKQWYRPQ | 158 |
| TAQVSKWDLLTKQWLPLA | 159 |
| QLWGTKWDLLTKQYIQIM | 160 |
| WATSQKWDLLTKQWVQNM | 161 |
| QRQCAKWDLLTKQCVLFY | 162 |
| KTTDCKWDLLTKQRICQV | 163 |
| LLCQGKWDLLTKQCLKLR | 164 |
| LMWFWKWDLLTKQLVPTF | 165 |
| QTWAWKWDLLTKQWIGPM | 166 |
| NKELLKWDLLTKQCRGRS | 167 |
| GQKDLKWDLLTKQYVRQS | 168 |
| PKPCQKWDLLTKQCLGSV | 169 |
| GQIGWKWDLLTKQWIQTR | 170 |
| VWLDWKWDLLTKQWIHPQ | 171 |

TABLE 2-continued

Preferred TALL-1 modulating domains

| Sequence | SEQ ID NO: |
|---|---|
| QEWEYKWDLLTKQWGWLR | 172 |
| HWDSWKWDLLTKQWVVQA | 173 |
| TRPLQKWDLLTKQWLRVG | 174 |
| SDQWQKWDLLTKQWFWDV | 175 |
| QQTFMKWDLLTKQWIRRH | 176 |
| QGECRKWDLLTKQCFPGQ | 177 |
| GQMGWRWDPLIKMCLGPS | 178 |
| QLDGCKWDLLTKQKVCIP | 179 |
| HGYWQKWDLLTKQWVSSE | 180 |
| HQGQCGWDLLTRIYLPCH | 181 |
| LHKACKWDLLTKQCWPMQ | 182 |
| GPPGSVWDLLTKIWIQTG | 183 |
| ITQDWRFDTLTRLWLPLR | 184 |
| QGGFAAWDVLTKMWITVP | 185 |
| GHGTPWWDALTRIWILGV | 186 |
| VWPWQKWDLLTKQFVFQD | 187 |
| WQWSWKWDLLTRQYISSS | 188 |
| NQTLWKWDLLTKQFITYM | 60 |
| PVYQGWWDTLTKLYIWDG | 61 |
| WLDGGWRDPLIKRSVQLG | 62 |
| GHQQFKWDLLTKQWVQSN | 63 |
| QRVGQFWDVLTKMFITGS | 64 |
| QAQGWSYDALIKTWIRWP | 65 |
| GWMHWKWDPLTKQALPWM | 66 |
| GHPTYKWDLLTKQWILQM | 67 |
| WNNWSLWDPLTKLWLQQN | 68 |
| WQWGWKWDLLTKQWVQQQ | 69 |
| GQMGWRWDPLTKMWLGTS | 70 |

It is noted that the known receptors for TALL-1 bear some sequence homology with preferred peptides:

(SEQ ID NOS: 33, 195, 196, and 197, respectively)
```
12-3              LPGCKWDLLIKQWVCDPL
BAFFR     MRRGPRSLRGRDAPVPTPCVPTECYDLLVRKCVDCRLL
TACI      TICNHQSQRTCAAFCRSLSCRKEQGKFYDHLLRDCISCASI
BCMA      FVSPSQEIRGRFRRMLQMAGQCSQNEYFDSLLHACPCQLRC.
```

Any peptide containing a cysteinyl residue may be cross-linked with another Cys-containing peptide, either or both of which may be linked to a vehicle. Any peptide having more than one Cys residue may form an intrapeptide disulfide bond, as well. Any of these peptides may be derivatized as described hereinafter.

Additional useful peptide sequences may result from conservative and/or non-conservative modifications of the amino acid sequences of the sequences in Table 2.

Conservative modifications will produce peptides having functional and chemical characteristics similar to those of the peptide from which such modifications are made. In contrast, substantial modifications in the functional and/or chemical characteristics of the peptides may be accomplished by selecting substitutions in the amino acid sequence that differ significantly in their effect on maintaining (a) the structure of the molecular backbone in the area of the substitution, for example, as a sheet or helical conformation, (b) the charge or hydrophobicity of the molecule at the target site, or (c) the size of the molecule.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis" (see, for example, MacLennan et al., 1998, Acta Physiol. Scand. Suppl. 643:55-67; Sasaki et al., 1998, Adv. Biophys. 35:1-24, which discuss alanine scanning mutagenesis).

Desired amino acid substitutions (whether conservative or non-conservative) can be determined by those skilled in the art at the time such substitutions are desired. For example, amino acid substitutions can be used to identify important residues of the peptide sequence, or to increase or decrease the affinity of the peptide or vehicle-peptide molecules (see preceding formulae) described herein. Exemplary amino acid substitutions are set forth in Table 3.

TABLE 3

Amino Acid Substitutions

| Original Residues | Exemplary Substitutions | Preferred Substitutions |
|---|---|---|
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4 Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

In certain embodiments, conservative amino acid substitutions also encompass non-naturally occurring amino acid residues which are typically incorporated by chemical peptide synthesis rather than by synthesis in biological systems.

As noted in the foregoing section "Definition of Terms," naturally occurring residues may be divided into classes based on common sidechain properties that may be useful for modifications of sequence. For example, non-conservative substitutions may involve the exchange of a member of one of these classes for a member from another class. Such substituted residues may be introduced into regions of the peptide that are homologous with non-human orthologs, or into the non-homologous regions of the molecule. In addition, one may also make modifications using P or G for the purpose of influencing chain orientation.

In making such modifications, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., J. Mol. Biol., 157: 105-131 (1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

A skilled artisan will be able to determine suitable variants of the polypeptide as set forth in the foregoing sequences using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of a peptide to similar peptides. With such a comparison, one can identify residues and portions of the molecules that are conserved among similar polypeptides. It will be appreciated that changes in areas of a peptide that are not conserved relative to such similar peptides would be less likely to adversely affect the biological activity and/or structure of the peptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the peptide structure.

Additionally, one skilled in the art can review structure-function studies identifying residues in similar peptides that are important for activity or structure. In view of such a comparison, one can predict the importance of amino acid residues in a peptide that correspond to amino acid residues that are important for activity or structure in similar peptides. One skilled in the art may opt for chemically similar amino acid substitutions for such predicted important amino acid residues of the peptides.

One skilled in the art can also analyze the three-dimensional structure and amino acid sequence in relation to that structure in similar polypeptides. In view of that information, one skilled in the art may predict the alignment of amino acid residues of a peptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays know to those skilled in the art. Such data could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., Curr. Op. in Biotech., 7(4): 422-427 (1996), Chou et al., Biochemistry, 13(2): 222-245 (1974); Chou et al., Biochemistry, 113(2): 211-222 (1974); Chou et al., Adv. Enzymol. Relat. Areas Mol. Biol., 47: 45-148 (1978); Chou et al., Ann. Rev. Biochem., 47: 251-276 and Chou et al., Biophys. J., 26: 367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure. See Holm et al., Nucl. Acid. Res., 27(1): 244-247 (1999). It has been suggested (Brenner et al., Curr. Op. Struct. Biol., 7(3): 369-376 (1997)) that there are a limited number of folds in a given polypeptide or protein and that once a critical number of structures have been resolved, structural prediction will gain dramatically in accuracy.

Additional methods of predicting secondary structure include "threading" (Jones, D., Curr. Opin. Struct. Biol., 7(3): 377-87 (1997); Sippl et al., Structure, 4(1): 15-9 (1996)), "profile analysis" (Bowie et al., Science, 253: 164-170 (1991); Gribskov et al., Meth. Enzym., 183: 146-159 (1990);

Gribskov et al., Proc. Nat. Acad. Sci., 84(13): 4355-8 (1987)), and "evolutionary linkage" (See Home, supra, and Brenner, supra).

Vehicles. This invention requires the presence of at least one vehicle ($V^1$) attached to a peptide through the N-terminus, C-terminus or a sidechain of one of the amino acid residues. Multiple vehicles may also be used; e.g., Fc's at each terminus or an Fc at a terminus and a PEG group at the other terminus or a sidechain. Exemplary vehicles include:

an Fc domain;
other proteins, polypeptides, or peptides capable of binding to a salvage receptor;
human serum albumin (HSA);
a leucine zipper (LZ) domain;
polyethylene glycol (PEG), including 5 kD, 20 kD, and 30 kD PEG, as well as other polymers;
dextran;

and other molecules known in the art to provide extended half-life and/or protection from proteolytic degradation or clearance.

An Fc domain is the preferred vehicle. The Fc domain may be fused to the N or C termini of the peptides or at both the N and C termini. Fusion to the N terminus is preferred.

As noted above, Fc variants are suitable vehicles within the scope of this invention. A native Fc may be extensively modified to form an Fc variant in accordance with this invention, provided binding to the salvage receptor is maintained; see, for example WO 97/34631 and WO 96/32478. In such Fc variants, one may remove one or more sites of a native Fc that provide structural features or functional activity not required by the fusion molecules of this invention. One may remove these sites by, for example, substituting or deleting residues, inserting residues into the site, or truncating portions containing the site. The inserted or substituted residues may also be altered amino acids, such as peptidomimetics or D-amino acids. Fc variants may be desirable for a number of reasons, several of which are described below. Exemplary Fc variants include molecules and sequences in which:

1. Sites involved in disulfide bond formation are removed. Such removal may avoid reaction with other cysteine-containing proteins present in the host cell used to produce the molecules of the invention. For this purpose, the cysteine-containing segment at the N-terminus may be truncated or cysteine residues may be deleted or substituted with other amino acids (e.g., alanyl, seryl). In particular, one may truncate the N-terminal 20-amino acid segment of SEQ ID NO: 2 or delete or substitute the cysteine residues at positions 7 and 10 of SEQ ID NO: 2. Even when cysteine residues are removed, the single chain Fc domains can still form a dimeric Fc domain that is held together non-covalently.
2. A native Fc is modified to make it more compatible with a selected host cell. For example, one may remove the PA sequence near the N-terminus of a typical native Fc, which may be recognized by a digestive enzyme in *E. coli* such as proline iminopeptidase. One may also add an N-terminal methionine residue, especially when the molecule is expressed recombinantly in a bacterial cell such as *E. coli*. The Fc domain of SEQ ID NO: 2 is one such Fc variant.
3. A portion of the N-terminus of a native Fc is removed to prevent N-terminal heterogeneity when expressed in a selected host cell. For this purpose, one may delete any of the first 20 amino acid residues at the N-terminus, particularly those at positions 1, 2, 3, 4 and 5.
4. One or more glycosylation sites are removed. Residues that are typically glycosylated (e.g., asparagine) may confer cytolytic response. Such residues may be deleted or substituted with unglycosylated residues (e.g., alanine).
5. Sites involved in interaction with complement, such as the Clq binding site, are removed. For example, one may delete or substitute the EKK sequence of human IgG1. Complement recruitment may not be advantageous for the molecules of this invention and so may be avoided with such an Fc variant.
6. Sites are removed that affect binding to Fc receptors other than a salvage receptor. A native Fc may have sites for interaction with certain white blood cells that are not required for the fusion molecules of the present invention and so may be removed.
7. The ADCC site is removed. ADCC sites are known in the art; see, for example, Molec. Immunol. 29 (5): 633-9 (1992) with regard to ADCC sites in IgG1. These sites, as well, are not required for the fusion molecules of the present invention and so may be removed.
8. When the native Fc is derived from a non-human antibody, the native Fc may be humanized. Typically, to humanize a native Fc, one will substitute selected residues in the non-human native Fc with residues that are normally found in human native Fc. Techniques for antibody humanization are well known in the art.

Preferred Fc variants include the following. In SEQ ID NO: 2 (FIG. 3), the leucine at position 15 may be substituted with glutamate; the glutamate at position 99, with alanine; and the lysines at positions 101 and 103, with alanines In addition, one or more tyrosine residues can be replaced by phenylalanine residues.

An alternative vehicle would be a protein, polypeptide, peptide, antibody, antibody fragment, or small molecule (e.g., a peptidomimetic compound) capable of binding to a salvage receptor. For example, one could use as a vehicle a polypeptide as described in U.S. Pat. No. 5,739,277, issued Apr. 14, 1998 to Presta et al. Peptides could also be selected by phage display or RNA-peptide screening for binding to the FcRn salvage receptor. Such salvage receptor-binding compounds are also included within the meaning of "vehicle" and are within the scope of this invention. Such vehicles should be selected for increased half-life (e.g., by avoiding sequences recognized by proteases) and decreased immunogenicity (e.g., by favoring non-immunogenic sequences, as discovered in antibody humanization).

As noted above, polymer vehicles may also be used for $V^1$. Various means for attaching chemical moieties useful as vehicles are currently available, see, e.g., Patent Cooperation Treaty ("PCT") International Publication No. WO 96/11953, entitled "N-Terminally Chemically Modified Protein Compositions and Methods," herein incorporated by reference in its entirety. This PCT publication discloses, among other things, the selective attachment of water soluble polymers to the N-terminus of proteins.

A preferred polymer vehicle is polyethylene glycol (PEG). The PEG group may be of any convenient molecular weight and may be linear or branched. The average molecular weight of the PEG will preferably range from about 2 kiloDalton ("kD") to about 100 kD, more preferably from about 5 kD to about 50 kD, most preferably from about 5 kD to about 10 kD. The PEG groups will generally be attached to the compounds of the invention via acylation or reductive alkylation through a reactive group on the PEG moiety (e.g., an aldehyde, amino, thiol, or ester group) to a reactive group on the inventive compound (e.g., an aldehyde, amino, or ester group).

A useful strategy for the PEGylation of synthetic peptides consists of combining, through forming a conjugate linkage in solution, a peptide and a PEG moiety, each bearing a special functionality that is mutually reactive toward the other. The peptides can be easily prepared with conventional solid phase synthesis. The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of water soluble polymer which may be used for protein modification. Dextrans are polysaccharide polymers comprised of individual subunits of glucose predominantly linked by α1-6 linkages. The dextran itself is available in many molecular weight ranges, and is readily available in molecular weights from about 1 kD to about 70 kD. Dextran is a suitable water soluble polymer for use in the present invention as a vehicle by itself or in combination with another vehicle (e.g., Fc). See, for example, WO 96/11953 and WO 96/05309. The use of dextran conjugated to therapeutic or diagnostic immunoglobulin has been reported; see, for example, European Patent Publication No. 0 315 456, which is hereby incorporated by reference in its entirety. Dextran of about 1 kD to about 20 kD is preferred when dextran is used as a vehicle in accordance with the present invention.

Linkers. Any "linker" group is optional. When present, its chemical structure is not critical, since it serves primarily as a spacer. The linker is preferably made up of amino acids linked together by peptide bonds. Thus, in preferred embodiments, the linker is made up of from 1 to 30 amino acids linked by peptide bonds, wherein the amino acids are selected from the 20 naturally occurring amino acids. Some of these amino acids may be glycosylated, as is well understood by those in the art. In a more preferred embodiment, the 1 to 20 amino acids are selected from glycine, alanine, proline, asparagine, glutamine, and lysine. Even more preferably, a linker is made up of a majority of amino acids that are sterically unhindered, such as glycine and alanine. Thus, preferred linkers are polyglycines (particularly (Gly)$_4$, (Gly)$_5$), poly(Gly-Ala), and polyalanines. Other specific examples of linkers are:

| | |
|---|---|
| (Gly)$_3$Lys(Gly)$_4$; | (SEQ ID NO: 40) |
| (Gly)$_3$AsnGlySer(Gly)$_2$; | (SEQ ID NO: 41) |
| (Gly)$_3$Cys(Gly)$_4$; and | (SEQ ID NO: 42) |
| GlyProAsnGlyGly. | (SEQ ID NO: 43) |

To explain the above nomenclature, for example, (Gly)$_3$Lys (Gly)$_4$ means Gly-Gly-Gly-Lys-Gly-Gly-Gly-Gly (SEQ ID NO: 40). Combinations of Gly and Ala are also preferred. The linkers shown here are exemplary; linkers within the scope of this invention may be much longer and may include other residues.

Preferred linkers are amino acid linkers comprising greater than 5 amino acids, with suitable linkers having up to about 500 amino acids selected from glycine, alanine, proline, asparagine, glutamine, lysine, threonine, serine or aspartate. Linkers of about 20 to 50 amino acids are most preferred. One group of preferred linkers are those of the formulae GSGSATGGSGSTASSGSGSATx$^1$x$^2$ (SEQ ID NO: 193)

and

GSGSATGGSGSTASSGSGSATx$^1$x$^2$GSGSATGGSGSTASSGSGSATx$^3$x$^4$ (SEQ ID NO: 194)

wherein x$^1$ and x$^3$ are each independently basic or hydrophobic residues and x$^2$ and x$^4$ are each independently hydrophobic residues. Specific preferred linkers are:

GSGSATGGSGSTASSGSGSATHM (SEQ ID NO: 59)

GSGSATGGSGSTASSGSGSATGM (SEQ ID NO: 190)

GSGSATGGSGSTASSGSGSATGS, (SEQ ID NO: 191)

and

GSGSATGGSGSTASSGSGSATHMGSGSATGGSGSTASSGSGSATHM. (SEQ ID NO: 192)

Non-peptide linkers are also possible. For example, alkyl linkers such as —NH—(CH$_2$)$_s$—C(O)—, wherein s=2-20 could be used. These alkyl linkers may further be substituted by any non-sterically hindering group such as lower alkyl (e.g., C$_1$-C$_6$) lower acyl, halogen (e.g., Cl, Br), CN, NH$_2$, phenyl, etc. An exemplary non-peptide linker is a PEG linker,

VII

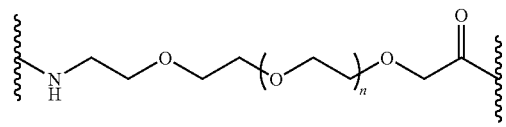

wherein n is such that the linker has a molecular weight of 100 to 5000 kD, preferably 100 to 500 kD. The peptide linkers may be altered to form derivatives in the same manner as described above.

Derivatives. The inventors also contemplate derivatizing the peptide and/or vehicle portion of the compounds. Such derivatives may improve the solubility, absorption, biological half life, and the like of the compounds. The moieties may alternatively eliminate or attenuate any undesirable side-effect of the compounds and the like. Exemplary derivatives include compounds in which:

1. The compound or some portion thereof is cyclic. For example, the peptide portion may be modified to contain two or more Cys residues (e.g., in the linker), which could cyclize by disulfide bond formation.

2. The compound is cross-linked or is rendered capable of cross-linking between molecules. For example, the peptide portion may be modified to contain one Cys residue and thereby be able to form an intermolecular disulfide bond with a like molecule. The compound may also be cross-linked through its C-terminus, as in the molecule shown below.

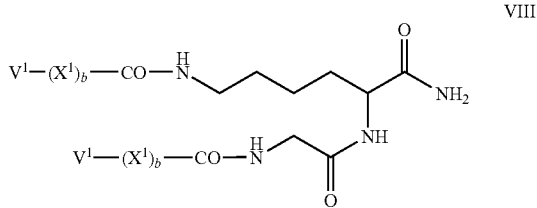

VIII

In Formula VIII, each "$V^1$" may represent typically one strand of the Fc domain.

3. One or more peptidyl [—C(O)NR—] linkages (bonds) is replaced by a non-peptidyl linkage. Exemplary non-peptidyl linkages are —$CH_2$— carbamate [—$CH_2$—OC(O)NR—], phosphonate, —$CH_2$-sulfonamide [—$CH_2$—S(O)$_2$NR-1, urea [—NHC(O)NH—], —$CH_2$-secondary amine, and alkylated peptide [—C(O)NR$^6$— wherein R$^6$ is lower alkyl].

4. The N-terminus is derivatized. Typically, the N-terminus may be acylated or modified to a substituted amine. Exemplary N-terminal derivative groups include —NRR$^1$ (other than —NH$_2$), —NRC(O)R$^1$, —NRC(O)OR$^1$, —NRS(O)$_2$R$^1$, —NHC(O)NHR$^1$, succinimide, or benzyloxycarbonyl-NH— (CBZ—NH—), wherein R and R$^1$ are each independently hydrogen or lower alkyl and wherein the phenyl ring may be substituted with 1 to 3 substituents selected from the group consisting of $C_1$-$C_4$ alkyl, $C_1$-$C_4$ alkoxy, chloro, and bromo.

5. The free C-terminus is derivatized. Typically, the C-terminus is esterified or amidated. Exemplary C-terminal derivative groups include, for example, —C(O)R$^2$ wherein R$^2$ is lower alkoxy or —NR$^3$R$^4$ wherein R$^3$ and R$^4$ are independently hydrogen or $C_1$-$C_8$ alkyl (preferably $C_1$-$C_4$ alkyl).

6. A disulfide bond is replaced with another, preferably more stable, cross-linking moiety (e.g., an alkylene). See, e.g., Bhatnagar et al. (1996), J. Med. Chem. 39: 3814-9; Alberts et al. (1993) Thirteenth Am. Pep. Symp., 357-9.

7. One or more individual amino acid residues is modified. Various derivatizing agents are known to react specifically with selected sidechains or terminal residues, as described in detail below.

Lysinyl residues and amino terminal residues may be reacted with succinic or other carboxylic acid anhydrides, which reverse the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with any one or combination of several conventional reagents, including phenylglyoxal, 2,3-butanedione, 1,2-cyclohexanedione, and ninhydrin. Derivatization of arginyl residues requires that the reaction be performed in alkaline conditions because of the high pKa of the guanidine functional group. Furthermore, these reagents may react with the groups of lysine as well as the arginine epsilon-amino group.

Specific modification of tyrosyl residues has been studied extensively, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl sidechain groups (aspartyl or glutamyl) may be selectively modified by reaction with carbodiimides (R'—N=C=N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues may be converted to asparaginyl and glutaminyl residues by reaction with ammonium ions.

Glutaminyl and asparaginyl residues may be deamidated to the corresponding glutamyl and aspartyl residues. Alternatively, these residues are deamidated under mildly acidic conditions. Either form of these residues falls within the scope of this invention.

Cysteinyl residues can be replaced by amino acid residues or other moieties either to eliminate disulfide bonding or, conversely, to stabilize cross-linking See, e.g., Bhatnagar et al. (1996), J. Med. Chem. 39: 3814-9.

Derivatization with bifunctional agents is useful for cross-linking the peptides or their functional derivatives to a water-insoluble support matrix or to other macromolecular vehicles. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming cross-links in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Carbohydrate (oligosaccharide) groups may conveniently be attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids other than proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). However, such sites may further be glycosylated by synthetic or semi-synthetic procedures known in the art.

Other possible modifications include hydroxylation of proline and lysine, phosphorylation of hydroxyl groups of seryl or threonyl residues, oxidation of the sulfur atom in Cys, methylation of the alpha-amino groups of lysine, arginine, and histidine side chains. Creighton, Proteins: Structure and Molecule Properties (W.H. Freeman & Co., San Francisco), pp. 79-86 (1983).

Compounds of the present invention may be changed at the DNA level, as well. The DNA sequence of any portion of the compound may be changed to codons more compatible with the chosen host cell. For E. coli, which is the preferred host cell, optimized codons are known in the art. Codons may be substituted to eliminate restriction sites or to include silent restriction sites, which may aid in processing of the DNA in the selected host cell. The vehicle, linker and peptide DNA sequences may be modified to include any of the foregoing sequence changes.

Methods of Making

The compounds of this invention largely may be made in transformed host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidate method. Also, a combination of these techniques could be used.

The invention also includes a vector capable of expressing the peptides in an appropriate host. The vector comprises the DNA molecule that codes for the peptides operatively linked to appropriate expression control sequences. Methods of effecting this operative linking, either before or after the DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be used in the practice of this invention. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as *E. coli* sp.), yeast (such as *Saccharomyces* sp.) and other fungi, insects, plants, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the peptides are purified from culture by methods well known in the art.

The compounds may also be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. Solid phase synthesis is the preferred technique of making individual peptides since it is the most cost-effective method of making small peptides. Compounds that contain derivatized peptides or which contain non-peptide groups may be synthesized by well-known organic chemistry techniques.

Uses of the Compounds

Compounds of this invention may be particularly useful in treatment of B-cell mediated autoimmune diseases. In particular, the compounds of this invention may be useful in treating, preventing, ameliorating, diagnosing or prognosing lupus, including systemic lupus erythematosus (SLE), and lupus-associated diseases and conditions. Other preferred indications include B-cell mediated cancers, including B-cell lymphoma.

The compounds of this invention can also be used to treat inflammatory conditions of the joints. Inflammatory conditions of a joint are chronic joint diseases that afflict and disable, to varying degrees, millions of people worldwide. Rheumatoid arthritis is a disease of articular joints in which the cartilage and bone are slowly eroded away by a proliferative, invasive connective tissue called pannus, which is derived from the synovial membrane. The disease may involve peri-articular structures such as bursae, tendon sheaths and tendons as well as extra-articular tissues such as the subcutis, cardiovascular system, lungs, spleen, lymph nodes, skeletal muscles, nervous system (central and peripheral) and eyes (Silberberg (1985), Anderson's Pathology, Kissane (ed.), II:1828). Osteoarthritis is a common joint disease characterized by degenerative changes in articular cartilage and reactive proliferation of bone and cartilage around the joint. Osteoarthritis is a cell-mediated active process that may result from the inappropriate response of chondrocytes to catabolic and anabolic stimuli. Changes in some matrix molecules of articular cartilage reportedly occur in early osteoarthritis (Thonar et al. (1993), Rheumatic disease clinics of North America, Moskowitz (ed.), 19:635-657 and Shinmei et al. (1992), Arthritis Rheum., 35:1304-1308). TALL-1, TALL-1R and modulators thereof are believed to be useful in the treatment of these and related conditions.

Compounds of this invention may also be useful in treatment of a number of additional diseases and disorders, including:

acute pancreatitis;
ALS;
Alzheimer's disease;
asthma;
atherosclerosis;
autoimmune hemolytic anemia;
cancer, particularly cancers related to B cells;
cachexia/anorexia;
chronic fatigue syndrome;
cirrhosis (e.g., primary biliary cirrhosis);
diabetes (e.g., insulin diabetes);
fever;
glomerulonephritis, including IgA glomerulonephritis and primary glomerulonephritis;
Goodpasture's syndrome;
Guillain-Barre syndrome;
graft versus host disease;
Hashimoto's thyroiditis;
hemorrhagic shock;
hyperalgesia;
inflammatory bowel disease;
inflammatory conditions of a joint, including osteoarthritis, psoriatic arthritis and rheumatoid arthritis;
inflammatory conditions resulting from strain, sprain, cartilage damage, trauma, orthopedic surgery, infection or other disease processes;
insulin-dependent diabetes mellitus;
ischemic injury, including cerebral ischemia (e.g., brain injury as a result of trauma, epilepsy, hemorrhage or stroke, each of which may lead to neurodegeneration);
learning impairment;
lung diseases (e.g., ARDS);
multiple myeloma;

multiple sclerosis;
Myasthenia gravis;
myelogenous (e.g., AML and CML) and other leukemias;
myopathies (e.g., muscle protein metabolism, esp. in sepsis);
neurotoxicity (e.g., as induced by HIV);
osteoporosis;
pain;
Parkinson's disease;
Pemphigus;
polymyositis/dermatomyositis;
pulmonary inflammation, including autoimmune pulmonary inflammation;
pre-term labor;
psoriasis;
Reiter's disease;
reperfusion injury;
septic shock;
side effects from radiation therapy;
Sjogren's syndrome;
sleep disturbance;
temporal mandibular joint disease;
thrombocytopenia, including idiopathic thrombocytopenia and autoimmune neonatal thrombocytopenia;
tumor metastasis;
uveitis; and
vasculitis.

Compounds of this invention may be administered alone or in combination with a therapeutically effective amount of other drugs, including analgesic agents, disease-modifying anti-rheumatic drugs (DMARDs), non-steroidal anti-inflammatory drugs (NSAIDs), and any immune and/or inflammatory modulators. Thus, compounds of this invention may be administered with:

Modulators of other members of the TNF/TNF receptor family, including TNF antagonists, such as etanercept (Enbrel™), sTNF-RI, onercept, D2E7, and Remicade™.
Nerve growth factor (NGF) modulators.
IL-1 inhibitors, including IL-1ra molecules such as anakinra and more recently discovered IL-1ra-like molecules such as IL-1Hy1 and IL-1Hy2; IL-1 "trap" molecules as described in U.S. Pat. No. 5,844,099, issued Dec. 1, 1998; IL-1 antibodies; solubilized IL-1 receptor, and the like.
IL-6 inhibitors (e.g., antibodies to IL-6).
IL-8 inhibitors (e.g., antibodies to IL-8).
IL-18 inhibitors (e.g., IL-18 binding protein, solubilized IL-18 receptor, or IL-18 antibodies).
Interleukin-1 converting enzyme (ICE) modulators.
insulin-like growth factors (IGF-1, IGF-2) and modulators thereof.
Transforming growth factor-β (TGF-β), TGF-β family members, and TGF-β modulators.
Fibroblast growth factors FGF-1 to FGF-10, and FGF modulators.
Osteoprotegerin (OPG), OPG analogues, osteoprotective agents, and antibodies to OPG-ligand (OPG-L).
bone anabolic agents, such as parathyroid hormone (PTH), PTH fragments, and molecules incorporating PTH fragments (e.g., PTH (1-34)-Fc).
PAF antagonists.
Keratinocyte growth factor (KGF), KGF-related molecules (e.g., KGF-2), and KGF modulators.
COX-2 inhibitors, such as Celebrex™ and Vioxx™.
Prostaglandin analogs (e.g., E series prostaglandins).
Matrix metalloproteinase (MMP) modulators.
Nitric oxide synthase (NOS) modulators, including modulators of inducible NOS.
Modulators of glucocorticoid receptor.
Modulators of glutamate receptor.
Modulators of lipopolysaccharide (LPS) levels.
Anti-cancer agents, including inhibitors of oncogenes (e.g., fos, jun) and interferon.
Noradrenaline and modulators and mimetics thereof.

Pharmaceutical Compositions

In General. The present invention also provides methods of using pharmaceutical compositions of the inventive compounds. Such pharmaceutical compositions may be for administration for injection, or for oral, pulmonary, nasal, transdermal or other forms of administration. In general, the invention encompasses pharmaceutical compositions comprising effective amounts of a compound of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hyaluronic acid may also be used, and this may have the effect of promoting sustained duration in the circulation. Such compositions may influence the physical state, stability, rate of in vivo release, and rate of in vivo clearance of the present proteins and derivatives. See, e.g., *Remington's Pharmaceutical Sciences,* 18th Ed. (1990, Mack Publishing Co., Easton, Pa. 18042) pages 1435-1712 which are herein incorporated by reference in their entirety. The compositions may be prepared in liquid form, or may be in dried powder, such as lyophilized form. Implantable sustained release formulations are also contemplated, as are transdermal formulations.

Oral dosage forms. Contemplated for use herein are oral solid dosage forms, which are described generally in Chapter 89 of Remington's Pharmaceutical Sciences (1990), 18th Ed., Mack Publishing Co. Easton Pa. 18042, which is herein incorporated by reference in its entirety. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given in Chapter 10 of Marshall, K., Modern Pharmaceutics (1979), edited by G. S. Banker and C. T. Rhodes, herein incorporated by reference in its entirety. In general, the formulation will include the inventive compound, and inert ingredients which allow for protection against the stomach environment, and release of the biologically active material in the intestine.

Also specifically contemplated are oral dosage forms of the above inventive compounds. If necessary, the compounds may be chemically modified so that oral delivery is efficacious. Generally, the chemical modification contemplated is the attachment of at least one moiety to the compound molecule itself, where said moiety permits (a) inhibition of proteolysis; and (b) uptake into the blood stream from the stomach or intestine. Also desired is the increase in overall stability of the compound and increase in circulation time in the body. Moieties useful as covalently attached vehicles in this invention may also be used for this purpose. Examples of such moieties include: PEG, copolymers of ethylene glycol and propylene glycol, carboxymethyl cellulose, dextran, polyvinyl alcohol, polyvinyl pyrrolidone and polyproline. See, for example, Abuchowski and Davis, Soluble Polymer-Enzyme Adducts, Enzymes as Drugs (1981), Hocenberg and Roberts, eds., Wiley-Interscience, New York, N.Y., pp. 367-83; Newmark, et al. (1982), I. Appl. Biochem. 4:185-9. Other polymers that could be used are poly-1,3-dioxolane and poly-1,3,6-tioxocane. Preferred for pharmaceutical usage, as indicated above, are PEG moieties.

For oral delivery dosage forms, it is also possible to use a salt of a modified aliphatic amino acid, such as sodium N-(8-[2-hydroxybenzoyl]amino) caprylate (SNAC), as a carrier to enhance absorption of the therapeutic compounds of this invention. The clinical efficacy of a heparin formulation using SNAC has been demonstrated in a Phase II trial conducted by Emisphere Technologies. See U.S. Pat. No. 5,792,451, "Oral drug delivery composition and methods".

The compounds of this invention can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the compound of the invention with an inert material. These diluents could include carbohydrates, especially mannitol, α-lactose, anhydrous lactose, cellulose, sucrose, modified dextrans and starch. Certain inorganic salts may also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the compound of this invention into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethonium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives may also be included in the formulation to enhance uptake of the compound. Additives potentially having this property are for instance the fatty acids oleic acid, linoleic acid and linolenic acid.

Controlled release formulation may be desirable. The compound of this invention could be incorporated into an inert matrix which permits release by either diffusion or leaching mechanisms; e.g., gums. Slowly degenerating matrices may also be incorporated into the formulation, e.g., alginates, polysaccharides. Another form of a controlled release of the compounds of this invention is by a method based on the Oros therapeutic system (Alza Corp.), i.e., the drug is enclosed in a semipermeable membrane which allows water to enter and push drug out through a single small opening due to osmotic effects. Some enteric coatings also have a delayed release effect.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid. A mix of materials might be used to provide the optimum film coating. Film coating may be carried out in a pan coater or in a fluidized bed or by compression coating.

Pulmonary delivery forms. Also contemplated herein is pulmonary delivery of the present protein (or derivatives thereof). The protein (or derivative) is delivered to the lungs of a mammal while inhaling and traverses across the lung epithelial lining to the blood stream. (Other reports of this include Adjei et al., Pharma. Res. (1990) 7: 565-9; Adjei et al. (1990), Internatl. J. Pharmaceutics 63: 135-44 (leuprolide acetate); Braquet et al. (1989), J. Cardiovasc. Pharmacol. 13 (suppl.5): s.143-146 (endothelin-1); Hubbard et al. (1989), Annals Int. Med. 3: 206-12 (α1-antitrypsin); Smith et al. (1989), J. Gin. Invest. 84: 1145-6 (α1-proteinase); Oswein et al. (March 1990), "Aerosolization of Proteins", Proc. Symp. Resp. Drug Delivery II, Keystone, Colo. (recombinant human growth hormone); Debs et al. (1988), I. Immunol. 140: 3482-8 (interferon-γ and tumor necrosis factor α) and Platz et al., U.S. Pat. No. 5,284,656 (granulocyte colony stimulating factor).

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the inventive compound. Typically, each formulation is specific to the type of device employed and may involve the use of an appropriate propellant material, in addition to diluents, adjuvants and/or carriers useful in therapy.

The inventive compound should most advantageously be prepared in particulate form with an average particle size of less than 10 μm (or microns), most preferably 0.5 to 5 μm, for most effective delivery to the distal lung.

Pharmaceutically acceptable carriers include carbohydrates such as trehalose, mannitol, xylitol, sucrose, lactose, and sorbitol. Other ingredients for use in formulations may include DPPC, DOPE, DSPC and DOPC. Natural or synthetic surfactants may be used. PEG may be used (even apart from its use in derivatizing the protein or analog). Dextrans, such as cyclodextran, may be used. Bile salts and other related enhancers may be used. Cellulose and cellulose derivatives may be used. Amino acids may be used, such as use in a buffer formulation.

Also, the use of liposomes, microcapsules or microspheres, inclusion complexes, or other types of carriers is contemplated.

Formulations suitable for use with a nebulizer, either jet or ultrasonic, will typically comprise the inventive compound dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the inventive compound suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the inventive compound and may also include a bulking agent, such as lactose, sorbitol, sucrose, mannitol, trehalose, or xylitol in amounts which facilitate dispersal of the powder from the device, e.g., 50 to 90% by weight of the formulation.

Nasal delivery forms. Nasal delivery of the inventive compound is also contemplated. Nasal delivery allows the passage of the protein to the blood stream directly after administering the therapeutic product to the nose, without the necessity for deposition of the product in the lung. Formulations for nasal delivery include those with dextran or cyclodextran. Delivery via transport across other mucous membranes is also contemplated.

Dosages. The dosage regimen involved in a method for treating the above-described conditions will be determined by the attending physician, considering various factors which modify the action of drugs, e.g. the age, condition, body weight, sex and diet of the patient, the severity of any infection, time of administration and other clinical factors. Generally, the daily regimen should be in the range of 0.1-1000 micrograms of the inventive compound per kilogram of body weight, preferably 0.1-150 micrograms per kilogram.

Specific Preferred Embodiments

The inventors have determined preferred structures for the preferred peptides listed in Table 4 below. The symbol "Λ" may be any of the linkers described herein or may simply represent a normal peptide bond (i.e., so that no linker is present). Tandem repeats and linkers are shown separated by dashes for clarity.

TABLE 4

Preferred embodiments

| Sequence/structure | SEQ ID NO: |
|---|---|
| LPGCKWDLLIKQWVCDPL-Λ-V$^1$ | 44 |
| V$^1$-Λ-LPGCKWDLLIKQWVCDPL | 45 |
| LPGCKWDLLIKQWVCDPL-Λ-LPGCKWDLLIKQWVCDPL-Λ-V$^1$ | 46 |
| V$^1$-Λ-LPGCKWDLLIKQWVCDPL-Λ-LPGCKWDLLIKQWVCDPL | 47 |
| SADCYFDILTKSDVCTSS-Λ-V$^1$ | 48 |
| V$^1$-Λ-SADCYFDILTKSDVCTSS | 49 |
| SADCYFDILTKSDVTSS-Λ-SADCYFDILTKSDVTSS-Λ-V$^1$ | 50 |
| V$^1$-Λ-SADCYFDILTKSDVTSS-Λ-SADCYFDILTKSDVTSS | 51 |
| FHDCKWDLLTKQWVCHGL-Λ-V$^1$ | 52 |
| V$^1$-Λ-FHDCKWDLLTKQWVCHGL | 53 |
| FHDCKWDLLTKQWVCHGL-Λ-FHDCKWDLLTKQWVCHGL-Λ-V$^1$ | 54 |
| V$^1$-Λ-FHDCKWDLLTKQWVCHGL-Λ-FHDCKWDLLTKQWVCHGL | 55 |

"V$^1$" is an Fc domain as defined previously herein. In addition to those listed in Table 4, the inventors further contemplate heterodimers in which each strand of an Fc dimer is linked to a different peptide sequence; for example, wherein each Fc is linked to a different sequence selected from Table 2.

All of the compounds of this invention can be prepared by methods described in PCT appl. no. WO 99/25044.

The invention will now be further described by the following working examples, which are illustrative rather than limiting.

EXAMPLE 1

Peptides

Peptide Phage Display

1. Magnetic Bead Preparation

A. Fc-TALL-1 immobilization on magnetic beads

The recombinant Fc-TALL-1 protein was immobilized on the Protein A Dynabeads (Dynal) at a concentration of 8 µg of Fc-TALL-1 per 100 µl of the bead stock from the manufacturer. By drawing the beads to one side of a tube using a magnet and pipetting away the liquid, the beads were washed twice with the phosphate buffer saline (PBS) and resuspended in PBS. The Fc-TALL-1 protein was added to the washed beads at the above concentration and incubated with rotation for 1 hour at room temperature. The Fc-TALL-1 coated beads were then blocked by adding bovine serum albumin (BSA) to 1% final concentration and incubating overnight at 4° C. with rotation. The resulting Fe-TALL-1 coated beads were then washed twice with PBST (PBS with 0.05% Tween-20) before being subjected to the selection procedures.

B. Negative Selection Bead Preparation

Additional beads were also prepared for negative selections. For each panning condition, 250 µl of the bead stock from the manufacturer was subjected to the above procedure (section 1A) except that the incubation step with Fc-TALL-1 was omitted. In the last washing step, the beads were divided into five 50 µl aliquots.

2. Selection of TALL-1 Binding Phage

A. Overall Strategy

Two filamentous phage libraries, TN8-IX ($5 \times 10^9$ independent transformants) and TN12-I ($1.4 \times 10^9$ independent transformants) (Dyax Corp.), were used to select for TALL-1 binding phage. Each library was subjected to either pH 2 elution or 'bead elution' (section 2E). Therefore, four different panning conditions were carried out for the TALL-1 project (TN8-IX using the pH2 elution method, TN8-IX using the bead elution method, TN12-I the using pH2 elution method, and TN 12-I using the bead elution method). Three rounds of selection were performed for each condition.

B. Negative Selection

For each panning condition, about 100 random library equivalent ($5 \times 10^{11}$ pfu for TN8-IX and $1.4 \times 10^{11}$ pfu for TN12-I) was aliquoted from the library stock and diluted to 300 µl with PBST. After the last washing liquid was drawn out from the first 50 µl aliquot of the beads prepared for negative selections (section 1B), the 300 µl diluted library stock was added to the beads. The resulting mixture was incubated for 10 minutes at room temperature with rotation. The phage supernatant was drawn out using the magnet and added to the second 50 µl aliquot for another negative selection step. In this way, five negative selection steps were performed.

C. Selection Using the Fc-TALL-1 Protein Coated Beads

The phage supernatant after the last negative selection step (section 1B) was added to the Fc-TALL-1 coated beads after the last washing step (section 1A). This mixture was incubated with rotation for two hours at room temperature, allowing specific phage to bind to the target protein. After the supernatant is discarded, the beads were washed seven times with PBST.

D. pH2 Elution of Bound Phage

After the last washing step (section 2C), the bound phages were eluted from the magnetic beads by adding 200 µl of CBST (50 mM sodium citrate, 150 mM sodium chloride, 0.05% Tween-20, pH2). After 5 minute incubation at room temperature, the liquid containing the eluted phage were drawn out and transferred to another tube. The elution step was repeated again by adding 200 µl of CBST and incubating for 5 minutes. The liquids from two elution steps were added together, and 100 µl of 2 M Tris solution (pH 8) was added to neutralize the pH. 500 µl of Min A Salts solution (60 mM $K_2HPO_4$, 33 mM $KH_2PO_4$, 7.6 mM $(NH_4)SO_4$, and 1.7 mM sodium citrate) was added to make the final volume to 1 ml.

E. 'Bead Elution'

After the final washing liquid was drawn out (section 2C), 1 ml of Min A salts solution was added to the beads. This bead mixture was added directly to a concentrated bacteria sample for infection (section 3A and 3B).

3. Amplification

A. Preparation of Plating Cells

Fresh *E. coli.* (XL-1 Blue MRF') culture was grown to $OD_{600}=0.5$ in LB media containing 12.5 µg/ml tetracycline. For each panning condition, 20 ml of this culture was chilled on ice and centrifuged. The bacteria pellet was resuspended in 1 ml of the Min A Salts solution.

B. Transduction

Each mixture from different elution methods (section 2D and 2E) was added to a concentrated bacteria sample (section 3A) and incubated at 37° C. for 15 minutes. 2 ml of NZCYM media (2XNZCYM, 50 µg/ml ampicillin) was added to each mixture and incubated at room temperature for 15 minutes. The resulting 4 ml solution was plated on a large NZCYM agar plate containing 50 µg/ml ampicillin and incubated overnight at 37° C.

C. Phage Harvesting

Each of the bacteria/phage mixture that was grown overnight on a large NZCYM agar plate (section 3B) was scraped off in 35 ml of LB media, and the agar plate was further rinsed with additional 35 ml of LB media. The resulting bacteria/phage mixture in LB media was centrifuged to pellet the bacteria away. 50 ml the of the phage supernatant was transferred to a fresh tube, and 12.5 ml of PEG solution (20% PEG8000, 3.5M ammonium acetate) was added and incubated on ice for 2 hours to precipitate phages. Precipitated phages were centrifuged down and resuspended in 6 ml of the phage resuspension buffer (250 mM NaCl, 100 mM Tris pH8, 1 mM EDTA). This phage solution was further purified by centrifuging away the remaining bacteria and precipitating the phage for the second time by adding 1.5 ml of the PEG solution. After a centrifugation step, the phage pellet was resuspended in 400 IA of PBS. This solution was subjected to a final centrifugation to rid of remaining bacteria debris. The resulting phage preparation was titered by a standard plaque formation assay (Molecular Cloning, Maniatis et al $3^{rd}$ Edition).

4. Two More Rounds of Selection and Amplification.

In the second round, the amplified phage ($10^{10}$ pfu) from the first round (section 3C) was used as the input phage to perform the selection and amplification steps (sections 2 and 3). The amplified phage ($10^{10}$ pfu) from the $2^{nd}$ round in turn was used as the input phage to perform $3^{rd}$ round of selection and amplification (sections 2 and 3). After the elution steps (sections 2D and 2E) of the $3^{rd}$ round, a small fraction of the eluted phage was plated out as in the plaque formation assay (section 3C). Individual plaques were picked and placed into 96 well microtiter plates containing 100 µl of TE buffer in each well. These master plates were incubated in a 37° C. incubator for 1 hour to allow phages to elute into the TE buffer.

5. Clonal Analysis (Phage ELISA and Sequencing)

The phage clones were analyzed by phage ELISA and sequencing methods. The sequences were ranked based on the combined results from these two assays.

A. Phage ELISA

An XL-1 Blue MRF' culture was grown until $OD_{600}$ reaches 0.5. 30 μl of this culture was aliquoted into each well of a 96 well microtiter plate. 10 μl of eluted phage (section 4) was added to each well and allowed to infect bacteria for 15 min at room temperature. 130 μl of LB media containing 12.5 μl of tetracycline and 50 μg/ml of ampicillin was added to each well. The microtiter plate was then incubated overnight at 37° C. The recombinant TALL-1 protein (1 μg/ml in PBS) was allowed to coat onto the 96-well Maxisorp plates (NUNC) overnight and 4° C. As a control, the recombinant Fc-Trail protein was coated onto a separate Maxisorp plate at the same molar concentration as the TALL-1 protein.

On the following day, liquids in the protein coated Maxisorp plates were discarded, and each well was blocked with 300 μl of 2% BSA solution at 37° C. for one hour. The BSA solution was discarded, and the wells were washed three times with the PBST solution. After the last washing step, 50 μl of PBST was added to each well of the protein coated Maxisorp plates. Each of the 50 μl overnight cultures in the 96 well microtiter plate was transferred to the corresponding wells of the TALL-1 coated plates as well as the control Fc-Trail coated plates. The 100 μl mixtures in the two kinds of plates were incubated for 1 hour at room temperature. The liquid was discarded from the Maxisorp plates, and the wells were washed five times with PBST. The HRP-conjugated anti-M13 antibody (Pharmacia) was diluted to 1:7,500, and 100 μl of the diluted solution was added to each well of the Maxisorp plates for 1 hour incubation at room temperature. The liquid was again discarded and the wells were washed seven times with PBST. 100 μl of tetramethylbenzidine (TMB) substrate (Sigma) was added to each well for the color reaction to develop, and the reaction was stopped with 50 μl of the 5 N $H_2SO_4$ solution. The $OD_{450}$ was read on a plate reader (Molecular Devices).

B. Sequencing of the Phage Clones.

For each phage clone, the sequencing template was prepared by a PCR method. The following oligonucleotide pair was used to amplify about 500 nucleotide fragment:

```
                                           (SEQ ID NO: 56)
primer #1 (5'-CGGCGCAACTATCGGTATCAAGCTG-3')
and
                                           (SEQ ID NO: 57)
primer #2 (5'-CATGTACCGTAACACTGAGTTTCGTC-3').
```

The following mixture was prepared for each clone.

| Reagents | volume (μL)/tube |
|---|---|
| $dH_2O$ | 26.25 |
| 50% glycerol | 10 |
| 10B PCR Buffer (w/o $MgCl_2$) | 5 |
| 25 mM $MgCl_2$ | 4 |
| 10 mM dNTP mix | 1 |
| 100 μM primer 1 | 0.25 |
| 100 μM primer 2 | 0.25 |
| Taq polymerase | 0.25 |
| Phage in TE (section 4) | 3 |
| Final reaction volume | 50 |

The thermocycler (GeneAmp PCR System 9700, Applied Biosystems) was used to run the following program: 94° C. for 5 min; [94° C. for 30 sec, 55° C. for 30 sec, 72° C. for 45 sec.]×30 cycles; 72° C. for 7 min; cool to 4° C. The PCR product was checked by running 5 μl of each PCR reaction on a 1% agarose gel. The PCR product in the remaining 45 μl from each reaction was cleaned up using the QIAquick Multiwell PCR Purification kit (Qiagen), following the manufacturer's protocol. The resulting product was then sequenced using the ABI 377 Sequencer (Perkin-Elmer) following the manufacturer recommended protocol.

6. Sequence Ranking and Consensus Sequence Determination

A. Sequence Ranking

The peptide sequences that were translated from variable nucleotide sequences (section 5B) were correlated to ELISA data. The clones that showed high $OD_{450}$ in the TALL-1 coated wells and low $OD_{450}$ in the Fc-Trail coated wells were considered more important. The sequences that occur multiple times were also considered important. Candidate sequences were chosen based on these criteria for further analysis as peptides or peptibodies. Five and nine candidate peptide sequences were selected from the TN8-IX and TN12-I libraries, respectively.

B. Consensus Sequence Determination

The majority of sequences selected from the TN12-I library contained a very conserved DBL motif. This motif was also observed in sequences selected from the TN8-IB library as well. Another motif, PFPWE (SEQ ID NO: 110) was also observed in sequences obtained from the TN8-IB library.

A consensus peptide, FHDCKWDLLTKQWVCHGL (SEQ ID NO: 58), was designed based on the DBL motif. Since peptides derived from the TN12-I library were the most active ones, the top 26 peptide sequences based on the above ranking criteria (section 5A) were aligned by the DBL motif. The underlined "core amino acid sequence" was obtained by determining the amino acid that occur the most in each position. The two cysteines adjacent to the core sequences were fixed amino acids in the TN12-I library. The rest of the amino acid sequence in the consensus peptide is taken from one of the candidate peptides, TALL-1-12-10 (Table 2, SEQ ID NO: 37). The peptide and peptibody that was derived from this consensus sequence were most active in the B cell proliferation assay.

EXAMPLE 2

Peptibodies

A set of 12 TALL-1 inhibitory peptibodies (Table 5) was constructed in which a monomer of each peptide was fused in-frame to the Fc region of human IgG1. Each TALL-1 inhibitory peptibody was constructed by annealing the pairs of oligonucleotides shown in Table 6 to generate a duplex encoding the peptide and a linker comprised of 5 glycine residues and one valine residue as an NdeI to SalI fragment. These duplex molecules were ligated into a vector (pAMG21-RANK-Fc, described herein) containing the human Fc gene, also digested with NdeI and SalI. The resulting ligation mixtures were transformed by electroporation into E. coli strain 2596 cells (GM221, described herein). Clones were screened for the ability to produce the recombinant protein product and to possess the gene fusion having the correct nucleotide sequence. A single such clone was selected for each of the peptibodies. The nucleotide and amino acid sequences of the fusion proteins are shown in FIG. 4A through 4F.

TABLE 5

Peptide sequences and oligonucleotides used to generate TALL-1 inhibitory peptibodies.

| Peptibody | Peptibody SEQ ID NO | Peptide Sequence | Sense oligo-nucleotide | Antisense oligo-nucleotide |
|---|---|---|---|---|
| TALL-1-8-1-a | 29 | PGTCFPFPWECTHA | 2517-24 | 2517-25 |
| TALL-1-8-2-a | 30 | WGACWPFPWECFKE | 2517-26 | 2517-27 |
| TALL-1-8-4-a | 31 | VPFCDLLTKHCFEA | 2517-28 | 2517-29 |
| TALL-1-12-4-a | 32 | GSRCKYKWDVLTKQCFHH | 2517-30 | 2517-31 |
| TALL-1-12-3-a | 33 | LPGCKWDLLIKQWVCDPL | 2517-32 | 2517-33 |
| TALL-1-12-5-a | 34 | SADCYFDILTKSDVCTSS | 2517-34 | 2517-35 |
| TALL-1-12-8-a | 35 | SDDCMYDQLTRMFICSNL | 2517-36 | 2517-37 |
| TALL-1-12-9-a | 36 | DLNCKYDELTYKEWCQFN | 2521-92 | 2521-93 |
| TALL-1-12-10-a | 37 | FHDCKYDLLTRQMVCHGL | 2521-94 | 2521-95 |
| TALL-1-12-11-a | 38 | RNHCFWDHLLKQDICPSP | 2521-96 | 2521-97 |
| TALL-1-12-14-a | 39 | ANQCWWDSLTKKNVCEFF | 2521-98 | 2521-99 |
| TALL-1-consensus | 58 | FHDCKWDLLTKQWVCHGL | 2551-48 | 2551-49 |

TABLE 5B

TALL-1 inhibitory peptibodies.

| Peptibody | Peptibody SEQ ID NO | Peptide Sequence |
|---|---|---|
| TALL-I-8-1-a | 111 | MPGTCFPFPW ECTHAGGGGG VDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| TALL-1-8-2-a | 112 | MWGACWPFPW ECFKEGGGGG VDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| TALL-1-8-4-a | 113 | MVPFCDLLTK HCFEAGGGGG VDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| TALL-1-12-4-a | 114 | MGSRCKYKWD VLTKQCFHHG GGGGVDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| TALL-1-12-3-a | 115 | MLPGCKWDLL IKQWVCDPLG GGGGVDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP |

TABLE 5B-continued

TALL-1 inhibitory peptibodies.

| Peptibody | Peptibody SEQ ID NO | Peptide Sequence |
|---|---|---|
| | | PVLDSDGSFF LYSKLTVDKS RWQQGNVFSC SVMHEALHNH YTQKSLSLSP GK |
| TALL-1-12-5-a | 116 | MSADCYFDIL TKSDVCTSSG GGGG VDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| TALL-1-12-8-a | 117 | MSDDCMYDQL TRMFICSNLG GGGGVDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| TALL-1-12-9-a | 118 | MDLNCKYDEL TYKEWCQFNG GGGGVDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| TALL-1-12-10-a | 119 | MFHDCKYDLL TRQMVCHGLG GGGGVDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| TALL-1-12-11-a | 120 | MRNHCFWDHL LKQDICPSPG GGGGVDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| TALL-1-12-14-a | 121 | MANQCWWDSL TKKNVCEFFG GGGGVDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| TALL-1-consensus | 122 | MFHDCKWDLL TKQWVCHGLG GGGGVDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| TALL-1 12-3 tandem dimer | 123 | MLPGCKWDLL IKQWVCDPLG SGSATGGSGS TASSGSGSAT HMLPGCKWDL LIKQWVCDPL GGGGGVDKTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS RDELTKNQVS LTCLVKGFYP SDIAVEWESN GQPENNYKTT PPVLDSDGSF FLYSKLTVDK SRWQQGNVFS CSVMHEALHN HYTQKSLSLS PGK |
| TALL-1 consensus tandem dimer | 124 | MFHDCKWDLL TKQWVCHGLG SGSATGGSGS TASSGSGSAT HMFHDCKWDL LTKQWVCHGL GGGGGVDKTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS RDELTKNQVS LTCLVKGFYP SDIAVEWESN GQPENNYKTT |

TABLE 5B-continued

TALL-1 inhibitory peptibodies.

| Peptibody | Peptibody SEQ ID NO | Peptide Sequence |
|---|---|---|
| | | PPVLDSDGSF FLYSKLTVDK SRWQQGNVFS CSVMHEALHN HYTQKSLSLS PGK |

TABLE 6

Sequences of oligonucleotides used in peptibody construction.

| Oligo-nucleotide ID number | SEQ ID NO | Sequence |
|---|---|---|
| 2517-24 | 71 | TAT GCC GGG TAC TTG TTT CCC GTT CCC GTG GGA ATG CAC TCA CGC TGG TGG AGG CGG TGG GG |
| 2517-25 | 72 | TCG ACC CCA CCG CCT CCT GGA GCG TGA GTG CAT TCC CAC GGG AAG CCG AAA CAA GTA CCC GGC A |
| 2517-26 | 73 | TAT GTG GGG TGC TTG TTG GCC GTT CCC GTG GGA ATG TTT CAA AGA GGT GGA GGC GGT GGG GG |
| 2517-27 | 74 | TCG ACC CCA CCG CCT CCA CCT TCT TTG AAA CAT TCC CACGGG AAC GGC CAA CAAGCA CCC CAC A |
| 2517-28 | 75 | TAT GGT TCC GTT CTG TGA CCT GCT GAC TAA ACA CTG TTT CGA AGC TGG TGG AGG CGG TGG GG |
| 2517-29 | 76 | TCG ACC CCA CCG CCT CCA CCA GCT TCG AAA CAG TGT TTA GTC AGC AGG TCA CAGAAC GGA ACC A |
| 2517-30 | 77 | TAT GGG TTC TCG TTG TAA ATA CAA ATG GGA CGT TCT GAC TAA ACA GTG TTT CCA CCA CGG TGG AGG CGG TGG GG |
| 2517-31 | 78 | TCG ACC CCA CCG CCT CCA CCG TGG TGG AAA CAC TGT TTA GTC AGA ACG TCC CAT TTG TAT TTA CAA CGA GAA CCC A |
| 2517-32 | 79 | TAT GCT GCC GGG TTG TAA ATG GGA CCT GCT GAT CAA ACA GTG GGT TTG TGA CCC GCT GGG TGG AGG CGG TGG GG |
| 2517-33 | 80 | TCG ACC CCA CCG CCT CCA CCC AGC GGG TCA CAA ACC CAC TGT TTG ATC AGC AGG TCC ATT TAC AAC CCG GCA GC A |
| 2517-34 | 81 | TAT GTC TGC TGA CTG TTA CTT CGA CAT CCT GAC TAA ATC TGA CGT TTG TAC TTC TTC TGG TGG AGG CGG TGG GG |
| 2517-35 | 82 | TCG ACC CCA CCG CCT CCA CCA GAA GAA GTA CAA ACG TCA GAT TTA GTC AGG ATG TCG AAG TAA CAG TCA GCA GAC A |
| 2517-36 | 83 | TAT GTC TGA CGA CTG TAT GTA CGA CCA GCT GAC TCG TAT GTT CAT CTG TTC TAA CCT GGG TGG AGG CGG TGG GG |
| 2517-37 | 84 | TCG ACC CCA CCG CCT CCA CCC AGG TTA GAA CAG ATG AAC ATA CGA GTC AGC TGG TCG TAC ATA CAG TCG TCA GAC A |
| 2521-92 | 85 | TAT GGA CCT GAA CTG TAA ATA CGA CGA ACT GAC TTA CAA AGA ATG GTG TCA GTT CAA CGG TGG AGG CGG TGG GG |
| 25221-93 | 86 | TCG ACC CCA CCG CCT CCA CCG TTG AAC TGA CAC CAT TCT TTG TAA GTC AGTTCG TCG TAT TTA CAG TTC AGG TCC A |
| 2521-94 | 87 | TAT GTT CCA CGA CTG TAA ATA CGA CCT GCT GAC TCG TCA GAT GGT TTG TCA CGG TCT GGG TGG AGG CGG TGG GG |
| 2521-95 | 88 | TCG ACC CCA CCG CCT CCA CCC AGA CCG TGA CAA ACC ATC TGA CGA GTC AGC AGG TCG TAT TTA CAG TCG TGG AAC A |
| 2521-96 | 89 | TAT GCG TAA CCA CTG TTT CTG GGA CCA CCT GCT GAA ACA GGA CAT CTG TCC GTC TCC GGG TGG AGG CGG TGG GG |
| 2521-97 | 90 | TCG ACC CCA CCG CCT CCA CCC GGA GAC GGA CAG ATG TCC TGT TTC AGC AGG TGG TCC CAG AAA CAG TGG TTA CGC A |

TABLE 6-continued

Sequences of oligonucleotides used in peptibody construction.

| Oligo-nucleotide ID number | SEQ ID NO | Sequence |
|---|---|---|
| 2521-98 | 91 | TAT GGC TAA CCA GTG TTG GTG GGA CTC TCT GCT GAA AAA AAA CGT TTG TGA ATT CTT CGG TGG AGG CGG TGG GG |
| 2521-99 | 92 | TCG ACC CCA CCG CCT CCA CCG AAG AAT TCA CAA ACG TTT TTT TTC AGC AGA GAG TCC CAC CAA CAC TGG TTA GCC A |
| 2551-48 | 93 | TAT GTT CCA CGA CTG CAA ATG GGA CCT GCT GAC CAA ACA GTG GGT TTG CCA CGG TCT GGG TGG AGG CGG TGG GG |
| 2551-49 | 94 | TCG ACC CCA CCG CCT CCA CCC AGA CCG TGG CAA ACC CAC TGT TTG GTC AGC AGG TCC CAT TTG CAG TCG TGG AAC A | pAMG21-RANK-Fc Vector pAMG21. The expression plasmid pAMG21 (ATCC accession no. 98113) can be derived from the Amgen expression vector pCFM1656(ATCC#69576) which in turn be derived from the Amgen expression vector system described in U.S. Pat. No. 4,710,473. The pCFM1656 plasmid can be derived from the described pCFM836 plasmid (U.S. Pat. No. 4,710,473) by:
- destroying the two endogenous NdeI restriction sites by end filling with T4 polymerase enzyme followed by blunt end ligation;
- replacing the DNA sequence between the unique AatII and ClaI restriction sites containing the synthetic $P_L$ promoter with a similar fragment obtained from pCFM636 (U.S. Pat. No. 4,710,473) containing the $P_L$ promoter (see SEQ ID NO: 95 below); and
- substituting the small DNA sequence between the unique ClaI and KpnI restriction sites with the oligonucleotide having the sequence of SEQ ID NO: 96.

The expression plasmid pAMG21 can then be derived from pCFM1656 by making a series of site-directed base changes by PCR overlapping oligonucleotide mutagenesis and DNA sequence substitutions. Starting with the BglII site (plasmid by # 180) immediately 5' to the plasmid replication promoter $P_{copB}$ and proceeding toward the plasmid replication genes, the base pair changes are as shown in Table 7 below.

TABLE 7

Base pair changes resulting in pAMG21

| pAMG21 bp # | bp in pCFM1656 | bp changed to in pAMG21 |
|---|---|---|
| # 204 | T/A | C/G |
| # 428 | A/T | G/C |
| # 509 | G/C | A/T |
| # 617 | — | insert two G/C by |
| # 679 | G/C | T/A |
| # 980 | T/A | C/G |

SEQ ID NO: 95:
AatII
5' CTAATTCCGCTCTCACCTACCAAACAATGCCCCCCTGCAAAAAATAAATTCATAT-
3' TGCAGATTAAGGCGAGAGTGGATGGTTTGTTACGGGGGGACGTMITATTTAAGTATA-

-AAAAAACATACAGATAACCATCTGCGGTGATAAATTATCTCTGGCGGTGTTGACATAAA-
-TTTTTTGTATGTCTATTGGTAGACGCCACTATTTAATAGAGACCGCCACAACTGTATTT-

-TACCACTGGCGGTGATACTGAGCACAT 3'
-ATGGTGACCGCCACTATGACTCGTGTAGC        5'
                                 ClaI

SEQ ID NO: 96:
5' CGATTTGATTCTAGAAGGAGGAATAACATATGGTTAACGCGTTGGAATTCGGTAC 3'
3' TAAACTAAGATCTTCCTCCTTATTGTATACCAATTGCGCAACCTTAAGC        5'
ClaI                                                   KpnI

TABLE 7-continued

Base pair changes resulting in pAMG21

| pAMG21 bp # | bp in pCFM1656 | bp changed to in pAMG21 |
|---|---|---|
| # 994 | G/C | A/T |
| # 1004 | A/T | C/G |
| # 1007 | C/G | T/A |
| # 1028 | A/T | T/A |
| # 1047 | C/G | T/A |
| # 1178 | G/C | T/A |
| # 1466 | G/C | T/A |
| # 2028 | G/C | bp deletion |
| # 2187 | C/G | T/A |
| # 2480 | A/T | T/A |
| # 2499-2502 | AGTG<br>TCAC | GTCA<br>CAGT |
| # 2642 | TCCGAGC<br>AGGCTCG | 7 bp deletion |
| # 3435 | G/C | A/T |
| # 3446 | G/C | A/T |
| # 3643 | A/T | T/A |

The DNA sequence between the unique AatII (position #4364 in pCFM1656) and SacII (position #4585 in pCFM1656) restriction sites is substituted with the DNA sequence below (SEQ ID NO: 97):

```
[AatII sticky end]          5'  GCGTAACGTATGCATGGTCTCC-
(position #4358 in pAMG21)  3'  TGCACGCATTGCATACGTACCAGAGG- -CCATGCGAGAGTAGGGAACTGCCAGGCATCAAATAAAACGAAAGGCTCAGTCGAAAGACT-
-GGTACGCTCTCATCCCTTGACGGTCCGTAGTTTATTTTGCTTTCCGAGTCAGCTTTCTGA- -GGGCCTTTCGTTTTATCTGTTGTTTGTCGGTGAACGCTCTCCTGAGTAGGACAAATCCGC-
-CCCGGAAAGCAAAATAGACAACAAACAGCCACTTGCGAGAGGACTCATCCTGTTTAGGCG- -CGGGAGCGGATTTGAACGTTGCGAAGCAACGGCCCGGAGGGTGGCGGGCAGGACGCCCGC-
-GCCCTCGCCTAAACTTGCAACGCTTCGTTGCCGGGCCTCCCACCGCCCGTCCTGCGGGCG- -CATAAACTGCCAGGCATCAAATTAAGCAGAAGGCCATCCTGACGGATGGCCTTTTTGCGT-
-GTATTTGACGGTCCGTAGTTTAATTCGTCTTCCGGTAGGACTGCCTACCGGAAAAACGCA- AatII
-TTCTACAAACTCTTTTGTTTATTTTTCTAAATACATTCAAATATGGACGTCGTACTTAAC-
-AAGATGTTTGAGAAAACAAATAAAAAGATTTATGTAAGTTTATACCTGCAGCATGAATTG- -TTTTAAAGTATGGGCAATCAATTGCTCCTGTTAAAATTGCTTTAGAAATACTTTGGCAGC-
-AAAATTTCATACCCGTTAGTTAACGAGGACAATTTTAACGAAATCTTTATGAAACCGTCG- -GGTTTGTTGTATTGAGTTTCATTTGCGCATTGGTTAAATGGAAAGTGACCGTGCGCTTAC-
-CCAAACAACATAACTCAAAGTAAACGCGTAACCAATTTACCTTTCACTGGCACGCGAATG- -TACAGCCTAATATTTTGAAATATCCCAAGAGCTTTTTCCTTCGCATGCCCACGCTAAAC-
-ATGTCGGATTATAAAAACTTTATAGGGTTCTCGAAAAAGGAAGCGTACGGGTGCGATTTG- -ATTCTTTTTCTCTTTTGGTTAAATCGTTGTTTGATTTATTATTTGCTATATTTATTTTTC-
-TAAGAAAAAGAGAAAACCAATTTAGCAACAAACTAAATAATAAACGATATAAATAAAAAG- -GATAATTATCAACTAGAGAAGGAACAATTAATGGTATGTTCATACACGCATGTAAAAATA-
-CTATTAATAGTTGATCTCTTCCTTGTTAATTACCATACAAGTATGTGCGTACATTTTTAT- -AACTATCTATATAGTTGTCTTTCTCTGAATGTGCAAAACTAAGCATTCCGAAGCCATTAT-
-TTGATAGATATATCAACAGAAAGAGACTTACACGTTTTGATTCGTAAGGCTTCGGTAATA- -TAGCAGTATGAATAGGGAAACTAAACCCAGTGATAAGACCTGATGATTTCGCTTCTTTAA-
-ATCGTCATACTTATCCCTTTGATTTGGGTCACTATTCTGGACTACTAAAGCGAAGAAATT- -TTACATTTGGAGATTTTTTATTTACAGCATTGTTTTCAAATATATTCCAATTAATCGGTG-
-AATGTAAACCTCTAAAAAATAAATGTCGTAACAAAAGTTTATATAAGGTTAATTAGCCAC- -AATGATTGGAGTTAGAATAATCTACTATAGGATCATATTTTATTAAATTAGCGTCATCAT-
-TTACTAACCTCAATCTTATTAGATGATATCCTAGTATAAAATAATTTAATCGCAGTAGTA- -AATATTGCCTCCATTTTTTAGGGTAATTATCCAGAATTGAAATATCAGATTTAACCATAG-
-TTATAACGGAGGTAAAAAATCCCATTAATAGGTCTTAACTTTATAGTCTAAATTGGTATC- -AATGAGGATAAATGATCGCGAGTAAATAATATTCACAATGTACCATTTTAGTCATATCAG-
-TTACTCCTATTTACTAGCGCTCATTTATTATAAGTGTTACATGGTAAAATCAGTATAGTC-
```

-continued

```
-ATAAGCATTGATTAATATCATTATTGCTTCTACAGGCTTTAATTTTATTAATTATTCTGT-
-TATTCGTAACTAATTATAGTAATAACGAAGATGTCCGAAATTAAAATAATTAATAAGACA-

-AAGTGTCGTCGGCATTTATGTCTTTCATACCCATCTCTTTATCCTTACCTATTGTTTGTC-
-TTCACAGCAGCCGTAAATACAGAAAGTATGGGTAGAGAAATAGGAATGGATAACAAACAG-

-GCAAGTTTTGCGTGTTATATATCATTAAAACGGTAATAGATTGACATTTGATTCTAATAA-
-CGTTCAAAACGCACAATATATAGTAATTTTGCCATTATCTAACTGTAAACTAAGATTATT-

-ATTGGATTTTTGTCACACTATTATATCGCTTGAAATACAATTGTTTAACATAAGTACCTG-
-TAACCTAAAAACAGTGTGATAATATAGCGAACTTTATGTTAACAAATTGTATTCATGGAC-

-TAGGATCGTACAGGTTTACGCAAGAAAATGGTTTGTTATAGTCGATTAATCGATTTGATT-
-ATCCTAGCATGTCCAAATGCGTTCTTTTACCAAACAATATCAGCTAATTAGCTAAACTAA-

-CTAGATTTGTTTTAACTAATTAAAGGAGGAATAACATATGGTTAACGCGTTGGAATTCGA-
-GATCTAAACAAAATTGATTAATTTCCTCCTTATTGTATACCAATTGCGCAACCTTAAGCT-

SacII
-GCTCACTAGTGTCGACCTGCAGGGTACCATGGAAGCTTACTCGAGGATCCGCGGAAAGAA-
-CGAGTGATCACAGCTGGACGTCCCATGGTACCTTCGAATGAGCTCCTAGGCGCCTTTCTT-

-GAAGAAGAAGAAGAAAGCCCGAAAGGAAGCTGAGTTGGCTGCTGCCACCGCTGAGCAATA-
-CTTCTTCTTCTTCTTTCGGGCTTTCCTTCGACTCAACCGACGACGGTGGCGACTCGTTAT-

-ACTAGCATAACCCCTTGGGGCCTCTAAACGGGTCTTGAGGGGTTTTTTGCTGAAAGGAGG-
-TGATCGTATTGGGGAACCCCGGAGATTTGCCCAGAACTCCCCAAAAAACGACTTTCCTCC-

-AACCGCTCTTCACGCTCTTCACGC  3'      [SacII sticky end]
-TTGGCGAGAAGTGCGAGAAGTG    5'      (position #5904 in pAMG21)
```

During the ligation of the sticky ends of this substitution DNA sequence, the outside AatII and SacII sites are destroyed. There are unique AatII and SacII sites in the substituted DNA.

A gene encoding human RANK fused to the N-terminus of Fc was ligated into pAMG21 as an NdeI to BamHI fragment to generate Amgen Strain #4125. This construct was modified to insert a valine codon at the junction of RANK and Fc. The adjacent valine and aspartate codons create a unique SalI site. This allows for the fusion of peptides at the N-terminus of Fc3 between the unique NdeI and SalI sites. The RANK sequence is deleted upon insertion of a new NdeI-SalI fragment. The sequence of the vector is given in FIG. 5A through 5M.

GM221 (Amgen #2596). The Amgen host strain #2596 is an *E. coli* K-12 strain derived from Amgen strain #393, which is a derivative of *E. coli* W1485, obtained from the *E. coli* Genetic Stock Center, Yale University, New Haven, Conn. (CGSC strain 6159). It has been modified to contain both the temperature sensitive lambda repressor cI857s7 in the early ebb region and the lacI$^Q$ repressor in the late ebg region (68 minutes). The presence of these two repressor genes allows the use of this host with a variety of expression systems, however both of these repressors are irrelevant to the expression from luxP$_R$. The untransformed host has no antibiotic resistances.

The ribosome binding site of the cI857s7 gene has been modified to include an enhanced RBS. It has been inserted into the ebg operon between nucleotide position 1170 and 1411 as numbered in Genbank accession number M64441Gb_Ba with deletion of the intervening ebg sequence. The sequence of the insert is shown below with lower case letters representing the ebg sequences flanking the insert shown below (SEQ ID NO: 98):

```
ttattttcgtGCGGCCGCACCATTATCACCGCCAGAGGTAAACTAGTCAA
CACGCACGGTGTTAGATATTTATCCCTTGCGGTGATAGATTGAGCACATC
GATTTGATTCTAGAAGGAGGGATAATATATGAGCACAAAAAAGAAACCAT
```

-continued

```
TAACACAAGAGCAGCTTGAGGACGCACGTCGCCTTAAAGCAATTTATGAA

AAAAAGAAAAATGAACTTGGCTTATCCCAGGAATCTGTCGCAGACAAGAT

GGGGATGGGGCAGTCAGGCGTTGGTGCTTTATTTAATGGCATCAATGCAT

TAAATGCTTATAACGCCGCATTGCTTACAAAAATTCTCAAAGTTAGCGTT

GAAGAATTTAGCCCTTCAATCGCCAGAGAATCTACGAGATGTATGAAGCG

GTTAGTATGCAGCCGTCACTTAGAAGTGAGTATGAGTACCCTGTTTTTTC

TCATGTTCAGGCAGGGATGTTCTCACCTAAGCTTAGAACCTTTACCAAAG

GTGATGCGGAGAGATGGGTAAGCACAACCAAAAAAGCCAGTGATTCTGCA

TTCTGGCTTGAGGTTGAAGGTAATTCCATGACCGCACCAACAGGCTCCAA

GCCAAGCTTTCCTGACGGAATGTTAATTCTCGTTGACCCTGAGCAGGCTG

TTGAGCCAGGTGATTTCTGCATAGCCAGACTTGGGGGTGATGAGTTTACC

TTCAAGAAACTGATCAGGGATAGCGGTCAGGTGTTTTTACAACCACTAAA

CCCACAGTACCCAATGATCCCATGCAATGAGAGTTGTTCCGTTGTGGGGA

AAGTTATCGCTAGTCAGTGGCCTGAAGAGACGTTTGGCTGATAGACTAGT

GGATCCACTAGTgtttctgccc
```

The construct was delivered to the chromosome using a recombinant phage called MMebg-cI857s7enhanced RBS #4 into F'tet/393. After recombination and resolution only the chromosomal insert described above remains in the cell. It was renamed F'tet/GM101. F'tet/GM101 was then modified by the delivery of a lacI$^Q$ construct into the ebg operon between nucleotide position 2493 and 2937 as numbered in the Genbank accession number M64441 Gb_Ba with the deletion of the intervening ebg sequence. The sequence of the insert is shown below with the lower case letters representing the ebg sequences flanking the insert (SEQ ID NO: 99) shown below:

```
ggcggaaaccGACGTCCATCGAATGGTGCAAAACCTTTCGCGGTATGGCA

TGATAGCGCCCGGAAGAGAGTCAATTCAGGGTGGTGAATGTGAAACCAGT

AACGTTATACGATGTCGCAGAGTATGCCGGTGTCTCTTATCAGACCGTTT

CCCGCGTGGTGAACCAGGCCAGCCACGTTTCTGCGAAAACGCGGGAAAAA

GTCGAAGCGGCGATGGCGGAGCTGAATTACATTCCCAACCGCGTGGCACA

ACAACTGGCGGGCAAACAGTCGCTCCTGATTGGCGTTGCCACCTCCAGTC

TGGCCCTGCACGCGCCGTCGCAAATTGTCGCGGCGATTAAATCTCGCGCC

GATCAACTGGGTGCCAGCGTGGTGGTGTCGATGGTAGAACGAAGCGGCGT

CGAAGCCTGTAAAGCGGCGGTGCACAATCTTCTCGCGCAACGCGTCAGTG

GGCTGATCATTAACTATCCGCTGGATGACCAGGATGCCATTGCTGTGGAA

GCTGCCTGCACTAATGTTCCGGCGTTATTTCTTGATGTCTCTGACCAGAC

ACCCATCAACAGTATTATTTTCTCCCATGAAGACGGTACGCGACTGGGCG

TGGAGCATCTGGTCGCATTGGGTCACCAGCAAATCGCGCTGTTAGCGGGC

CCATTAAGTTCTGTCTCGGCGCGTCTGCGTCTGGCTGGCTGGCATAAATA

TCTCACTCGCAATCAAATTCAGCCGATAGCGGAACGGGAAGGCGACTGGA

GTGCCATGTCCGGTTTTCAACAAACCATGCAAATGCTGAATGAGGGCATC

GTTCCCACTGCGATGCTGGTTGCCAACGATCAGATGGCGCTGGGCGCAAT

GCGCGCCATTACCGAGTCCGGGCTGCGCGTTGGTGCGGATATCTCGGTAG

TGGGATACGACGATACCGAAGACAGCTCATGTTATATCCCGCCGTTAACC

ACCATCAAACAGGATTTTCGCCTGCTGGGCAAACCAGCGTGGACCGCTT

GCTGCAACTCTCTCAGGGCCAGGCGGTGAAGGGCAATCAGCTGTTGCCCG

TCTCACTGGTGAAAAGAAAAACCACCCTGGCGCCCAATACGCAAACCGCC

TCTCCCCGCGCGTTGGCCGATTCATTAATGCAGCTGGCACGACAGGTTTC

CCGACTGGAAAGCGGACAGTAAGGTACCATAGGATCCaggcacagga
```

The construct was delivered to the chromosome using a recombinant phage called AGebg-LacIQ#5 into F'tet/GM101. After recombination and resolution only the chromosomal insert described above remains in the cell. It was renamed F'tet/GM221. The F'tet episome was cured from the strain using acridine orange at a concentration of 25 μg/ml in LB. The cured strain was identified as tetracyline sensitive and was stored as GM221.

Expression in *E. coli*. Cultures of each of the pAMG21-Fc-fusion constructs in *E. coli* GM221 were grown at 37° C. in Luria Broth medium. Induction of gene product expression from the luxPR promoter was achieved following the addition of the synthetic autoinducer N-(3-oxohexanoyl)-DL-homoserine lactone to the culture media to a final concentration of 20 ng/ml. Cultures were incubated at 37° C. for a further 3 hours. After 3 hours, the bacterial cultures were examined by microscopy for the presence of inclusion bodies and were then collected by centrifugation. Refractile inclusion bodies were observed in induced cultures indicating that the Fc-fusions were most likely produced in the insoluble fraction in *E. coli*. Cell pellets were lysed directly by resuspension in Laemmli sample buffer containing 10% β-mercaptoethanol and were analyzed by SDS-PAGE. In each case, an intense Coomassie-stained band of the appropriate molecular weight was observed on an SDS-PAGE gel.

EXAMPLE 3

TALL-1 Peptibody Inhibits TALL-1 Mediated B Cell Proliferation

Mouse B lymphocytes were isolated from C57BL/6 spleens by negative selection. (MACS CD43 (Ly-48) Microbeads, Miltenyi Biotech, Auburn, Calif.). Purified ($10^5$) B cells were cultured in MEM, 10% heat inactivated FCS, $5 \times 10^{-5}$M 2-mercaptoethanol, 100 U/ml penicillin, 100 μg/ml streptomycin) in triplicate in 96-well flat bottom tissue culture plates with 10 μg/ml TALL-1 protein and 2 μg/ml of Goat F(ab')$_2$ anti-mouse IgM (Jackson ImmunoResearch Laboratory, West Grove, Pa.) with the indicated amount of recombinant TALL-1 peptibody for a period of 4 days at 37° C., 5% $CO_2$. Proliferation was measured by the uptake of radioactive $^3$[H] thymidine after an 18-hour incubation period.

EXAMPLE 4

TALL-1 Peptibody Blocks TALL-1 Binding to its Receptors

Figure 9:
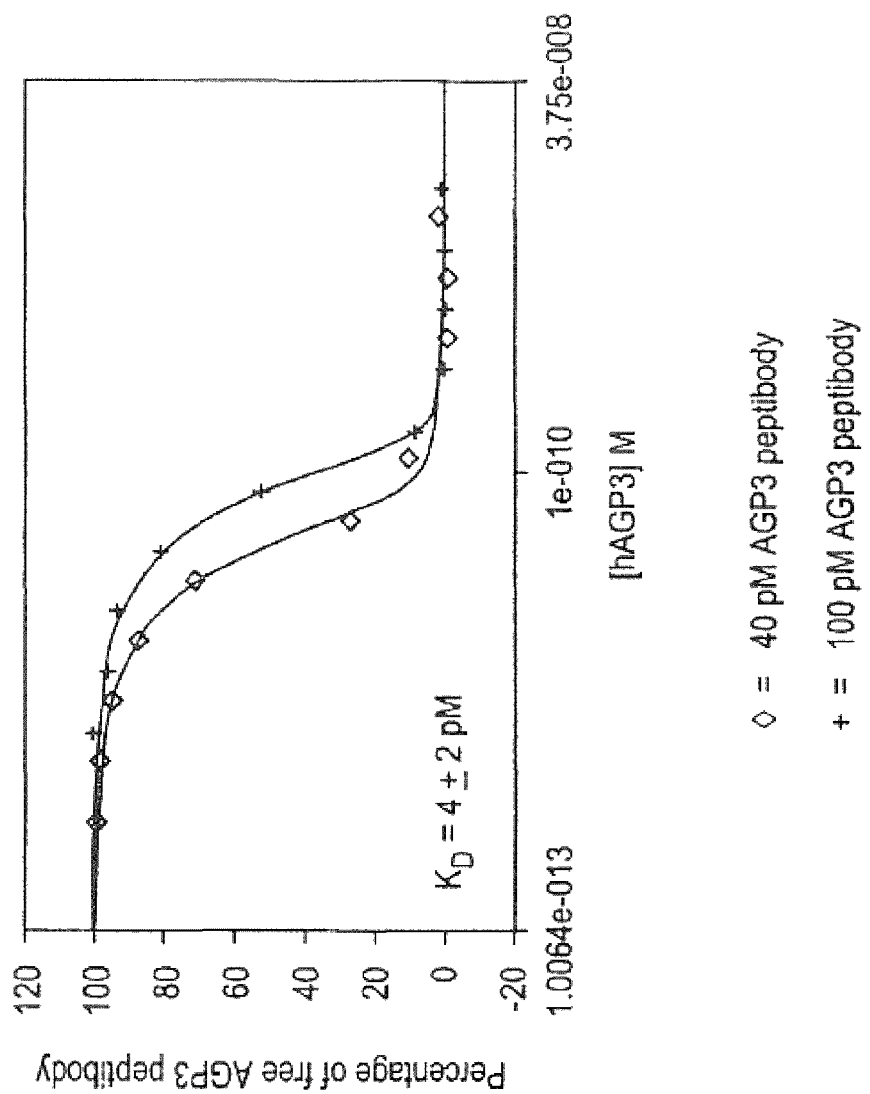
FIG. 9. AGP3 peptibody binds to AGP3 with high affinity. Dissociation equilibrium constant (K$_D$) was obtained from nonlinear regression of the competition curves using a dual-curve one-site homogeneous binding model (KinEx™ software). K$_D$ is about 4 pM for AGP3 peptibody binding with human AGP3 (SEQ ID NO: 123).

Reacti-Gel 6×(Pierce) were pre-coated with human AGP3 (also known as TALL-1, Khare et al., Proc. Natl. Acad. Sci. 97:3370-3375, 2000) and blocked with BSA. 100 μM and 40 μM of AGP3 peptibody samples were incubated with indicated various concentrations of human AGP3 at room temperature for 8 hours before run through the human AGP3-coated beads. The amount of the bead-bound peptibody was quantified by fluorescent ($Cy_5$) labeled goat anti-human-Fc antibody (Jackson Immuno Research). The binding signal is proportional to the concentration of free peptibody at binding equilibrium. Dissociation equilibrium constant ($K_D$) was obtained from nonlinear regression of the competition curves using a dual-curve one-site homogeneous binding model (KinEx™ software). $K_D$ is about 4 μM for AGP3 peptibody (SEQ ID NO: 123) binding with human AGP3 (FIG. 9).

To determine if this AGP3 peptibody can neutralize murine AGP3 binding as well as human AGP3, a BIAcore neutralizing assay was utilized. All experiments were performed on a BIAcore 3000 at room temperature. Human TACI-Fc protein (Xia et al, J. Exp. Med. 192, 137-144, 2000) was immobilized to a Bl chip using 10 mM Acetate pH 4.0 to a level of 2900RU. A blank flow cell was used as a background control. Using a running buffer of PBS (without calcium or magnesium) containing 0.005% P20, 1 nM recombinant human AGP3 (in running buffer plus, 0.1 mg/ml BSA) was incubated without and with indicated various amount of AGP3 peptibody (x axis) before injected over the surface of the receptor. Regeneration was performed using 8 mM glycine pH 1.5 for 1 minute, 25 mM 3-[cyclohexylamino]-1-propanesulfonic acid (CAPS) pH 10.5, 1 M NaCl for 1 minute. For determination of murine AGP3 binding, human his-tagged TACI was immobilized to 1000 RU in the above buffer. 5 nM recombinant murine AGP3 (in running buffer plus, 0.1 mg/ml BSA) was incubated without and with the various amounts indicated in FIG. 11 of AGP3 peptibody (x axis) before injected over the surface of the receptor. Regeneration was performed with 10 mM HCl pH2, twice for 30 seconds. Relative binding of both human and murine AGP3 at presence vs absence of AGP3 peptibody (SEQ ID NO: 123) was measured (y axis). Relative binding response was determined as (RU-RU blank/RUo-RU blank). The AGP3 peptibody (SEQ ID NO: 123) inhibited both human and murine AGP3 binding to its receptor TACI (FIGS. 10A and 10B).

To examine if this AGP3 peptibody blocks AGP3 binding to all three receptors (TACI, BCMA and BAFFR), recombinant soluble receptor TACI, BCMA and BAFFR proteins were immobilized to CM5 chip. Using 10 mM acetate, pH4, human TACI-Fe was immobilized to 6300 RU, human BCMA-Fc to 5000 RU, and BAFFR-Fc to 6000 RU. 1 nM of recombinant human AGP3 (in running buffer containing 0.1 mg/ml BSA and 0.1 mg/ml Heparin) or 1 nM recombinant APRIL protein (Yu, et al., Nat. Immunol., 1:252-256, 2000) were incubated with indicated amount of AGP3 peptibody before injection over each receptor surface. Regeneration for the AGP3 experiment was done with 8 mM glycine, pH 1.5, for 1 minute, followed by 25 mM CAPS, pH 10.5, 1M NaCl for 1 minute. Regeneration for the APRIL experiment was performed with 8 mM glycine, pH 2, for one minute, followed by 25 mM CAPS, pH 10.5, 1 M NaCl for one minute. Relative binding of AGP3 or APRIL was measured. AGP3 peptibody (SEQ ID NO: 123) blocked AGP3 binding to all three receptors (FIG. 11A). AGP3 peptibody didn't affect APRIL binding to the receptors (FIG. 11B).

EXAMPLE 5

AGP3 Peptibody Blocks AGP3 Mediated B Cell Proliferation

Mouse B lymphocytes were isolated from C57BL/6 spleens by negative selection. (MACS CD43 (Ly-48) Microbeads, Miltenyi Biotech, Auburn, Calif.). Purified ($10^5$) B cells were cultured in minimal essential medium (MEM), 10% heat inactivated fetal calf serum (FCS), $5\times10^{-5}$ M 2-mercaptoethanol, 100 U/ml penicillin, 100 µg/ml streptomycin) in triplicate in 96-well flat bottom tissue culture plates with 10 ng/ml AGP3 (TALL-1) protein and 2 µg/ml of Goat F(ab')$_2$ anti-mouse IgM (Jackson ImmunoResearch Laboratory, West Grove, Pa.) with the indicated amount of recombinant AGP3 peptibody (SEQ ID NO: 123) for a period of 4 days at 37° C., 5% $CO_2$. Proliferation was measured by the uptake of radioactive $^3$[H] thymidine after an 18-hour incubation period.

EXAMPLE 6

AGP3 Peptibody on AGP3-Stimulated Ig Production in Mice

Mice (Balb/c females of 9-14 weeks of age and 19-21 g of weight) were purchased from Charles River Laboratories, Wilmington, Mass. Mice (n=10) were treated i.p. with 1 mg/Kg of human AGP3 once a day for five consecutive days followed by 5 mg/Kg or 0.5 mg/Kg of AGP3 peptibody (SEQ ID NO: 123) or by saline or by 5 mg/Kg of human Fc. Other mice were left untreated. Mice were sacrificed on the sixth day to measure serum IgM and IgA, which were measured by ELISA. Briefly, plates were coated with capture antibodies specific for IgM or IgA (Southern Biotechnology Associates, Birmingham, Ala.), blocked, and added with dilutions of standard (IgM from Calbiochem, San Diego, Calif. and IgA from Southern Biotechnology Associates) or test samples. Captured Ig were revealed using biotinylated antibodies specific for IgM or IgA (Southern Biotechnology Associates), neutravidin-conjugated peroxidase (Pierce, Rockford, Ill.), and tetramethylbenzidine (TMB) microwell peroxidase substrate(KPL, Gaithersburg, Md.). Optical densities were quantitated in a Thermomax ELISA reader (Molecular Devices, Menlo Park, Calif.).

Figure 12A:
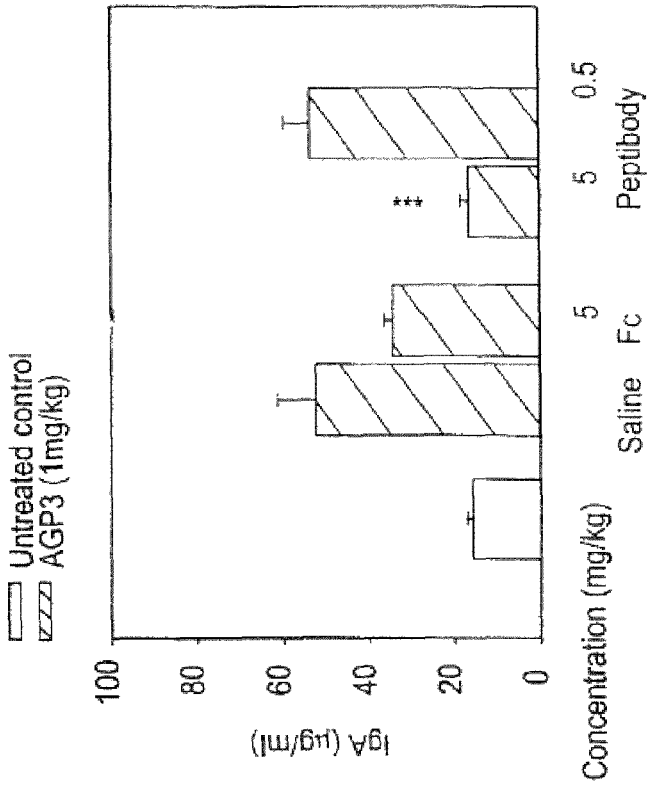
FIGS. 12A and 12B. AGP3 peptibody inhibits mouse serum immunoglobulin level increase induced by human AGP3 challenge. Balb/c mice received 7 daily intraperitoneal injections of 1 mg/Kg human AGP3 protein along with saline, human Fc, or AGP3 peptibody at indicated doses, and were bled on day 8. Serum total IgM and IgA level were measured by ELISA (SEQ ID NO: 123).
Figure 12B:
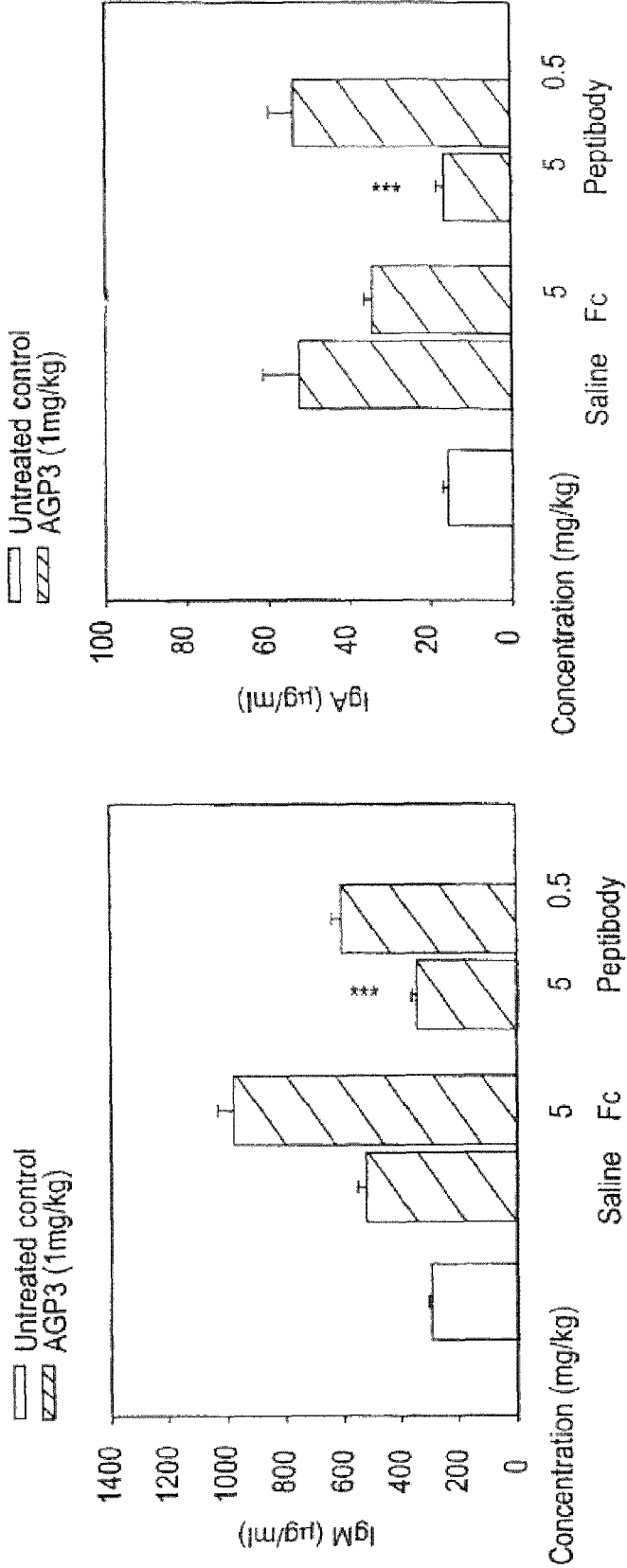

Human AGP3-stimulated increase in serum levels of IgM and IgA was blocked by 5 mg/Kg of the anti-AGP3 peptibody (SEQ ID NO: 123) and not by 0.5 mg/Kg (FIGS. 12A and 12B).

EXAMPLE 7

AGP3 Peptibody Reduced Spleen B Cell Number in Mice

Mice (as above, n=7) were treated i.p. for seven consecutive days with 5 mg/Kg or 1.5 mg/Kg or 0.5 mg/Kg of AGP3 peptibody (SEQ ID NO: 123) or with saline or with 5 mg/Kg of human Fc. Mice were sacrificed on the eighth day to count spleen B cell number. Spleens were collected in saline and gently disrupted by manual homogenization to yield a cell suspension. The total cell number was obtained with a ME counter (Technicon, Tarrytown, N.Y.). Percentages of B cells were derived by immunofluorescence double staining and flow cytometry using fluorescein isothiocyanate (FITC)-conjugated and phycoerythrin (PE)-conjugated Ab against CD3 and B220, respectively (PharMingen, San Diego, Calif.) and a FACScan analyser (Becton and Dickinson, Mountain View, Calif.). B cells were identified for being CD3-B220+. At all doses, the AGP3 peptibody (SEQ ID NO: 123) decreased spleen B cell number in a dose-response fashion (FIGS. 12A and 12B) (SEQ ID NO: 123).

TABLE 8

AGP3 Pb Reduces B Cell Number in Normal Mice

| n = 7 | dose (1/day × 7) | spleen B cell (1 × 10e6) | SD | t test |
|---|---|---|---|---|
| saline | | 51.3 | 9.6 | |
| Fc | 5 mg/Kg | 45.5 | 7.1 | |
| Peptibody | 5 mg/Kg | 20.1 | 3.8 | 1.37856E−05 |
| | 1.5 mg/Kg | 22.6 | 6.9 | 5.10194E−05 |
| | 0.5 mg/Kg | 25.8 | 3.6 | 0.000111409 |

EXAMPLE 8

AGP3 Peptibody Reduced Arthritis Severity in Mouse CIA Model

Eight to 12 week old DBA/1 mice (obtained from Jackson Laboratories, Bar Harbor, Me.) were immunized with bovine collagen type II (bCII) (purchased from University of Utah), emulsified in complete Freunds adjuvant (Difco) intradermally at the base of tail. Each injection was 100 µl containing 100 µg of bCII. Mice were boosted 3 weeks after the initial immunization with bCII emulsified in incomplete Freunds adjuvant. Treatment was begun from the day of booster immunization for 4 weeks. Mice were examined for the development of arthritis. As described before (Khare et al., J. Immunol. 155: 3653-9, 1995), all four paws were individually scored from 0-3. Therefore arthritis severity could vary from 0 to 12 for each animal. AGP3 (SEQ ID NO: 123) peptibody treatment significantly reduced the severity of arthritic scores (FIG. 13).

Serum samples were taken one week after final treatment (day 35) for the analysis of anti-collagen antibody level. High binding ELISA plates (Immulon, Nunc) were coated with 50 µl of 4 µg/ml solution of bovine CII in carbonate buffer and plated were kept in cold overnight in the refrigerator. Plates were washed three times with cold water. 75 µl of blocking solution made up of PBS/0.05% tween 20/1 % BSA was used to block non-specific binding for an hour. Samples were diluted (in blocking buffer) in dilution plates at 1:25, 1:100, 1:400, and 1:1600 and 25 μl of these samples were added to each well of the ELISA plate for a final dilution of 100, 400, 1600, and 6400 with a final volume of 100 μl/well. After incubation at room temperature for 3 hours, plates were washed three times again. 100 μl of secondary antibody diluted in blocking buffer (rat anti-mouse IgM, IgG2a, IgG2b, IgG1, IgG3-HRP) was added to each well and plates were incubated for at least 2 hours. Plates were washed four times. 100 μl of TMB solution (Sigma) was added to each well and the reaction was stopped using 50 μl of 25% sulfuric acid. Plates were read using an ELISA plate reader at 450 nm. OD was compared with a standard pool representing units/ml. AGP3 peptibody (SEQ ID NO: 123) treatment reduced serum anti-collagen II IgG1, IgG3, IgG2a, and IgG2b levels compared to PBS or Fc control treatment groups (FIG. 14).

EXAMPLE 9

Treatment of AGP3 Peptibody in NZB/NZW Lupus Mice

Figure 15A:
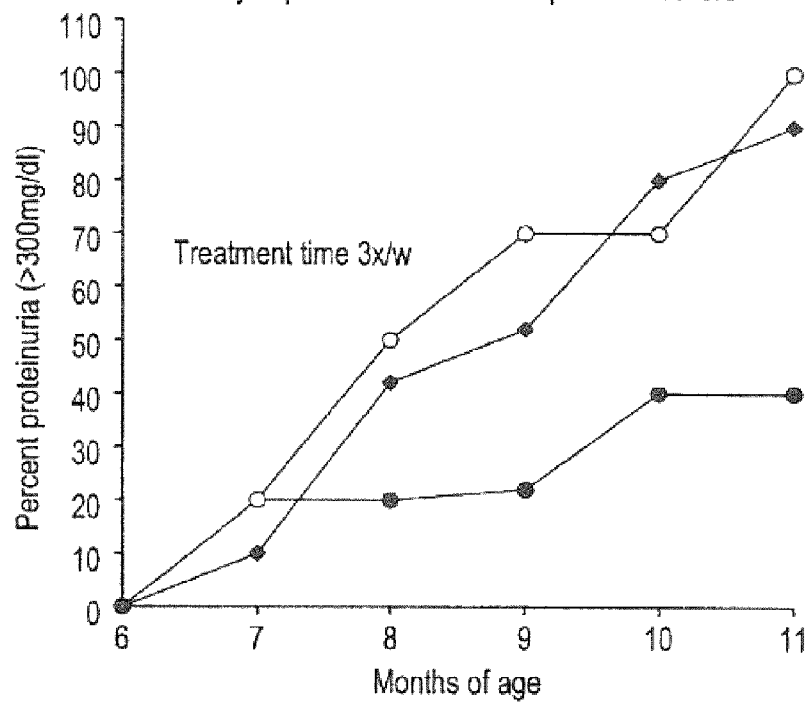

Five month old lupus prone NZBx NZBWF1 mice were treated i.p. 3x/week for 8 weeks with PBS or indicated doses of AGP3 peptibody or human Fc proteins. Prior to the treatment, animals were pre-screened for protein in the urine with Albustix reagents strips (Bayer AG). Mice having greater than 100 mg/dl of protein in the urine were not included in the study. Protein in the urine was evaluated monthly throughout the life of the experiment. AGP3 peptibody (SEQ ID NO: 123) treatment led to delay of proteinuria onset and improved survival (FIGS. 15A and 15B).

AGP3 peptibody treatment reduced B cell number in mice. Balb/c mice received 7 daily intraperitoneal injections of indicated amount of AGP3 peptibody (SEQ ID NO: 123) or human Fc protein. On day 8, spleens were collected, and subject to FACS analysis for B220+B cells as set for in Table 8.

TABLE 8

AGP3 Pb Reduces B Cell Number in Normal Mice

| n = 7 | dose (1/day × 7) | Spleen B cell (1 × 10e6) | SD | t test |
|---|---|---|---|---|
| saline | | 51.3 | 9.6 | |
| Fc | 5 mg/Kg | 45.5 | 7.1 | |
| Peptibody | 5 mg/Kg | 20.1 | 3.8 | 1.37856E−05 |
| | 1.5 mg/Kg | 22.6 | 6.9 | 5.10194E−05 |
| | 0.5 mg/Kg | 25.8 | 3.6 | 0.000111409 |

The invention now being fully described, it will be apparent to one of ordinary skill in the art that many changes and modifications can be made thereto, without departing from the spirit and scope of the invention as set forth herein.

SEQUENCE LISTING

<160> NUMBER OF SEQ ID NOS: 197

<210> SEQ ID NO 1
<211> LENGTH: 684
<212> TYPE: DNA
<213> ORGANISM: Homo sapiens
<220> FEATURE:
<221> NAME/KEY: CDS
<222> LOCATION: (1)..(684)

<400> SEQUENCE: 1

```
atg gac aaa act cac aca tgt cca cct tgt cca gct ccg gaa ctc ctg      48
Met Asp Lys Thr His Thr Cys Pro Pro Cys Pro Ala Pro Glu Leu Leu
1               5                   10                  15 ggg gga ccg tca gtc ttc ctc ttc ccc cca aaa ccc aag gac acc ctc      96
Gly Gly Pro Ser Val Phe Leu Phe Pro Pro Lys Pro Lys Asp Thr Leu
            20                  25                  30 atg atc tcc cgg acc cct gag gtc aca tgc gtg gtg gtg gac gtg agc     144
Met Ile Ser Arg Thr Pro Glu Val Thr Cys Val Val Val Asp Val Ser
        35                  40                  45 cac gaa gac cct gag gtc aag ttc aac tgg tac gtg gac ggc gtg gag     192
His Glu Asp Pro Glu Val Lys Phe Asn Trp Tyr Val Asp Gly Val Glu
    50                  55                  60 gtg cat aat gcc aag aca aag ccg cgg gag gag cag tac aac agc acg     240
Val His Asn Ala Lys Thr Lys Pro Arg Glu Glu Gln Tyr Asn Ser Thr
65                  70                  75                  80 tac cgt gtg gtc agc gtc ctc acc gtc ctg cac cag gac tgg ctg aat     288
Tyr Arg Val Val Ser Val Leu Thr Val Leu His Gln Asp Trp Leu Asn
                85                  90                  95 ggc aag gag tac aag tgc aag gtc tcc aac aaa gcc ctc cca gcc ccc     336
Gly Lys Glu Tyr Lys Cys Lys Val Ser Asn Lys Ala Leu Pro Ala Pro
            100                 105                 110 atc gag aaa acc atc tcc aaa gcc aaa ggg cag ccc cga gaa cca cag     384
```

```
Ile Glu Lys Thr Ile Ser Lys Ala Lys Gly Gln Pro Arg Glu Pro Gln
        115                 120                 125 gtg tac acc ctg ccc cca tcc cgg gat gag ctg acc aag aac cag gtc       432
Val Tyr Thr Leu Pro Pro Ser Arg Asp Glu Leu Thr Lys Asn Gln Val
130                 135                 140 agc ctg acc tgc ctg gtc aaa ggc ttc tat ccc agc gac atc gcc gtg       480
Ser Leu Thr Cys Leu Val Lys Gly Phe Tyr Pro Ser Asp Ile Ala Val
145                 150                 155                 160 gag tgg gag agc aat ggg cag ccg gag aac aac tac aag acc acg cct       528
Glu Trp Glu Ser Asn Gly Gln Pro Glu Asn Asn Tyr Lys Thr Thr Pro
        165                 170                 175 ccc gtg ctg gac tcc gac ggc tcc ttc ttc ctc tac agc aag ctc acc       576
Pro Val Leu Asp Ser Asp Gly Ser Phe Phe Leu Tyr Ser Lys Leu Thr
        180                 185                 190 gtg gac aag agc agg tgg cag cag ggg aac gtc ttc tca tgc tcc gtg       624
Val Asp Lys Ser Arg Trp Gln Gln Gly Asn Val Phe Ser Cys Ser Val
        195                 200                 205 atg cat gag gct ctg cac aac cac tac acg cag aag agc ctc tcc ctg       672
Met His Glu Ala Leu His Asn His Tyr Thr Gln Lys Ser Leu Ser Leu
210                 215                 220 tct ccg ggt aaa                                                       684
Ser Pro Gly Lys
225

<210> SEQ ID NO 2
<211> LENGTH: 228
<212> TYPE: PRT
<213> ORGANISM: Homo sapiens

<400> SEQUENCE: 2

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220
```

Ser Pro Gly Lys
225

<210> SEQ ID NO 3
<211> LENGTH: 62
<212> TYPE: DNA
<213> ORGANISM: Artificial Sequence
<220> FEATURE:
<223> OTHER INFORMATION: NdeI to SalI fragment
<220> FEATURE:
<221> NAME/KEY: CDS
<222> LOCATION: (2)..(61)

<400> SEQUENCE: 3

```
t atg ccg ggt act tgt ttc ccg ttc ccg tgg gaa tgc act cac gct ggt      49
  Met Pro Gly Thr Cys Phe Pro Phe Pro Trp Glu Cys Thr His Ala Gly
  1               5                   10                  15 gga ggc ggt ggg g                                                      62
Gly Gly Gly Gly
            20
```

<210> SEQ ID NO 4
<211> LENGTH: 20
<212> TYPE: PRT
<213> ORGANISM: Artificial Sequence
<220> FEATURE:
<223> OTHER INFORMATION: NdeI to SalI fragment

<400> SEQUENCE: 4

Met Pro Gly Thr Cys Phe Pro Phe Pro Trp Glu Cys Thr His Ala Gly
1               5                   10                  15

Gly Gly Gly Gly
            20

<210> SEQ ID NO 5
<211> LENGTH: 62
<212> TYPE: DNA
<213> ORGANISM: Artificial Sequence
<220> FEATURE:
<223> OTHER INFORMATION: NdeI to SalI fragment
<220> FEATURE:
<221> NAME/KEY: CDS
<222> LOCATION: (2)..(61)

<400> SEQUENCE: 5

```
t atg tgg ggt gct tgt tgg ccg ttc ccg tgg gaa tgt ttc aaa gaa ggt      49
  Met Trp Gly Ala Cys Trp Pro Phe Pro Trp Glu Cys Phe Lys Glu Gly
  1               5                   10                  15 gga ggc ggt ggg g                                                      62
Gly Gly Gly Gly
            20
```

<210> SEQ ID NO 6
<211> LENGTH: 20
<212> TYPE: PRT
<213> ORGANISM: Artificial Sequence
<220> FEATURE:
<223> OTHER INFORMATION: NdeI to SalI fragment

<400> SEQUENCE: 6

Met Trp Gly Ala Cys Trp Pro Phe Pro Trp Glu Cys Phe Lys Glu Gly
1               5                   10                  15

Gly Gly Gly Gly
            20

<210> SEQ ID NO 7

```
<211> LENGTH: 62
<212> TYPE: DNA
<213> ORGANISM: Artificial Sequence
<220> FEATURE:
<223> OTHER INFORMATION: NdeI to SalI fragment
<220> FEATURE:
<221> NAME/KEY: CDS
<222> LOCATION: (2)..(61)

<400> SEQUENCE: 7 t atg gtt ccg ttc tgt gac ctg ctg act aaa cac tgt ttc gaa gct ggt    49
  Met Val Pro Phe Cys Asp Leu Leu Thr Lys His Cys Phe Glu Ala Gly
  1               5                  10                  15 gga ggc ggt ggg g                                                    62
Gly Gly Gly Gly
        20

<210> SEQ ID NO 8
<211> LENGTH: 20
<212> TYPE: PRT
<213> ORGANISM: Artificial Sequence
<220> FEATURE:
<223> OTHER INFORMATION: NdeI to SalI fragment

<400> SEQUENCE: 8

Met Val Pro Phe Cys Asp Leu Leu Thr Lys His Cys Phe Glu Ala Gly
1               5                  10                  15

Gly Gly Gly Gly
        20

<210> SEQ ID NO 9
<211> LENGTH: 74
<212> TYPE: DNA
<213> ORGANISM: Artificial Sequence
<220> FEATURE:
<223> OTHER INFORMATION: NdeI to SalI fragment
<220> FEATURE:
<221> NAME/KEY: CDS
<222> LOCATION: (2)..(73)

<400> SEQUENCE: 9 t atg ggt tct cgt tgt aaa tac aaa tgg gac gtt ctg act aaa cag tgt    49
  Met Gly Ser Arg Cys Lys Tyr Lys Trp Asp Val Leu Thr Lys Gln Cys
  1               5                  10                  15 ttc cac cac ggt gga ggc ggt ggg g                                    74
Phe His His Gly Gly Gly Gly Gly
        20

<210> SEQ ID NO 10
<211> LENGTH: 24
<212> TYPE: PRT
<213> ORGANISM: Artificial Sequence
<220> FEATURE:
<223> OTHER INFORMATION: NdeI to SalI fragment

<400> SEQUENCE: 10

Met Gly Ser Arg Cys Lys Tyr Lys Trp Asp Val Leu Thr Lys Gln Cys
1               5                  10                  15

Phe His His Gly Gly Gly Gly Gly
        20

<210> SEQ ID NO 11
<211> LENGTH: 74
<212> TYPE: DNA
<213> ORGANISM: Artificial Sequence
<220> FEATURE:
<223> OTHER INFORMATION: NdeI to SalI fragment
<220> FEATURE:
```

```
<221> NAME/KEY: CDS
<222> LOCATION: (2)..(73)

<400> SEQUENCE: 11 t atg ctg ccg ggt tgt aaa tgg gac ctg ctg atc aaa cag tgg gtt tgt      49
  Met Leu Pro Gly Cys Lys Trp Asp Leu Leu Ile Lys Gln Trp Val Cys
  1               5                  10                  15 gac ccg ctg ggt gga ggc ggt ggg g                                      74
Asp Pro Leu Gly Gly Gly Gly Gly
            20

<210> SEQ ID NO 12
<211> LENGTH: 24
<212> TYPE: PRT
<213> ORGANISM: Artificial Sequence
<220> FEATURE:
<223> OTHER INFORMATION: NdeI to SalI fragment

<400> SEQUENCE: 12

Met Leu Pro Gly Cys Lys Trp Asp Leu Leu Ile Lys Gln Trp Val Cys
1               5                  10                  15

Asp Pro Leu Gly Gly Gly Gly Gly
            20

<210> SEQ ID NO 13
<211> LENGTH: 74
<212> TYPE: DNA
<213> ORGANISM: Artificial Sequence
<220> FEATURE:
<223> OTHER INFORMATION: NdeI to SalI fragment
<220> FEATURE:
<221> NAME/KEY: CDS
<222> LOCATION: (2)..(73)

<400> SEQUENCE: 13 t atg tct gct gac tgt tac ttc gac atc ctg act aaa tct gac gtt tgt      49
  Met Ser Ala Asp Cys Tyr Phe Asp Ile Leu Thr Lys Ser Asp Val Cys
  1               5                  10                  15 act tct tct ggt gga ggc ggt ggg g                                      74
Thr Ser Ser Gly Gly Gly Gly Gly
            20

<210> SEQ ID NO 14
<211> LENGTH: 24
<212> TYPE: PRT
<213> ORGANISM: Artificial Sequence
<220> FEATURE:
<223> OTHER INFORMATION: NdeI to SalI fragment

<400> SEQUENCE: 14

Met Ser Ala Asp Cys Tyr Phe Asp Ile Leu Thr Lys Ser Asp Val Cys
1               5                  10                  15

Thr Ser Ser Gly Gly Gly Gly Gly
            20

<210> SEQ ID NO 15
<211> LENGTH: 74
<212> TYPE: DNA
<213> ORGANISM: Artificial Sequence
<220> FEATURE:
<223> OTHER INFORMATION: NdeI to SalI fragment
<220> FEATURE:
<221> NAME/KEY: CDS
<222> LOCATION: (2)..(73)

<400> SEQUENCE: 15 t atg tct gac gac tgt atg tac gac cag ctg act cgt atg ttc atc tgt      49
```

```
    Met Ser Asp Asp Cys Met Tyr Asp Gln Leu Thr Arg Met Phe Ile Cys
    1               5                   10                  15 tct aac ctg ggt gga ggc ggt ggg g                                       74
Ser Asn Leu Gly Gly Gly Gly Gly
        20

<210> SEQ ID NO 16
<211> LENGTH: 24
<212> TYPE: PRT
<213> ORGANISM: Artificial Sequence
<220> FEATURE:
<223> OTHER INFORMATION: NdeI to SalI fragment

<400> SEQUENCE: 16

Met Ser Asp Asp Cys Met Tyr Asp Gln Leu Thr Arg Met Phe Ile Cys
1               5                   10                  15

Ser Asn Leu Gly Gly Gly Gly Gly
        20

<210> SEQ ID NO 17
<211> LENGTH: 76
<212> TYPE: DNA
<213> ORGANISM: Artificial Sequence
<220> FEATURE:
<223> OTHER INFORMATION: NdeI to SalI fragment
<220> FEATURE:
<221> NAME/KEY: CDS
<222> LOCATION: (2)..(73)

<400> SEQUENCE: 17 t atg gac ctg aac tgt aaa tac gac gaa ctg act tac aaa gaa tgg tgt      49
  Met Asp Leu Asn Cys Lys Tyr Asp Glu Leu Thr Tyr Lys Glu Trp Cys
  1               5                   10                  15 cag ttc aac ggg gtg gag gcg gtg ggg                                    76
Gln Phe Asn Gly Val Glu Ala Val
        20

<210> SEQ ID NO 18
<211> LENGTH: 24
<212> TYPE: PRT
<213> ORGANISM: Artificial Sequence
<220> FEATURE:
<223> OTHER INFORMATION: NdeI to SalI fragment

<400> SEQUENCE: 18

Met Asp Leu Asn Cys Lys Tyr Asp Glu Leu Thr Tyr Lys Glu Trp Cys
1               5                   10                  15

Gln Phe Asn Gly Val Glu Ala Val
        20

<210> SEQ ID NO 19
<211> LENGTH: 74
<212> TYPE: DNA
<213> ORGANISM: Artificial Sequence
<220> FEATURE:
<223> OTHER INFORMATION: NdeI to SalI fragment
<220> FEATURE:
<221> NAME/KEY: CDS
<222> LOCATION: (2)..(73)

<400> SEQUENCE: 19 t atg ttc cac gac tgt aaa tac gac ctg ctg act cgt cag atg gtt tgt      49
  Met Phe His Asp Cys Lys Tyr Asp Leu Leu Thr Arg Gln Met Val Cys
  1               5                   10                  15 cac ggt ctg ggt gga ggc ggt ggg g                                      74
His Gly Leu Gly Gly Gly Gly Gly
        20
```

```
<210> SEQ ID NO 20
<211> LENGTH: 24
<212> TYPE: PRT
<213> ORGANISM: Artificial Sequence
<220> FEATURE:
<223> OTHER INFORMATION: NdeI to SalI fragment

<400> SEQUENCE: 20

Met Phe His Asp Cys Lys Tyr Asp Leu Leu Thr Arg Gln Met Val Cys
1               5                   10                  15
His Gly Leu Gly Gly Gly Gly Gly
            20

<210> SEQ ID NO 21
<211> LENGTH: 74
<212> TYPE: DNA
<213> ORGANISM: Artificial Sequence
<220> FEATURE:
<223> OTHER INFORMATION: NdeI to SalI fragment
<220> FEATURE:
<221> NAME/KEY: CDS
<222> LOCATION: (2)..(73)

<400> SEQUENCE: 21 t atg cgt aac cac tgt ttc tgg gac cac ctg ctg aaa cag gac atc tgt        49
  Met Arg Asn His Cys Phe Trp Asp His Leu Leu Lys Gln Asp Ile Cys
  1               5                   10                  15 ccg tct ccg ggt gga ggc ggt ggg g                                        74
Pro Ser Pro Gly Gly Gly Gly Gly
            20

<210> SEQ ID NO 22
<211> LENGTH: 24
<212> TYPE: PRT
<213> ORGANISM: Artificial Sequence
<220> FEATURE:
<223> OTHER INFORMATION: NdeI to SalI fragment

<400> SEQUENCE: 22

Met Arg Asn His Cys Phe Trp Asp His Leu Leu Lys Gln Asp Ile Cys
1               5                   10                  15
Pro Ser Pro Gly Gly Gly Gly Gly
            20

<210> SEQ ID NO 23
<211> LENGTH: 74
<212> TYPE: DNA
<213> ORGANISM: Artificial Sequence
<220> FEATURE:
<223> OTHER INFORMATION: NdeI to SalI fragment
<220> FEATURE:
<221> NAME/KEY: CDS
<222> LOCATION: (2)..(73)

<400> SEQUENCE: 23 t atg gct aac cag tgt tgg tgg gac tct ctg ctg aaa aaa aac gtt tgt        49
  Met Ala Asn Gln Cys Trp Trp Asp Ser Leu Leu Lys Lys Asn Val Cys
  1               5                   10                  15 gaa ttc ttc ggt gga ggc ggt ggg g                                        74
Glu Phe Phe Gly Gly Gly Gly Gly
            20

<210> SEQ ID NO 24
<211> LENGTH: 24
<212> TYPE: PRT
<213> ORGANISM: Artificial Sequence
```

```
<220> FEATURE:
<223> OTHER INFORMATION: NdeI to SalI fragment

<400> SEQUENCE: 24

Met Ala Asn Gln Cys Trp Trp Asp Ser Leu Leu Lys Lys Asn Val Cys
1               5                   10                  15

Glu Phe Phe Gly Gly Gly Gly Gly
            20

<210> SEQ ID NO 25
<211> LENGTH: 74
<212> TYPE: DNA
<213> ORGANISM: Artificial Sequence
<220> FEATURE:
<223> OTHER INFORMATION: NdeI to SalI fragment
<220> FEATURE:
<221> NAME/KEY: CDS
<222> LOCATION: (2)..(73)

<400> SEQUENCE: 25 t atg ttc cac gac tgc aaa tgg gac ctg ctg acc aaa cag tgg gtt tgc    49
  Met Phe His Asp Cys Lys Trp Asp Leu Leu Thr Lys Gln Trp Val Cys
  1               5                   10                  15 cac ggt ctg ggt gga ggc ggt ggg g                                    74
His Gly Leu Gly Gly Gly Gly Gly
            20

<210> SEQ ID NO 26
<211> LENGTH: 24
<212> TYPE: PRT
<213> ORGANISM: Artificial Sequence
<220> FEATURE:
<223> OTHER INFORMATION: NdeI to SalI fragment

<400> SEQUENCE: 26

Met Phe His Asp Cys Lys Trp Asp Leu Leu Thr Lys Gln Trp Val Cys
1               5                   10                  15

His Gly Leu Gly Gly Gly Gly Gly
            20

<210> SEQ ID NO 27

<400> SEQUENCE: 27

000

<210> SEQ ID NO 28
<211> LENGTH: 7285
<212> TYPE: DNA
<213> ORGANISM: Artificial Sequence
<220> FEATURE:
<223> OTHER INFORMATION: pAMG21-RANK-Fc vector

<400> SEQUENCE: 28
gatcagcagt ccccggaaca tcgtagctga cgccttcgcg ttgctcagtt gtccaacccc     60
ggaaacggga aaagcaagt tttccccgct cccggcgttt caataactga aaaccatact    120
atttcacagt ttaaatcaca ttaaacgaca gtaatccccg ttgatttgtg cgccaacaca    180
gatcttcgtc acaattctca agtcgctgat ttcaaaaaac tgtagtatcc tctgcgaaac    240
gatccctgtt tgagtattga ggaggcgaga tgtcgcagac agaaaatgca gtgacttcct    300
cattgagtca aaagcggttt gtgcgcagag gtaagcctat gactgactct gagaaacaaa    360
tggccgttgt tgcaagaaaa cgtcttacac acaaagagat aaaagttttt gtcaaaaatc    420
ctctgaagga tctcatggtt gagtactgcg agagagaggg gataacacag gctcagttcg    480
```

```
ttgagaaaat catcaaagat gaactgcaaa gactggatat actaaagtaa agactttact    540
ttgtggcgta gcatgctaga ttactgatcg tttaaggaat tttgtggctg ccacgccgt     600 aaggtggcaa ggaactggtt ctgatgtgga tttacaggag ccagaaaagc aaaaaccccg    660
ataatcttct tcaacttttg cgagtacgaa aagattaccg gggcccactt aaaccgtata    720
gccaacaatt cagctatgcg gggagtatag ttatatgccc ggaaaagttc aagacttctt    780
tctgtgctcg ctccttctgc gcattgtaag tgcaggatgg tgtgactgat cttcaccaaa    840
cgtattaccg ccaggtaaag aacccgaatc cggtgtttac accccgtgaa ggtgcaggaa    900
cgctgaagtt ctgcgaaaaa ctgatggaaa aggcggtggg cttcacttcc cgttttgatt    960
tcgccattca tgtggcgcac gcccgttcgc gtgatctgcg tcgccgtatg ccaccagtgc    1020
tgcgtcgtcg ggctattgat gcgctcttgc aggggctgtg tttccactat gacccgctgg    1080
ccaaccgcgt ccagtgctcc atcaccacgc tggccattga gtgcggactg gcgacggagt    1140
ctgctgccgg aaaactctcc atcacccgtg ccacccgtgc cctgacgttc ctgtcagagc    1200
tgggactgat tacctaccag acggaatatg acccgcttat cgggtgctac attccgaccg    1260
atatcacgtt cacatctgca ctgtttgctg ccctcgatgt atcagaggag gcagtggccg    1320
ccgcgcgccg cagccgtgtg gtatgggaaa acaaacaacg caaaaagcag gggctggata    1380
ccctgggcat ggatgaactg atagcgaaag cctggcgttt tgttcgtgag cgttttcgca    1440
gttatcagac agagcttaag tcccgtggaa taaagcgtgc ccgtgcgcgt cgtgatgcgg    1500
acagggaacg tcaggatatt gtcaccctgg tgaaacggca gctgacgcgc gaaatcgcgg    1560
aagggcgctt cactgccaat cgtgaggcgg taaaacgcga agttgagcgt cgtgtgaagg    1620
agcgcatgat tctgtcacgt aaccgtaatt acagccggct ggccacagct tcccctgaa    1680 agtgacctcc tctgaataat ccggcctgcg ccggaggctt ccgcacgtct gaagcccgac    1740
agcgcacaaa aaatcagcac cacatacaaa aaacaacctc atcatccagc ttctggtgca    1800
tccggccccc cctgttttcg atacaaaaca cgcctcacag acggggaatt tgcttatcc    1860 acattaaact gcaagggact tccccataag gttacaaccg ttcatgtcat aaagcgccat    1920
ccgccagcgt tacagggtgc aatgtatctt ttaaacacct gtttatatct cctttaaact    1980
acttaattac attcatttaa aaagaaaacc tattcactgc ctgtccttgg acagacagat    2040
atgcacctcc caccgcaagc ggcgggcccc taccggagcc gctttagtta caacactcag    2100
acacaaccac cagaaaaacc ccggtccagc gcagaactga aaccacaaag cccctcccte    2160 ataactgaaa agcggccccg ccccggtccg aagggccgga acagagtcgc ttttaattat    2220
gaatgttgta actacttcat catcgctgtc agtcttctcg ctggaagttc tcagtacacg    2280
ctcgtaagcg gccctgacgg cccgctaacg cggagatacg ccccgacttc gggtaaaccc    2340
tcgtcgggac cactccgacc gcgcacagaa gctctctcat ggctgaaagc gggtatggtc    2400
tggcagggct ggggatgggt aaggtgaaat ctatcaatca gtaccggctt acgccgggct    2460
tcggcggttt tactcctgtt tcatatatga acaacaggt caccgccttc catgccgctg      2520
atgcggcata tcctggtaac gatatctgaa ttgttataca tgtgtatata cgtggtaatg    2580
acaaaaatag gacaagttaa aaatttacag gcgatgcaat gattcaaaca cgtaatcaat    2640 atcggggtg ggcgaagaac tccagcatga atcccccgcg ctggaggatc atccagccgg      2700
cgtcccggaa aacgattccg aagcccaacc tttcatagaa ggcggcggtg gaatcgaaat    2760
ctcgtgatgg caggttgggc gtcgcttggt cggtcatttc gaaccccaga gtcccgctca    2820
gaagaactcg tcaagaaggc gatagaaggc gatgcgctgc gaatcgggag cggcgatacc    2880
```

```
gtaaagcacg aggaagcggt cagcccattc gccgccaagc tcttcagcaa tatcacgggt   2940
agccaacgct atgtcctgat agcggtccgc cacacccagc cggccacagt cgatgaatcc   3000
agaaaagcgg ccattttcca ccatgatatt cggcaagcag gcatcgccat gagtcacgac   3060
gagatcctcg ccgtcgggca tgcgcgcctt gagcctggcg aacagttcgg ctggcgcgag   3120
cccctgatgc tcttcgtcca gatcatcctg atcgacaaga ccggcttcca tccgagtacg   3180
tgctcgctcg atgcgatgtt tcgcttggtg gtcgaatggg caggtagccg gatcaagcgt   3240
atgcagccgc cgcattgcat cagccatgat ggatactttc tcggcaggag caaggtgaga   3300
tgacaggaga tcctgccccg gcacttcgcc caatagcagc cagtcccttc ccgcttcagt   3360
gacaacgtcg agcacagctg cgcaaggaac gcccgtcgtg gccagccacg atagccgcgc   3420
tgcctcgtcc tgcaattcat tcaggacacc ggacaggtcg gtcttgacaa aaagaaccgg   3480
gcgcccctgc gctgacagcc ggaacacggc ggcatcagag cagccgattg tctgttgtgc   3540
ccagtcatag ccgaatagcc tctccaccca agcggccgga gaacctgcgt gcaatccatc   3600
ttgttcaatc atgcgaaacg atcctcatcc tgtctcttga tctgatcttg atcccctgcg   3660
ccatcagatc cttggcggca agaaagccat ccagtttact ttgcagggct tcccaacctt   3720
accagagggc gccccagctg gcaattccgg ttcgcttgct gtccataaaa ccgcccagtc   3780
tagctatcgc catgtaagcc cactgcaagc tacctgcttt ctctttgcgc ttgcgttttc   3840
ccttgtccag atagcccagt agctgacatt catccggggt cagcaccgtt tctgcggact   3900
ggctttctac gtgttccgct tccttttagca gcccttgcgc cctgagtgct gcggcagcg   3960 tgaagctaca tatatgtgat ccgggcaaat cgctgaatat tccttttgtc tccgaccatc   4020
aggcacctga gtcgctgtct ttttcgtgac attcagttcg ctgcgctcac ggctctggca   4080
gtgaatgggg gtaaatggca ctacaggcgc cttttatgga ttcatgcaag gaaactaccc   4140
ataatacaag aaaagcccgt cacgggcttc tcagggcgtt ttatggcggg tctgctatgt   4200
ggtgctatct gactttttgc tgttcagcag ttcctgccct ctgattttcc agtctgacca   4260
cttcggatta tcccgtgaca ggtcattcag actggctaat gcacccagta aggcagcggt   4320
atcatcaaca ggcttacccg tcttactgtc gaagacgtgc gtaacgtatg catggtctcc   4380
ccatgcgaga gtagggaact gccaggcatc aaataaaacg aaaggctcag tcgaaagact   4440
gggcctttcg ttttatctgt tgtttgtcgg tgaacgctct cctgagtagg acaaatccgc   4500
cgggagcgga tttgaacgtt gcgaagcaac ggcccgagg gtggcgggca ggacgcccgc   4560
cataaactgc caggcatcaa attaagcaga aggccatcct gacggatggc cttttgcgt   4620 ttctacaaac tcttttgttt attttttctaa atacattcaa atatggacgt cgtacttaac   4680
ttttaaagta tgggcaatca attgctcctg ttaaaattgc tttagaaata ctttggcagc   4740
ggtttgttgt attgagtttc atttgcgcat tggttaaatg gaaagtgacc gtgcgcttac   4800
tacagcctaa tattttgaa atatcccaag agcttttcc ttcgcatgcc cacgctaaac   4860
attctttttc tcttttggtt aaatcgttgt tgatttatt atttgctata tttatttttc   4920
gataattatc aactagagaa ggaacaatta atggtatgtt catacacgca tgtaaaaata   4980
aactatctat atagttgtct ttctctgaat gtgcaaaact aagcattccg aagccattat   5040
tagcagtatg aataggaaaa ctaaacccag tgataagacc tgatgatttc gcttctttaa   5100
ttacatttgg agattttta tttacagcat tgttttcaaa tatattccaa ttaatcggtg   5160
aatgattgga gttagaataa tctactatag gatcatattt tattaaatta gcgtcatcat   5220
aatattgcct ccattttta gggtaattat ccagaattga aatatcagat ttaaccatag   5280
```

```
aatgaggata aatgatcgcg agtaaataat attcacaatg taccatttta gtcatatcag   5340
ataagcattg attaatatca ttattgcttc tacaggcttt aattttatta attattctgt   5400
aagtgtcgtc ggcatttatg tctttcatac ccatctcttt atccttacct attgtttgtc   5460
gcaagttttg cgtgttatat atcattaaaa cggtaataga ttgacatttg attctaataa   5520
attggatttt tgtcacacta ttatatcgct tgaaatacaa ttgtttaaca taagtacctg   5580
taggatcgta caggtttacg caagaaaatg gtttgttata gtcgattaat cgatttgatt   5640
ctagatttgt tttaactaat taaggagga ataacatatg atcgctccac catgcaccag   5700
tgagaagcat tatgagcatc tgggacggtg ctgtaacaaa tgtgaaccag gaaagtacat   5760
gtcttctaaa tgcactacta cctctgacag tgtatgtctg ccctgtggcc cggatgaata   5820
cttggatagc tggaatgaag aagataaatg cttgctgcat aaagtttgtg atacaggcaa   5880
ggccctggtg gccgtggtcg ccggcaacag tacgaccccc cggcgctgcg cgtgcacggc   5940
tgggtaccac tggagccagg actgcgagtg ctgccgccgc aacaccgagt gcgcgccggg   6000
cctgggcgcc cagcacccgt tgcagctcaa caaggacaca gtgtgcaaac cttgccttgc   6060
aggctacttc tctgatgcct tttcctccac ggacaaatgc agaccctgga ccaactgtac   6120
cttccttgga aagagagtag aacatcatgg gacagagaaa tccgatgtgg tttgcagttc   6180
ttctctgcca gctagaaaac caccaaatga accccatgtt tacgtcgaca aaactcacac   6240
atgtccacct tgtccagctc cggaactcct gggggaccg tcagtcttcc tcttcccccc   6300
aaaacccaag gacaccctca tgatctcccg gacccctgag gtcacatgcg tggtggtgga   6360
cgtgagccac gaagaccctg aggtcaagtt caactggtac gtggacggcg tggaggtgca   6420
taatgccaag acaaagccgc gggaggagca gtacaacagc acgtaccgtg tggtcagcgt   6480
cctcaccgtc ctgcaccagg actggctgaa tggcaaggag tacaagtgca aggtctccaa   6540
caaagccctc ccagccccca tcgagaaaac catctccaaa gccaaagggc agccccgaga   6600
accacaggtg tacaccctgc ccccatcccg ggatgagctg accaagaacc aggtcagcct   6660
gacctgcctg gtcaaaggct tctatcccag cgacatcgcc gtggagtggg agagcaatgg   6720
gcagccggag aacaactaca agaccacgcc tcccgtgctg gactccgacg gctccttctt   6780
cctctacagc aagctcaccg tggacaagag caggtggcag caggggaacg tcttctcatg   6840
ctccgtgatg catgaggctc tgcacaacca ctacacgcag aagagcctct ccctgtctcc   6900
gggtaaataa tggatccgcg gaagaagaa gaagaagaag aaagcccgaa aggaagctga   6960
gttggctgct gccaccgctg agcaataact agcataaccc cttggggcct ctaaacgggt   7020
cttgagggggt ttttttgctga aaggaggaac cgctcttcac gctcttcacg cggataaata   7080
agtaacgatc cggtccagta atgacctcag aactccatct ggatttgttc agaacgctcg   7140
gttgccgccg ggcgtttttt attggtgaga atcgcagcaa cttgtcgcgc caatcgagcc   7200
atgtcgtcgt caacgacccc ccattcaaga acagcaagca gcattgagaa cttggaatc   7260
cagtccctct tccacctgct gaccg                                        7285
```

<210> SEQ ID NO 29
<211> LENGTH: 14
<212> TYPE: PRT
<213> ORGANISM: Artificial Sequence
<220> FEATURE:
<223> OTHER INFORMATION: Preferred TALL-1 modulating domain

<400> SEQUENCE: 29

Pro Gly Thr Cys Phe Pro Phe Pro Trp Glu Cys Thr His Ala

-continued

<210> SEQ ID NO 30
<211> LENGTH: 14
<212> TYPE: PRT
<213> ORGANISM: Artificial Sequence
<220> FEATURE:
<223> OTHER INFORMATION: Preferred TALL-1 modulating domain

<400> SEQUENCE: 30

Trp Gly Ala Cys Trp Pro Phe Pro Trp Glu Cys Phe Lys Glu
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Preferred TALL-1 modulating domain

<400> SEQUENCE: 31

Val Pro Phe Cys Asp Leu Leu Thr Lys His Cys Phe Glu Ala
1               5                   10

<210> SEQ ID NO 32
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 32

Gly Ser Arg Cys Lys Tyr Lys Trp Asp Val Leu Thr Lys Gln Cys Phe
1 5 10 15

His His

<210> SEQ ID NO 33
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 33

Leu Pro Gly Cys Lys Trp Asp Leu Leu Ile Lys Gln Trp Val Cys Asp
1 5 10 15

Pro Leu

<210> SEQ ID NO 34
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 34

Ser Ala Asp Cys Tyr Phe Asp Ile Leu Thr Lys Ser Asp Val Cys Thr
1 5 10 15

Ser Ser

<210> SEQ ID NO 35
<211> LENGTH: 18
<212> TYPE: PRT
<213> ORGANISM: Artificial Sequence
<220> FEATURE:
<223> OTHER INFORMATION: Preferred TALL-1 modulating domain

```
<400> SEQUENCE: 35

Ser Asp Asp Cys Met Tyr Asp Gln Leu Thr Arg Met Phe Ile Cys Ser
1               5                   10                  15

Asn Leu

<210> SEQ ID NO 36
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 36

Asp Leu Asn Cys Lys Tyr Asp Glu Leu Thr Tyr Lys Glu Trp Cys Gln
1               5                   10                  15

Phe Asn

<210> SEQ ID NO 37
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 37

Phe His Asp Cys Lys Tyr Asp Leu Leu Thr Arg Gln Met Val Cys His
1               5                   10                  15

Gly Leu

<210> SEQ ID NO 38
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 38

Arg Asn His Cys Phe Trp Asp His Leu Leu Lys Gln Asp Ile Cys Pro
1               5                   10                  15

Ser Pro

<210> SEQ ID NO 39
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 39

Ala Asn Gln Cys Trp Trp Asp Ser Leu Thr Lys Lys Asn Val Cys Glu
1               5                   10                  15

Phe Phe

<210> SEQ ID NO 40
<211> LENGTH: 8
<212> TYPE: PRT
<213> ORGANISM: Artificial Sequence
<220> FEATURE:
<223> OTHER INFORMATION: Polyglycine linker

<400> SEQUENCE: 40

Gly Gly Gly Lys Gly Gly Gly Gly
1               5
```

```
<210> SEQ ID NO 41
<211> LENGTH: 8
<212> TYPE: PRT
<213> ORGANISM: Artificial Sequence
<220> FEATURE:
<223> OTHER INFORMATION: Polyglycine linker

<400> SEQUENCE: 41

Gly Gly Gly Asn Gly Ser Gly Gly
1               5

<210> SEQ ID NO 42
<211> LENGTH: 8
<212> TYPE: PRT
<213> ORGANISM: Artificial Sequence
<220> FEATURE:
<223> OTHER INFORMATION: Polyglycine linker

<400> SEQUENCE: 42

Gly Gly Gly Cys Gly Gly Gly Gly
1               5

<210> SEQ ID NO 43
<211> LENGTH: 5
<212> TYPE: PRT
<213> ORGANISM: Artificial Sequence
<220> FEATURE:
<223> OTHER INFORMATION: Polyglycine linker

<400> SEQUENCE: 43

Gly Pro Asn Gly Gly
1               5

<210> SEQ ID NO 44
<211> LENGTH: 19
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (19)..(19)
<223> OTHER INFORMATION: Linker or peptide bond linked to Fc domain

<400> SEQUENCE: 44

Leu Pro Gly Cys Lys Trp Asp Leu Leu Ile Lys Gln Trp Val Cys Asp
1               5                   10                  15

Pro Leu Xaa

<210> SEQ ID NO 45
<211> LENGTH: 19
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Linker or peptide bond linked to Fc domain

<400> SEQUENCE: 45

Xaa Leu Pro Gly Cys Lys Trp Asp Leu Leu Ile Lys Gln Trp Val Cys
1               5                   10                  15

Asp Pro Leu

<210> SEQ ID NO 46
```

```
<211> LENGTH: 38
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (19)..(19)
<223> OTHER INFORMATION: Linker or peptide bond
<220> FEATURE:
<221> NAME/KEY: MISC_FEATURE
<222> LOCATION: (38)..(38)
<223> OTHER INFORMATION: Linker or peptide bond linked to Fc domain

<400> SEQUENCE: 46

Leu Pro Gly Cys Lys Trp Asp Leu Leu Ile Lys Gln Trp Val Cys Asp
 1               5                  10                  15
Pro Leu Xaa Leu Pro Gly Cys Lys Trp Asp Leu Leu Ile Lys Gln Trp
             20                  25                  30
Val Cys Asp Pro Leu Xaa
             35

<210> SEQ ID NO 47
<211> LENGTH: 38
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Linker or peptide bond linked to Fc domain
<220> FEATURE:
<221> NAME/KEY: MISC_FEATURE
<222> LOCATION: (20)..(20)
<223> OTHER INFORMATION: Linker or peptide bond

<400> SEQUENCE: 47

Xaa Leu Pro Gly Cys Lys Trp Asp Leu Leu Ile Lys Gln Trp Val Cys
 1               5                  10                  15
Asp Pro Leu Xaa Leu Pro Gly Cys Lys Trp Asp Leu Leu Ile Lys Gln
             20                  25                  30
Trp Val Cys Asp Pro Leu
             35

<210> SEQ ID NO 48
<211> LENGTH: 19
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (19)..(19)
<223> OTHER INFORMATION: Linker or peptide bond linked to Fc domain

<400> SEQUENCE: 48

Ser Ala Asp Cys Tyr Phe Asp Ile Leu Thr Lys Ser Asp Val Cys Thr
 1               5                  10                  15
Ser Ser Xaa

<210> SEQ ID NO 49
<211> LENGTH: 19
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
```

```
<222> LOCATION: (1)..(1)
<223> OTHER INFORMATION: Linker or peptide bond linked to Fc domain

<400> SEQUENCE: 49

Xaa Ser Ala Asp Cys Tyr Phe Asp Ile Leu Thr Lys Ser Asp Val Cys
1               5                   10                  15

Thr Ser Ser

<210> SEQ ID NO 50
<211> LENGTH: 36
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (18)..(18)
<223> OTHER INFORMATION: Linker or peptide bond
<220> FEATURE:
<221> NAME/KEY: MISC_FEATURE
<222> LOCATION: (36)..(36)
<223> OTHER INFORMATION: Linker or peptide bond linked to Fc domain

<400> SEQUENCE: 50

Ser Ala Asp Cys Tyr Phe Asp Ile Leu Thr Lys Ser Asp Val Thr Ser
1               5                   10                  15

Ser Xaa Ser Ala Asp Cys Tyr Phe Asp Ile Leu Thr Lys Ser Asp Val
            20                  25                  30

Thr Ser Ser Xaa
        35

<210> SEQ ID NO 51
<211> LENGTH: 36
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Linker or peptide bond linked to Fc domain
<220> FEATURE:
<221> NAME/KEY: MISC_FEATURE
<222> LOCATION: (19)..(19)
<223> OTHER INFORMATION: Linker or peptide bond

<400> SEQUENCE: 51

Xaa Ser Ala Asp Cys Tyr Phe Asp Ile Leu Thr Lys Ser Asp Val Thr
1               5                   10                  15

Ser Ser Xaa Ser Ala Asp Cys Tyr Phe Asp Ile Leu Thr Lys Ser Asp
            20                  25                  30

Val Thr Ser Ser
        35

<210> SEQ ID NO 52
<211> LENGTH: 19
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (19)..(19)
<223> OTHER INFORMATION: Linker or peptide bond linked to Fc domain

<400> SEQUENCE: 52

Phe His Asp Cys Lys Trp Asp Leu Leu Thr Lys Gln Trp Val Cys His
1               5                   10                  15
```

Gly Leu Xaa

<210> SEQ ID NO 53
<211> LENGTH: 19
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Linker or peptide bond linked to Fc domain

<400> SEQUENCE: 53

Xaa Phe His Asp Cys Lys Trp Asp Leu Leu Thr Lys Gln Trp Val Cys
1               5                   10                  15

His Gly Leu

<210> SEQ ID NO 54
<211> LENGTH: 38
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (19)..(19)
<223> OTHER INFORMATION: Linker or peptide bond
<220> FEATURE:
<221> NAME/KEY: MISC_FEATURE
<222> LOCATION: (38)..(38)
<223> OTHER INFORMATION: Linker or peptide bond linked to Fc domain

<400> SEQUENCE: 54

Phe His Asp Cys Lys Trp Asp Leu Leu Thr Lys Gln Trp Val Cys His
1               5                   10                  15

Gly Leu Xaa Phe His Asp Cys Lys Trp Asp Leu Leu Thr Lys Gln Trp
            20                  25                  30

Val Cys His Gly Leu Xaa
        35

<210> SEQ ID NO 55
<211> LENGTH: 38
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Linker or peptide bond linked to Fc domain
<220> FEATURE:
<221> NAME/KEY: MISC_FEATURE
<222> LOCATION: (20)..(20)
<223> OTHER INFORMATION: Linker or peptide bond

<400> SEQUENCE: 55

Xaa Phe His Asp Cys Lys Trp Asp Leu Leu Thr Lys Gln Trp Val Cys
1               5                   10                  15

His Gly Leu Xaa Phe His Asp Cys Lys Trp Asp Leu Leu Thr Lys Gln
            20                  25                  30

Trp Val Cys His Gly Leu
        35

<210> SEQ ID NO 56
<211> LENGTH: 25
<212> TYPE: DNA

```
<213> ORGANISM: Artificial Sequence
<220> FEATURE:
<223> OTHER INFORMATION: Oligonucleotide

<400> SEQUENCE: 56
cggcgcaact atcggtatca agctg                                               25

<210> SEQ ID NO 57
<211> LENGTH: 26
<212> TYPE: DNA
<213> ORGANISM: Artificial Sequence
<220> FEATURE:
<223> OTHER INFORMATION: Oligonucleotide

<400> SEQUENCE: 57
catgtaccgt aacactgagt ttcgtc                                              26

<210> SEQ ID NO 58
<211> LENGTH: 18
<212> TYPE: PRT
<213> ORGANISM: Artificial Sequence
<220> FEATURE:
<223> OTHER INFORMATION: Consensus peptide
<220> FEATURE:
<221> NAME/KEY: MISC_FEATURE
<222> LOCATION: (5)..(14)
<223> OTHER INFORMATION: Core amino acid sequence

<400> SEQUENCE: 58

Phe His Asp Cys Lys Trp Asp Leu Leu Thr Lys Gln Trp Val Cys His
1               5                   10                  15

Gly Leu

<210> SEQ ID NO 59
<211> LENGTH: 23
<212> TYPE: PRT
<213> ORGANISM: Artificial Sequence
<220> FEATURE:
<223> OTHER INFORMATION: Preferred linker sequence

<400> SEQUENCE: 59

Gly Ser Gly Ser Ala Thr Gly Gly Ser Gly Ser Thr Ala Ser Ser Gly
1               5                   10                  15

Ser Gly Ser Ala Thr His Met
            20

<210> SEQ ID NO 60
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 60

Asn Gln Thr Leu Trp Lys Trp Asp Leu Leu Thr Lys Gln Phe Ile Thr
1               5                   10                  15

Tyr Met

<210> SEQ ID NO 61
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 61
```

```
Pro Val Tyr Gln Gly Trp Trp Asp Thr Leu Thr Lys Leu Tyr Ile Trp
1               5                   10                  15

Asp Gly

<210> SEQ ID NO 62
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 62

Trp Leu Asp Gly Gly Trp Arg Asp Pro Leu Ile Lys Arg Ser Val Gln
1               5                   10                  15

Leu Gly

<210> SEQ ID NO 63
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 63

Gly His Gln Gln Phe Lys Trp Asp Leu Leu Thr Lys Gln Trp Val Gln
1               5                   10                  15

Ser Asn

<210> SEQ ID NO 64
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 64

Gln Arg Val Gly Gln Phe Trp Asp Val Leu Thr Lys Met Phe Ile Thr
1               5                   10                  15

Gly Ser

<210> SEQ ID NO 65
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 65

Gln Ala Gln Gly Trp Ser Tyr Asp Ala Leu Ile Lys Thr Trp Ile Arg
1               5                   10                  15

Trp Pro

<210> SEQ ID NO 66
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 66

Gly Trp Met His Trp Lys Trp Asp Pro Leu Thr Lys Gln Ala Leu Pro
1               5                   10                  15

Trp Met
```

<210> SEQ ID NO 67
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 67

Gly His Pro Thr Tyr Lys Trp Asp Leu Leu Thr Lys Gln Trp Ile Leu
1 5 10 15

Gln Met

<210> SEQ ID NO 68
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 68

Trp Asn Asn Trp Ser Leu Trp Asp Pro Leu Thr Lys Leu Trp Leu Gln
1 5 10 15

Gln Asn

<210> SEQ ID NO 69
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 69

Trp Gln Trp Gly Trp Lys Trp Asp Leu Leu Thr Lys Gln Trp Val Gln
1 5 10 15

Gln Gln

<210> SEQ ID NO 70
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 70

Gly Gln Met Gly Trp Arg Trp Asp Pro Leu Thr Lys Met Trp Leu Gly
1 5 10 15

Thr Ser

<210> SEQ ID NO 71
<211> LENGTH: 62
<212> TYPE: DNA
<213> ORGANISM: Artificial Sequence
<220> FEATURE:
<223> OTHER INFORMATION: Oligonucleotide 2517-24

<400> SEQUENCE: 71
tatgccgggt acttgtttcc cgttcccgtg ggaatgcact cacgctggtg gaggcggtgg 60
gg 62

<210> SEQ ID NO 72
<211> LENGTH: 64
<212> TYPE: DNA
<213> ORGANISM: Artificial Sequence
<220> FEATURE:

<223> OTHER INFORMATION: Oligonucleotide 2517-25

<400> SEQUENCE: 72
tcgaccccac cgcctcctgg agcgtgagtg cattcccacg ggaagccgaa acaagtaccc    60
ggca    64

<210> SEQ ID NO 73
<211> LENGTH: 62
<212> TYPE: DNA
<213> ORGANISM: Artificial Sequence
<220> FEATURE:
<223> OTHER INFORMATION: Oligonucleotide 2517-26

<400> SEQUENCE: 73
tatgtggggt gcttgttggc cgttcccgtg ggaatgtttc aaagaaggtg gaggcggtgg    60
gg    62

<210> SEQ ID NO 74
<211> LENGTH: 64
<212> TYPE: DNA
<213> ORGANISM: Artificial Sequence
<220> FEATURE:
<223> OTHER INFORMATION: Oligonucleotide 2517-27

<400> SEQUENCE: 74
tcgaccccac cgcctccacc ttctttgaaa cattcccacg ggaacggcca acaagcaccc    60
caca    64

<210> SEQ ID NO 75
<211> LENGTH: 62
<212> TYPE: DNA
<213> ORGANISM: Artificial Sequence
<220> FEATURE:
<223> OTHER INFORMATION: Oligonucleotide 2517-28

<400> SEQUENCE: 75
tatggttccg ttctgtgacc tgctgactaa acactgtttc gaagctggtg gaggcggtgg    60
gg    62

<210> SEQ ID NO 76
<211> LENGTH: 64
<212> TYPE: DNA
<213> ORGANISM: Artificial Sequence
<220> FEATURE:
<223> OTHER INFORMATION: Oligonucleotide 2517-29

<400> SEQUENCE: 76
tcgaccccac cgcctccacc agcttcgaaa cagtgtttag tcagcaggtc acagaacgga    60
acca    64

<210> SEQ ID NO 77
<211> LENGTH: 74
<212> TYPE: DNA
<213> ORGANISM: Artificial Sequence
<220> FEATURE:
<223> OTHER INFORMATION: Oligonucleotide 2517-30

<400> SEQUENCE: 77
tatgggttct cgttgtaaat acaaatggga cgttctgact aaacagtgtt tccaccacgg    60
tggaggcggt gggg    74

<210> SEQ ID NO 78

```
<211> LENGTH: 76
<212> TYPE: DNA
<213> ORGANISM: Artificial Sequence
<220> FEATURE:
<223> OTHER INFORMATION: Oligonucleotide 2517-31

<400> SEQUENCE: 78
tcgaccccac cgcctccacc gtggtggaaa cactgtttag tcagaacgtc ccatttgtat      60
ttacaacgag aaccca                                                     76

<210> SEQ ID NO 79
<211> LENGTH: 74
<212> TYPE: DNA
<213> ORGANISM: Artificial Sequence
<220> FEATURE:
<223> OTHER INFORMATION: Oligonucleotide 2517-32

<400> SEQUENCE: 79
tatgctgccg ggttgtaaat gggacctgct gatcaaacag tgggtttgtg acccgctggg      60
tggaggcggt gggg                                                       74

<210> SEQ ID NO 80
<211> LENGTH: 76
<212> TYPE: DNA
<213> ORGANISM: Artificial Sequence
<220> FEATURE:
<223> OTHER INFORMATION: Oligonucleotide 2517-33

<400> SEQUENCE: 80
tcgaccccac cgcctccacc cagcgggtca caaacccact gtttgatcag caggtcccat      60
ttacaacccg gcagca                                                     76

<210> SEQ ID NO 81
<211> LENGTH: 74
<212> TYPE: DNA
<213> ORGANISM: Artificial Sequence
<220> FEATURE:
<223> OTHER INFORMATION: Oligonucleotide 2517-34

<400> SEQUENCE: 81
tatgtctgct gactgttact tcgacatcct gactaaatct gacgtttgta cttcttctgg      60
tggaggcggt gggg                                                       74

<210> SEQ ID NO 82
<211> LENGTH: 76
<212> TYPE: DNA
<213> ORGANISM: Artificial Sequence
<220> FEATURE:
<223> OTHER INFORMATION: Oligonucleotide 2517-35

<400> SEQUENCE: 82
tcgaccccac cgcctccacc agaagaagta caaacgtcag atttagtcag gatgtcgaag      60
taacagtcag cagaca                                                     76

<210> SEQ ID NO 83
<211> LENGTH: 74
<212> TYPE: DNA
<213> ORGANISM: Artificial Sequence
<220> FEATURE:
<223> OTHER INFORMATION: Oligonucleotide 2517-36

<400> SEQUENCE: 83
tatgtctgac gactgtatgt acgaccagct gactcgtatg ttcatctgtt ctaacctggg      60
```

-continued tggaggcggt gggg                                               74

<210> SEQ ID NO 84
<211> LENGTH: 76
<212> TYPE: DNA
<213> ORGANISM: Artificial Sequence
<220> FEATURE:
<223> OTHER INFORMATION: Oligonucleotide 2517-37

<400> SEQUENCE: 84
tcgaccccac cgcctccacc caggttagaa cagatgaaca tacgagtcag ctggtcgtac    60
atacagtcgt cagaca                                             76

<210> SEQ ID NO 85
<211> LENGTH: 74
<212> TYPE: DNA
<213> ORGANISM: Artificial Sequence
<220> FEATURE:
<223> OTHER INFORMATION: Oligonucleotide 2521-92

<400> SEQUENCE: 85
tatggacctg aactgtaaat acgacgaact gacttacaaa gaatggtgtc agttcaacgg    60
tggaggcggt gggg                                               74

<210> SEQ ID NO 86
<211> LENGTH: 76
<212> TYPE: DNA
<213> ORGANISM: Artificial Sequence
<220> FEATURE:
<223> OTHER INFORMATION: Oligonucleotide 2521-93

<400> SEQUENCE: 86
tcgaccccac cgcctccacc gttgaactga caccattctt tgtaagtcag ttcgtcgtat    60
ttacagttca ggtcca                                             76

<210> SEQ ID NO 87
<211> LENGTH: 74
<212> TYPE: DNA
<213> ORGANISM: Artificial Sequence
<220> FEATURE:
<223> OTHER INFORMATION: Oligonucleotide 2521-94

<400> SEQUENCE: 87
tatgttccac gactgtaaat acgacctgct gactcgtcag atggtttgtc acggtctggg    60
tggaggcggt gggg                                               74

<210> SEQ ID NO 88
<211> LENGTH: 76
<212> TYPE: DNA
<213> ORGANISM: Artificial Sequence
<220> FEATURE:
<223> OTHER INFORMATION: Oligonucleotide 2521-95

<400> SEQUENCE: 88
tcgaccccac cgcctccacc cagaccgtga caaaccatct gacgagtcag caggtcgtat    60
ttacagtcgt ggaaca                                             76

<210> SEQ ID NO 89
<211> LENGTH: 74
<212> TYPE: DNA
<213> ORGANISM: Artificial Sequence
<220> FEATURE:
<223> OTHER INFORMATION: Oligonucleotide 2521-96

```
<400> SEQUENCE: 89
tatgcgtaac cactgtttct gggaccacct gctgaaacag acatctgtc cgtctccggg    60 tggaggcggt gggg                                                     74

<210> SEQ ID NO 90
<211> LENGTH: 76
<212> TYPE: DNA
<213> ORGANISM: Artificial Sequence
<220> FEATURE:
<223> OTHER INFORMATION: Oligonucleotide 2521-97

<400> SEQUENCE: 90
tcgaccccac cgcctccacc cggagacgga cagatgtcct gtttcagcag gtggtcccag    60
aaacagtggt tacgca                                                   76

<210> SEQ ID NO 91
<211> LENGTH: 74
<212> TYPE: DNA
<213> ORGANISM: Artificial Sequence
<220> FEATURE:
<223> OTHER INFORMATION: Oligonucleotide 2521-98

<400> SEQUENCE: 91
tatggctaac cagtgttggt gggactctct gctgaaaaaa aacgtttgtg aattcttcgg    60
tggaggcggt gggg                                                     74

<210> SEQ ID NO 92
<211> LENGTH: 76
<212> TYPE: DNA
<213> ORGANISM: Artificial Sequence
<220> FEATURE:
<223> OTHER INFORMATION: Oligonucleotide 2521-99

<400> SEQUENCE: 92
tcgaccccac cgcctccacc gaagaattca caaacgtttt ttttcagcag agagtcccac    60
caacactggt tagcca                                                   76

<210> SEQ ID NO 93
<211> LENGTH: 74
<212> TYPE: DNA
<213> ORGANISM: Artificial Sequence
<220> FEATURE:
<223> OTHER INFORMATION: Oligonucleotide 2551-48

<400> SEQUENCE: 93
tatgttccac gactgcaaat gggacctgct gaccaaacag tgggtttgcc acggtctggg    60
tggaggcggt gggg                                                     74

<210> SEQ ID NO 94
<211> LENGTH: 76
<212> TYPE: DNA
<213> ORGANISM: Artificial Sequence
<220> FEATURE:
<223> OTHER INFORMATION: Oligonucleotide 2551-49

<400> SEQUENCE: 94
tcgaccccac cgcctccacc cagaccgtgg caaacccact gtttggtcag caggtcccat    60
ttgcagtcgt ggaaca                                                   76

<210> SEQ ID NO 95
<211> LENGTH: 141
<212> TYPE: DNA
```

-continued

<213> ORGANISM: Artificial Sequence
<220> FEATURE:
<223> OTHER INFORMATION: pCFM1656 vector fragment containing PL promoter

<400> SEQUENCE: 95

```
ctaattccgc tctcacctac caaacaatgc ccccctgcaa aaaataaatt catataaaaa      60
acatacagat aaccatctgc ggtgataaat tatctctggc ggtgttgaca taaataccac     120
tggcggtgat actgagcaca t                                               141
```

<210> SEQ ID NO 96
<211> LENGTH: 55
<212> TYPE: DNA
<213> ORGANISM: Artificial Sequence
<220> FEATURE:
<223> OTHER INFORMATION: pCFM1656 vector fragment

<400> SEQUENCE: 96

```
cgatttgatt ctagaaggag gaataacata tggttaacgc gttggaattc ggtac           55
```

<210> SEQ ID NO 97
<211> LENGTH: 1546
<212> TYPE: DNA
<213> ORGANISM: Artificial Sequence
<220> FEATURE:
<223> OTHER INFORMATION: pAMG21 vector fragment

<400> SEQUENCE: 97

```
gcgtaacgta tgcatggtct ccccatgcga gagtagggaa ctgccaggca tcaaataaaa      60
cgaaaggctc agtcgaaaga ctgggccttt cgttttatct gttgtttgtc ggtgaacgct    120
ctcctgagta ggacaaatcc gccgggagcg gatttgaacg ttgcgaagca acggcccgga    180
gggtggcggg caggacgccc gccataaact gccaggcatc aaattaagca gaaggccatc    240
ctgacggatg gcctttttgc gtttctacaa actcttttgt ttattttcct aaatacattc    300
aaatatggac gtcgtactta actttttaaag tatgggcaat caattgctcc tgttaaaatt    360
gctttagaaa tactttggca gcggtttgtt gtattgagtt tcatttgcgc attggttaaa    420
tggaaagtga ccgtgcgctt actacagcct aatattttg aaatatccca agagcttttt    480
ccttcgcatg cccacgctaa acattctttt tctcttttgg ttaaatcgtt gtttgattta    540
ttatttgcta tatttatttt tcgataatta tcaactagaa aaggaacaat taatggtatg    600
ttcatacacg catgtaaaaa taaactatct atatagttgt ctttctctga atgtgcaaaa    660
ctaagcattc cgaagccatt attagcagta tgaataggga aactaaaccc agtgataaga    720
cctgatgatt tcgcttcttt aattacattt ggagattttt tatttacagc attgttttca    780
aatatattcc aattaatcgg tgaatgattg gagttagaat aatctactat aggatcatat    840
tttattaaat tagcgtcatc ataatattgc ctccattttt tagggtaatt atccagaatt    900
gaaatatcag atttaaccat agaatgagga taaatgatcg cgagtaaata atattcacaa    960
tgtaccattt tagtcatatc agataagcat tgattaatat cattattgct tctacaggct   1020
ttaattttat taattattct gtaagtgtcg tcggcattta tgtctttcat acccatctct   1080
ttatccttac ctattgtttg tcgcaagttt tgcgtgttat atcattaa aacggtaata   1140 gattgacatt tgattctaat aaattggatt tttgtcacac tattatatcg cttgaaatac   1200
aattgtttaa cataagtacc tgtaggatcg tacaggttta cgcaagaaaa tggtttgtta   1260
tagtcgatta atcgatttga ttctagattt gttttaacta attaaaggag gaataacata   1320
tggttaacgc gttggaattc gagctcacta gtgtcgacct gcagggtacc atggaagctt   1380
```

```
actcgaggat ccgcggaaag aagaagaaga agaagaaagc ccgaaaggaa gctgagttgg    1440
ctgctgccac cgctgagcaa taactagcat aaccccttgg ggcctctaaa cgggtcttga    1500
ggggtttttt gctgaaagga ggaaccgctc ttcacgctct tcacgc                  1546
```

<210> SEQ ID NO 98
<211> LENGTH: 872
<212> TYPE: DNA
<213> ORGANISM: Artificial Sequence
<220> FEATURE:
<223> OTHER INFORMATION: GM221 insert
<220> FEATURE:
<221> NAME/KEY: misc_feature
<222> LOCATION: (1)..(10)
<223> OTHER INFORMATION: Flanking ebg sequence
<220> FEATURE:
<221> NAME/KEY: misc_feature
<222> LOCATION: (863)..(872)
<223> OTHER INFORMATION: Flanking ebg sequence

<400> SEQUENCE: 98

```
ttattttcgt gcggccgcac cattatcacc gccagaggta aactagtcaa cacgcacggt     60
gttagatatt tatcccttgc ggtgatagat tgagcacatc gatttgattc tagaaggagg    120
gataatatat gagcacaaaa aagaaaccat taacacaaga gcagcttgag gacgcacgtc    180
gccttaaagc aatttatgaa aaaaagaaaa atgaacttgg cttatcccag gaatctgtcg    240
cagacaagat ggggatgggg cagtcaggcg ttggtgcttt atttaatggc atcaatgcat    300
taaatgctta taacgccgca ttgcttacaa aaattctcaa agttagcgtt gaagaattta    360
gcccttcaat cgccagagaa tctacgagat gtatgaagcg gttagtatgc agccgtcact    420
tagaagtgag tatgagtacc ctgttttttc tcatgttcag gcaggatgt tctcacctaa     480 gcttagaacc tttaccaaag gtgatgcgga gagatgggta agcacaacca aaaaagccag    540
tgattctgca ttctggcttg aggttgaagg taattccatg accgcaccaa caggctccaa    600
gccaagcttt cctgacggaa tgttaattct cgttgaccct gagcaggctg ttgagccagg    660
tgatttctgc atagccagac ttggggggtga tgagtttacc ttcaagaaac tgatcaggga    720
tagcggtcag gtgttttta caaccactaaa cccacagtac ccaatgatcc catcgaatga    780
gagttgttcc gttgtgggga aagttatcgc tagtcagtgg cctgaagaga cgtttggctg    840
atagactagt ggatccacta gtgtttctgc cc                                 872
```

<210> SEQ ID NO 99
<211> LENGTH: 1197
<212> TYPE: DNA
<213> ORGANISM: Artificial Sequence
<220> FEATURE:
<223> OTHER INFORMATION: GM221 insert
<220> FEATURE:
<221> NAME/KEY: misc_feature
<222> LOCATION: (1)..(10)
<223> OTHER INFORMATION: Flanking ebg sequence
<220> FEATURE:
<221> NAME/KEY: misc_feature
<222> LOCATION: (1188)..(1197)
<223> OTHER INFORMATION: Flanking ebg sequence

<400> SEQUENCE: 99

```
ggcggaaacc gacgtccatc gaatggtgca aaacctttcg cggtatggca tgatagcgcc     60
cggaagagag tcaattcagg gtggtgaatg tgaaaccagt aacgttatac gatgtcgcag    120
agtatgccgg tgtctcttat cagaccgttt cccgcgtggt gaaccaggcc agccacgttt    180
ctgcgaaaac gcgggaaaaa gtcgaagcgg cgatggcgga gctgaattac attcccaacc    240
```

```
gcgtggcaca acaactggcg ggcaaacagt cgctcctgat tggcgttgcc acctccagtc    300
tggccctgca cgcgccgtcg caaattgtcg cggcgattaa atctcgcgcc gatcaactgg    360
gtgccagcgt ggtggtgtcg atggtagaac gaagcggcgt cgaagcctgt aaagcggcgg    420
tgcacaatct tctcgcgcaa cgcgtcagtg ggctgatcat taactatccg ctggatgacc    480
aggatgccat tgctgtggaa gctgcctgca ctaatgttcc ggcgttattt cttgatgtct    540
ctgaccagac acccatcaac agtattattt tctcccatga agacggtacg cgactgggcg    600
tggagcatct ggtcgcattg ggtcaccagc aaatcgcgct gttagcgggc ccattaagtt    660
ctgtctcggc gcgtctgcgt ctggctggct ggcataaata tctcactcgc aatcaaattc    720
agccgatagc ggaacgggaa ggcgactgga gtgccatgtc cggttttcaa caaaccatgc    780
aaatgctgaa tgagggcatc gttcccactg cgatgctggt tgccaacgat cagatggcgc    840
tgggcgcaat gcgcgccatt accgagtccg ggctgcgcgt tggtgcggat atctcggtag    900
tgggatacga cgataccgaa gacagctcat gttatatccc gccgttaacc accatcaaac    960
aggattttcg cctgctgggg caaaccagcg tggaccgctt gctgcaactc tctcagggcc   1020
aggcggtgaa gggcaatcag ctgttgcccg tctcactggt gaaaagaaaa accaccctgg   1080
cgcccaatac gcaaaccgcc tctccccgcg cgttggccga ttcattaatg cagctggcac   1140
gacaggtttc ccgactggaa agcggacagt aaggtaccat aggatccagg cacagga      1197
```

<210> SEQ ID NO 100
<211> LENGTH: 14
<212> TYPE: PRT
<213> ORGANISM: Artificial Sequence
<220> FEATURE:
<223> OTHER INFORMATION: Modulator of TALL-1
<220> FEATURE:
<221> NAME/KEY: MISC_FEATURE
<222> LOCATION: (1)..(1)
<223> OTHER INFORMATION: Absent or amino acid residue
<220> FEATURE:
<221> NAME/KEY: MISC_FEATURE
<222> LOCATION: (2)..(2)
<223> OTHER INFORMATION: Absent or amino acid residue
<220> FEATURE:
<221> NAME/KEY: MISC_FEATURE
<222> LOCATION: (3)..(3)
<223> OTHER INFORMATION: Absent or amino acid residue
<220> FEATURE:
<221> NAME/KEY: MISC_FEATURE
<222> LOCATION: (6)..(6)
<223> OTHER INFORMATION: Amino acid residue
<220> FEATURE:
<221> NAME/KEY: MISC_FEATURE
<222> LOCATION: (8)..(8)
<223> OTHER INFORMATION: Thr or Ile
<220> FEATURE:
<221> NAME/KEY: MISC_FEATURE
<222> LOCATION: (9)..(9)
<223> OTHER INFORMATION: Basic or hydrophobic residue
<220> FEATURE:
<221> NAME/KEY: MISC_FEATURE
<222> LOCATION: (10)..(10)
<223> OTHER INFORMATION: Amino acid residue
<220> FEATURE:
<221> NAME/KEY: MISC_FEATURE
<222> LOCATION: (12)..(12)
<223> OTHER INFORMATION: Neutral hydrophobic residue
<220> FEATURE:
<221> NAME/KEY: MISC_FEATURE
<222> LOCATION: (13)..(13)
<223> OTHER INFORMATION: Absent or amino acid residue
<220> FEATURE:
<221> NAME/KEY: MISC_FEATURE
<222> LOCATION: (14)..(14)
<223> OTHER INFORMATION: Absent or amino acid residue -continued

```
<400> SEQUENCE: 100

Xaa Xaa Xaa Cys Asp Xaa Leu Xaa Xaa Cys Xaa Xaa Xaa
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Modulator of TALL-1
<220> FEATURE:
<221> NAME/KEY: MISC_FEATURE
<222> LOCATION: (1)..(1)
<223> OTHER INFORMATION: Absent or amino acid residue
<220> FEATURE:
<221> NAME/KEY: MISC_FEATURE
<222> LOCATION: (2)..(2)
<223> OTHER INFORMATION: Absent or amino acid residue
<220> FEATURE:
<221> NAME/KEY: MISC_FEATURE
<222> LOCATION: (3)..(3)
<223> OTHER INFORMATION: Absent or amino acid residue
<220> FEATURE:
<221> NAME/KEY: MISC_FEATURE
<222> LOCATION: (5)..(5)
<223> OTHER INFORMATION: Neutral hydrophobic residue
<220> FEATURE:
<221> NAME/KEY: MISC_FEATURE
<222> LOCATION: (8)..(8)
<223> OTHER INFORMATION: Neutral hydrophobic residue
<220> FEATURE:
<221> NAME/KEY: misc_feature
<222> LOCATION: (10)..(10)
<223> OTHER INFORMATION: Acidic residue
<220> FEATURE:
<221> NAME/KEY: MISC_FEATURE
<222> LOCATION: (12)..(12)
<223> OTHER INFORMATION: Amino acid residue
<220> FEATURE:
<221> NAME/KEY: MISC_FEATURE
<222> LOCATION: (13)..(13)
<223> OTHER INFORMATION: Amino acid residue
<220> FEATURE:
<221> NAME/KEY: MISC_FEATURE
<222> LOCATION: (14)..(14)
<223> OTHER INFORMATION: Absent or amino acid residue

<400> SEQUENCE: 101

Xaa Xaa Xaa Cys Xaa Pro Phe Xaa Trp Xaa Cys Xaa Xaa Xaa
1               5                   10

<210> SEQ ID NO 102
<211> LENGTH: 14
<212> TYPE: PRT
<213> ORGANISM: Artificial Sequence
<220> FEATURE:
<223> OTHER INFORMATION: Modulator of TALL-1
<220> FEATURE:
<221> NAME/KEY: MISC_FEATURE
<222> LOCATION: (1)..(1)
<223> OTHER INFORMATION: Absent or amino acid residue
<220> FEATURE:
<221> NAME/KEY: MISC_FEATURE
<222> LOCATION: (2)..(2)
<223> OTHER INFORMATION: Absent or amino acid residue
<220> FEATURE:
<221> NAME/KEY: MISC_FEATURE
<222> LOCATION: (3)..(3)
<223> OTHER INFORMATION: Absent or amino acid residue
<220> FEATURE:
<221> NAME/KEY: MISC_FEATURE
<222> LOCATION: (6)..(6)
<223> OTHER INFORMATION: Hydrophobic residue
<220> FEATURE:
<221> NAME/KEY: MISC_FEATURE
<222> LOCATION: (7)..(7)
```

-continued

```
<223> OTHER INFORMATION: Hydrophobic residue
<220> FEATURE:
<221> NAME/KEY: MISC_FEATURE
<222> LOCATION: (10)..(10)
<223> OTHER INFORMATION: Acidic or polar hydrophobic residue
<220> FEATURE:
<221> NAME/KEY: MISC_FEATURE
<222> LOCATION: (12)..(12)
<223> OTHER INFORMATION: Absent or amino acid residue
<220> FEATURE:
<221> NAME/KEY: MISC_FEATURE
<222> LOCATION: (13)..(13)
<223> OTHER INFORMATION: Absent or amino acid residue
<220> FEATURE:
<221> NAME/KEY: MISC_FEATURE
<222> LOCATION: (14)..(14)
<223> OTHER INFORMATION: Absent or amino acid residue

<400> SEQUENCE: 102

Xaa Xaa Xaa Cys Trp Xaa Xaa Trp Gly Xaa Cys Xaa Xaa Xaa
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Modulator of TALL-1
<220> FEATURE:
<221> NAME/KEY: MISC_FEATURE
<222> LOCATION: (1)..(1)
<223> OTHER INFORMATION: Absent or amino acid residue
<220> FEATURE:
<221> NAME/KEY: MISC_FEATURE
<222> LOCATION: (2)..(2)
<223> OTHER INFORMATION: Neutral hydrophobic residue
<220> FEATURE:
<221> NAME/KEY: MISC_FEATURE
<222> LOCATION: (3)..(3)
<223> OTHER INFORMATION: Amino acid residue
<220> FEATURE:
<221> NAME/KEY: MISC_FEATURE
<222> LOCATION: (5)..(5)
<223> OTHER INFORMATION: Amino acid residue
<220> FEATURE:
<221> NAME/KEY: MISC_FEATURE
<222> LOCATION: (6)..(6)
<223> OTHER INFORMATION: Amino acid residue
<220> FEATURE:
<221> NAME/KEY: MISC_FEATURE
<222> LOCATION: (7)..(7)
<223> OTHER INFORMATION: Amino acid residue
<220> FEATURE:
<221> NAME/KEY: MISC_FEATURE
<222> LOCATION: (8)..(8)
<223> OTHER INFORMATION: Amino acid residue
<220> FEATURE:
<221> NAME/KEY: MISC_FEATURE
<222> LOCATION: (9)..(9)
<223> OTHER INFORMATION: Acidic residue
<220> FEATURE:
<221> NAME/KEY: MISC_FEATURE
<222> LOCATION: (10)..(10)
<223> OTHER INFORMATION: Amino acid residue
<220> FEATURE:
<221> NAME/KEY: MISC_FEATURE
<222> LOCATION: (12)..(12)
<223> OTHER INFORMATION: Amino acid residue
<220> FEATURE:
<221> NAME/KEY: MISC_FEATURE
<222> LOCATION: (13)..(13)
<223> OTHER INFORMATION: Amino acid residue
<220> FEATURE:
<221> NAME/KEY: MISC_FEATURE
<222> LOCATION: (14)..(14)
<223> OTHER INFORMATION: Neutral hydrophobic residue

<400> SEQUENCE: 103
```

```
Xaa Xaa Xaa Cys Xaa Xaa Xaa Xaa Xaa Xaa Cys Xaa Xaa Xaa
1               5                   10
```

<210> SEQ ID NO 104
<211> LENGTH: 18
<212> TYPE: PRT
<213> ORGANISM: Artificial Sequence
<220> FEATURE:
<223> OTHER INFORMATION: Modulator of TALL-1
<220> FEATURE:
<221> NAME/KEY: MISC_FEATURE
<222> LOCATION: (1)..(1)
<223> OTHER INFORMATION: Absent or amino acid residue
<220> FEATURE:
<221> NAME/KEY: MISC_FEATURE
<222> LOCATION: (2)..(2)
<223> OTHER INFORMATION: Absent or amino acid residue
<220> FEATURE:
<221> NAME/KEY: MISC_FEATURE
<222> LOCATION: (3)..(3)
<223> OTHER INFORMATION: Acidic or amide residue
<220> FEATURE:
<221> NAME/KEY: MISC_FEATURE
<222> LOCATION: (5)..(5)
<223> OTHER INFORMATION: Amino acid residue
<220> FEATURE:
<221> NAME/KEY: MISC_FEATURE
<222> LOCATION: (6)..(6)
<223> OTHER INFORMATION: Aromatic residue
<220> FEATURE:
<221> NAME/KEY: MISC_FEATURE
<222> LOCATION: (8)..(8)
<223> OTHER INFORMATION: Amino acid residue
<220> FEATURE:
<221> NAME/KEY: MISC_FEATURE
<222> LOCATION: (10)..(10)
<223> OTHER INFORMATION: Thr or Ile
<220> FEATURE:
<221> NAME/KEY: MISC_FEATURE
<222> LOCATION: (11)..(11)
<223> OTHER INFORMATION: Basic residue
<220> FEATURE:
<221> NAME/KEY: MISC_FEATURE
<222> LOCATION: (12)..(12)
<223> OTHER INFORMATION: Amino acid residue
<220> FEATURE:
<221> NAME/KEY: MISC_FEATURE
<222> LOCATION: (13)..(13)
<223> OTHER INFORMATION: Amino acid residue
<220> FEATURE:
<221> NAME/KEY: MISC_FEATURE
<222> LOCATION: (14)..(14)
<223> OTHER INFORMATION: Neutral hydrophobic residue
<220> FEATURE:
<221> NAME/KEY: MISC_FEATURE
<222> LOCATION: (16)..(16)
<223> OTHER INFORMATION: Absent or amino acid residue
<220> FEATURE:
<221> NAME/KEY: MISC_FEATURE
<222> LOCATION: (17)..(17)
<223> OTHER INFORMATION: Absent or amino acid residue
<220> FEATURE:
<221> NAME/KEY: MISC_FEATURE
<222> LOCATION: (18)..(18)
<223> OTHER INFORMATION: Absent or amino acid residue

<400> SEQUENCE: 104

```
Xaa Xaa Xaa Cys Xaa Xaa Asp Xaa Leu Xaa Xaa Xaa Xaa Xaa Cys Xaa
1               5                   10                  15

Xaa Xaa
```

<210> SEQ ID NO 105
<211> LENGTH: 18
<212> TYPE: PRT
<213> ORGANISM: Artificial Sequence

```
<220> FEATURE:
<223> OTHER INFORMATION: Modulator of TALL-1
<220> FEATURE:
<221> NAME/KEY: MISC_FEATURE
<222> LOCATION: (1)..(1)
<223> OTHER INFORMATION: Absent or amino acid residue
<220> FEATURE:
<221> NAME/KEY: MISC_FEATURE
<222> LOCATION: (2)..(2)
<223> OTHER INFORMATION: Absent or amino acid residue
<220> FEATURE:
<221> NAME/KEY: MISC_FEATURE
<222> LOCATION: (3)..(3)
<223> OTHER INFORMATION: Absent or amino acid residue
<220> FEATURE:
<221> NAME/KEY: MISC_FEATURE
<222> LOCATION: (5)..(5)
<223> OTHER INFORMATION: Amino acid residue
<220> FEATURE:
<221> NAME/KEY: MISC_FEATURE
<222> LOCATION: (7)..(7)
<223> OTHER INFORMATION: Amino acid residue
<220> FEATURE:
<221> NAME/KEY: MISC_FEATURE
<222> LOCATION: (9)..(9)
<223> OTHER INFORMATION: Thr or Ile
<220> FEATURE:
<221> NAME/KEY: MISC_FEATURE
<222> LOCATION: (10)..(10)
<223> OTHER INFORMATION: Basic residue
<220> FEATURE:
<221> NAME/KEY: MISC_FEATURE
<222> LOCATION: (11)..(11)
<223> OTHER INFORMATION: Amino acid residue
<220> FEATURE:
<221> NAME/KEY: MISC_FEATURE
<222> LOCATION: (12)..(12)
<223> OTHER INFORMATION: Amino acid residue
<220> FEATURE:
<221> NAME/KEY: MISC_FEATURE
<222> LOCATION: (13)..(13)
<223> OTHER INFORMATION: Neutral hydrophobic residue
<220> FEATURE:
<221> NAME/KEY: MISC_FEATURE
<222> LOCATION: (14)..(14)
<223> OTHER INFORMATION: Amino acid residue
<220> FEATURE:
<221> NAME/KEY: MISC_FEATURE
<222> LOCATION: (16)..(16)
<223> OTHER INFORMATION: Amino acid residue
<220> FEATURE:
<221> NAME/KEY: MISC_FEATURE
<222> LOCATION: (17)..(17)
<223> OTHER INFORMATION: Neutral hydrophobic residue
<220> FEATURE:
<221> NAME/KEY: MISC_FEATURE
<222> LOCATION: (18)..(18)
<223> OTHER INFORMATION: Absent or amino acid residue

<400> SEQUENCE: 105

Xaa Xaa Xaa Cys Xaa Asp Xaa Leu Xaa Xaa Xaa Xaa Xaa Xaa Cys Xaa
1               5                   10                  15

Xaa Xaa

<210> SEQ ID NO 106
<211> LENGTH: 18
<212> TYPE: PRT
<213> ORGANISM: Artificial Sequence
<220> FEATURE:
<223> OTHER INFORMATION: Modulator of TALL-1
<220> FEATURE:
<221> NAME/KEY: MISC_FEATURE
<222> LOCATION: (1)..(1)
<223> OTHER INFORMATION: Absent or amino acid residue
<220> FEATURE:
<221> NAME/KEY: MISC_FEATURE
<222> LOCATION: (2)..(2)
```

-continued

```
<223> OTHER INFORMATION: Absent or amino acid residue
<220> FEATURE:
<221> NAME/KEY: MISC_FEATURE
<222> LOCATION: (3)..(3)
<223> OTHER INFORMATION: Absent or amino acid residue
<220> FEATURE:
<221> NAME/KEY: MISC_FEATURE
<222> LOCATION: (5)..(5)
<223> OTHER INFORMATION: Amino acid residue
<220> FEATURE:
<221> NAME/KEY: MISC_FEATURE
<222> LOCATION: (6)..(6)
<223> OTHER INFORMATION: Amino acid residue
<220> FEATURE:
<221> NAME/KEY: MISC_FEATURE
<222> LOCATION: (7)..(7)
<223> OTHER INFORMATION: Amino acid residue
<220> FEATURE:
<221> NAME/KEY: MISC_FEATURE
<222> LOCATION: (10)..(10)
<223> OTHER INFORMATION: Amino acid residue
<220> FEATURE:
<221> NAME/KEY: MISC_FEATURE
<222> LOCATION: (12)..(12)
<223> OTHER INFORMATION: Thr or Ile
<220> FEATURE:
<221> NAME/KEY: MISC_FEATURE
<222> LOCATION: (13)..(13)
<223> OTHER INFORMATION: Amino acid residue
<220> FEATURE:
<221> NAME/KEY: MISC_FEATURE
<222> LOCATION: (14)..(14)
<223> OTHER INFORMATION: Amino acid residue
<220> FEATURE:
<221> NAME/KEY: MISC_FEATURE
<222> LOCATION: (16)..(16)
<223> OTHER INFORMATION: Absent or amino acid residue
<220> FEATURE:
<221> NAME/KEY: MISC_FEATURE
<222> LOCATION: (17)..(17)
<223> OTHER INFORMATION: Absent or amino acid residue
<220> FEATURE:
<221> NAME/KEY: MISC_FEATURE
<222> LOCATION: (18)..(18)
<223> OTHER INFORMATION: Absent or amino acid residue

<400> SEQUENCE: 106

Xaa Xaa Xaa Cys Xaa Xaa Xaa Trp Asp Xaa Leu Xaa Xaa Xaa Cys Xaa
1               5                   10                  15

Xaa Xaa

<210> SEQ ID NO 107
<211> LENGTH: 18
<212> TYPE: PRT
<213> ORGANISM: Artificial Sequence
<220> FEATURE:
<223> OTHER INFORMATION: Modulator of TALL-1
<220> FEATURE:
<221> NAME/KEY: MISC_FEATURE
<222> LOCATION: (1)..(1)
<223> OTHER INFORMATION: Absent or amino acid residue
<220> FEATURE:
<221> NAME/KEY: MISC_FEATURE
<222> LOCATION: (2)..(2)
<223> OTHER INFORMATION: Absent or amino acid residue
<220> FEATURE:
<221> NAME/KEY: MISC_FEATURE
<222> LOCATION: (3)..(3)
<223> OTHER INFORMATION: Absent or amino acid residue
<220> FEATURE:
<221> NAME/KEY: MISC_FEATURE
<222> LOCATION: (5)..(5)
<223> OTHER INFORMATION: Amino acid residue
<220> FEATURE:
<221> NAME/KEY: MISC_FEATURE
<222> LOCATION: (6)..(6)
<223> OTHER INFORMATION: Amino acid residue
```

```
<220> FEATURE:
<221> NAME/KEY: MISC_FEATURE
<222> LOCATION: (7)..(7)
<223> OTHER INFORMATION: Amino acid residue
<220> FEATURE:
<221> NAME/KEY: MISC_FEATURE
<222> LOCATION: (9)..(9)
<223> OTHER INFORMATION: Amino acid residue
<220> FEATURE:
<221> NAME/KEY: MISC_FEATURE
<222> LOCATION: (11)..(11)
<223> OTHER INFORMATION: Thr or Ile
<220> FEATURE:
<221> NAME/KEY: MISC_FEATURE
<222> LOCATION: (11)..(11)
<223> OTHER INFORMATION: Thr or Ile
<220> FEATURE:
<221> NAME/KEY: MISC_FEATURE
<222> LOCATION: (13)..(13)
<223> OTHER INFORMATION: Amino acid residue
<220> FEATURE:
<221> NAME/KEY: MISC_FEATURE
<222> LOCATION: (15)..(15)
<223> OTHER INFORMATION: Absent or amino acid residue
<220> FEATURE:
<221> NAME/KEY: MISC_FEATURE
<222> LOCATION: (16)..(16)
<223> OTHER INFORMATION: Absent or amino acid residue
<220> FEATURE:
<221> NAME/KEY: MISC_FEATURE
<222> LOCATION: (17)..(17)
<223> OTHER INFORMATION: Absent or amino acid residue
<220> FEATURE:
<221> NAME/KEY: MISC_FEATURE
<222> LOCATION: (18)..(18)
<223> OTHER INFORMATION: Absent or amino acid residue

<400> SEQUENCE: 107

Xaa Xaa Xaa Cys Xaa Xaa Xaa Asp Xaa Leu Xaa Lys Xaa Cys Xaa Xaa
1               5                   10                  15

Xaa Xaa

<210> SEQ ID NO 108
<211> LENGTH: 4
<212> TYPE: PRT
<213> ORGANISM: Artificial Sequence
<220> FEATURE:
<223> OTHER INFORMATION: Modulator of TALL-1
<220> FEATURE:
<221> NAME/KEY: MISC_FEATURE
<222> LOCATION: (2)..(2)
<223> OTHER INFORMATION: Amino acid residue
<220> FEATURE:
<221> NAME/KEY: MISC_FEATURE
<222> LOCATION: (4)..(4)
<223> OTHER INFORMATION: Thr or Ile

<400> SEQUENCE: 108

Asp Xaa Leu Xaa
1

<210> SEQ ID NO 109
<211> LENGTH: 14
<212> TYPE: PRT
<213> ORGANISM: Artificial Sequence
<220> FEATURE:
<223> OTHER INFORMATION: Modulator of TALL-1
<220> FEATURE:
<221> NAME/KEY: MISC_FEATURE
<222> LOCATION: (1)..(1)
<223> OTHER INFORMATION: Absent or amino acid residue (one of residues
      1, 2, or 3 preferably Cys when one of residues 12, 13, or 14 is
      Cys, and only one of residues 1, 2, or 3 may be Cys)
<220> FEATURE:
<221> NAME/KEY: MISC_FEATURE
```

```
<222> LOCATION: (2)..(2)
<223> OTHER INFORMATION: Absent or amino acid residue (one of residues
      1, 2, or 3 preferably Cys when one of residues 12, 13, or 14 is
      Cys, and only one of residues 1, 2, or 3 may be Cys)
<220> FEATURE:
<221> NAME/KEY: MISC_FEATURE
<222> LOCATION: (3)..(3)
<223> OTHER INFORMATION: Absent or amino acid residue (one of residues
      1, 2, or 3 preferably Cys when one of residues 12, 13, or 14 is
      Cys, and only one of residues 1, 2, or 3 may be Cys)
<220> FEATURE:
<221> NAME/KEY: MISC_FEATURE
<222> LOCATION: (5)..(5)
<223> OTHER INFORMATION: Trp, Tyr, or Phe (Trp preferred)
<220> FEATURE:
<221> NAME/KEY: MISC_FEATURE
<222> LOCATION: (7)..(7)
<223> OTHER INFORMATION: Amino acid residue (Leu preferred)
<220> FEATURE:
<221> NAME/KEY: MISC_FEATURE
<222> LOCATION: (9)..(9)
<223> OTHER INFORMATION: Thr or Ile (Thr preferred)
<220> FEATURE:
<221> NAME/KEY: MISC_FEATURE
<222> LOCATION: (10)..(10)
<223> OTHER INFORMATION: Lys, Arg, or His (Lys preferred)
<220> FEATURE:
<221> NAME/KEY: MISC_FEATURE
<222> LOCATION: (12)..(12)
<223> OTHER INFORMATION: Cys, neutral hydrophobic residue, or basic
      residue (Trp, Cys, or Arg preferred, and only one of residues 12,
      13, or 14 may be Cys)
<220> FEATURE:
<221> NAME/KEY: MISC_FEATURE
<222> LOCATION: (13)..(13)
<223> OTHER INFORMATION: Cys, neutral hydrophobic residue, or absent
      (Val preferred, and only one of residues 12, 13, or 14 may be Cys)
<220> FEATURE:
<221> NAME/KEY: MISC_FEATURE
<222> LOCATION: (14)..(14)
<223> OTHER INFORMATION: Absent or amino acid residue (only one of
      residues 12, 13, or 14 may be Cys)

<400> SEQUENCE: 109

Xaa Xaa Xaa Lys Xaa Asp Xaa Leu Xaa Xaa Gln Xaa Xaa Xaa
1               5                   10

<210> SEQ ID NO 110
<211> LENGTH: 5
<212> TYPE: PRT
<213> ORGANISM: Artificial Sequence
<220> FEATURE:
<223> OTHER INFORMATION: Modulator of TALL-1

<400> SEQUENCE: 110

Pro Phe Pro Trp Glu
1               5

<210> SEQ ID NO 111
<211> LENGTH: 248
<212> TYPE: PRT
<213> ORGANISM: Artificial Sequence
<220> FEATURE:
<223> OTHER INFORMATION: TALL-1 inhibitory peptibody TALL-1-8-1-a

<400> SEQUENCE: 111

Met Pro Gly Thr Cys Phe Pro Phe Pro Trp Glu Cys Thr His Ala Gly
1               5                   10                  15

Gly Gly Gly Gly Val Asp Lys Thr His Thr Cys Pro Pro Cys Pro Ala
                20                  25                  30

Pro Glu Leu Leu Gly Gly Pro Ser Val Phe Leu Phe Pro Pro Lys Pro
            35                  40                  45
```

```
Lys Asp Thr Leu Met Ile Ser Arg Thr Pro Glu Val Thr Cys Val Val
 50                  55                  60

Val Asp Val Ser His Glu Asp Pro Glu Val Lys Phe Asn Trp Tyr Val
 65                  70                  75                  80

Asp Gly Val Glu Val His Asn Ala Lys Thr Lys Pro Arg Glu Glu Gln
                 85                  90                  95

Tyr Asn Ser Thr Tyr Arg Val Val Ser Val Leu Thr Val Leu His Gln
            100                 105                 110

Asp Trp Leu Asn Gly Lys Glu Tyr Lys Cys Lys Val Ser Asn Lys Ala
        115                 120                 125

Leu Pro Ala Pro Ile Glu Lys Thr Ile Ser Lys Ala Lys Gly Gln Pro
    130                 135                 140

Arg Glu Pro Gln Val Tyr Thr Leu Pro Pro Ser Arg Asp Glu Leu Thr
145                 150                 155                 160

Lys Asn Gln Val Ser Leu Thr Cys Leu Val Lys Gly Phe Tyr Pro Ser
                165                 170                 175

Asp Ile Ala Val Glu Trp Glu Ser Asn Gly Gln Pro Glu Asn Asn Tyr
            180                 185                 190

Lys Thr Thr Pro Pro Val Leu Asp Ser Asp Gly Ser Phe Phe Leu Tyr
        195                 200                 205

Ser Lys Leu Thr Val Asp Lys Ser Arg Trp Gln Gln Gly Asn Val Phe
    210                 215                 220

Ser Cys Ser Val Met His Glu Ala Leu His Asn His Tyr Thr Gln Lys
225                 230                 235                 240

Ser Leu Ser Leu Ser Pro Gly Lys
                245

<210> SEQ ID NO 112
<211> LENGTH: 248
<212> TYPE: PRT
<213> ORGANISM: Artificial Sequence
<220> FEATURE:
<223> OTHER INFORMATION: TALL-1 inhibitory peptibody TALL-1-8-2-a

<400> SEQUENCE: 112

Met Trp Gly Ala Cys Trp Pro Phe Pro Trp Glu Cys Phe Lys Glu Gly
 1               5                  10                  15

Gly Gly Gly Gly Val Asp Lys Thr His Thr Cys Pro Pro Cys Pro Ala
                20                  25                  30

Pro Glu Leu Leu Gly Gly Pro Ser Val Phe Leu Phe Pro Pro Lys Pro
            35                  40                  45

Lys Asp Thr Leu Met Ile Ser Arg Thr Pro Glu Val Thr Cys Val Val
 50                  55                  60

Val Asp Val Ser His Glu Asp Pro Glu Val Lys Phe Asn Trp Tyr Val
 65                  70                  75                  80

Asp Gly Val Glu Val His Asn Ala Lys Thr Lys Pro Arg Glu Glu Gln
                 85                  90                  95

Tyr Asn Ser Thr Tyr Arg Val Val Ser Val Leu Thr Val Leu His Gln
            100                 105                 110

Asp Trp Leu Asn Gly Lys Glu Tyr Lys Cys Lys Val Ser Asn Lys Ala
        115                 120                 125

Leu Pro Ala Pro Ile Glu Lys Thr Ile Ser Lys Ala Lys Gly Gln Pro
    130                 135                 140

Arg Glu Pro Gln Val Tyr Thr Leu Pro Pro Ser Arg Asp Glu Leu Thr
145                 150                 155                 160

Lys Asn Gln Val Ser Leu Thr Cys Leu Val Lys Gly Phe Tyr Pro Ser
```

```
                165                 170                 175
Asp Ile Ala Val Glu Trp Glu Ser Asn Gly Gln Pro Glu Asn Asn Tyr
            180                 185                 190

Lys Thr Thr Pro Pro Val Leu Asp Ser Asp Gly Ser Phe Phe Leu Tyr
            195                 200                 205

Ser Lys Leu Thr Val Asp Lys Ser Arg Trp Gln Gln Gly Asn Val Phe
        210                 215                 220

Ser Cys Ser Val Met His Glu Ala Leu His Asn His Tyr Thr Gln Lys
225                 230                 235                 240

Ser Leu Ser Leu Ser Pro Gly Lys
            245

<210> SEQ ID NO 113
<211> LENGTH: 248
<212> TYPE: PRT
<213> ORGANISM: Artificial Sequence
<220> FEATURE:
<223> OTHER INFORMATION: TALL-1 inhibitory peptibody TALL-1-8-4-a

<400> SEQUENCE: 113

Met Val Pro Phe Cys Asp Leu Leu Thr Lys His Cys Phe Glu Ala Gly
1               5                   10                  15

Gly Gly Gly Gly Val Asp Lys Thr His Thr Cys Pro Pro Cys Pro Ala
            20                  25                  30

Pro Glu Leu Leu Gly Gly Pro Ser Val Phe Leu Phe Pro Pro Lys Pro
        35                  40                  45

Lys Asp Thr Leu Met Ile Ser Arg Thr Pro Glu Val Thr Cys Val Val
    50                  55                  60

Val Asp Val Ser His Glu Asp Pro Glu Val Lys Phe Asn Trp Tyr Val
65                  70                  75                  80

Asp Gly Val Glu Val His Asn Ala Lys Thr Lys Pro Arg Glu Glu Gln
                85                  90                  95

Tyr Asn Ser Thr Tyr Arg Val Val Ser Val Leu Thr Val Leu His Gln
            100                 105                 110

Asp Trp Leu Asn Gly Lys Glu Tyr Lys Cys Lys Val Ser Asn Lys Ala
        115                 120                 125

Leu Pro Ala Pro Ile Glu Lys Thr Ile Ser Lys Ala Lys Gly Gln Pro
    130                 135                 140

Arg Glu Pro Gln Val Tyr Thr Leu Pro Pro Ser Arg Asp Glu Leu Thr
145                 150                 155                 160

Lys Asn Gln Val Ser Leu Thr Cys Leu Val Lys Gly Phe Tyr Pro Ser
                165                 170                 175

Asp Ile Ala Val Glu Trp Glu Ser Asn Gly Gln Pro Glu Asn Asn Tyr
            180                 185                 190

Lys Thr Thr Pro Pro Val Leu Asp Ser Asp Gly Ser Phe Phe Leu Tyr
        195                 200                 205

Ser Lys Leu Thr Val Asp Lys Ser Arg Trp Gln Gln Gly Asn Val Phe
    210                 215                 220

Ser Cys Ser Val Met His Glu Ala Leu His Asn His Tyr Thr Gln Lys
225                 230                 235                 240

Ser Leu Ser Leu Ser Pro Gly Lys
            245

<210> SEQ ID NO 114
<211> LENGTH: 252
<212> TYPE: PRT
<213> ORGANISM: Artificial Sequence
```

-continued

<220> FEATURE:
<223> OTHER INFORMATION: TALL-1 inhibitory peptibody TALL-1-12-4-a

<400> SEQUENCE: 114

Met Gly Ser Arg Cys Lys Tyr Lys Trp Asp Val Leu Thr Lys Gln Cys
1               5                   10                  15

Phe His His Gly Gly Gly Gly Val Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250

<210> SEQ ID NO 115
<211> LENGTH: 252
<212> TYPE: PRT
<213> ORGANISM: Artificial Sequence
<220> FEATURE:
<223> OTHER INFORMATION: TALL-1 inhibitory peptibody TALL-1-12-3-a

<400> SEQUENCE: 115

Met Leu Pro Gly Cys Lys Trp Asp Leu Leu Ile Lys Gln Trp Val Cys
1               5                   10                  15

Asp Pro Leu Gly Gly Gly Gly Val Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
                100                 105                 110

Val Leu His Gln Asp Trp Leu Asn Gly Lys Glu Tyr Lys Cys Lys Val
            115                 120                 125

Ser Asn Lys Ala Leu Pro Ala Pro Ile Glu Lys Thr Ile Ser Lys Ala
        130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250

<210> SEQ ID NO 116
<211> LENGTH: 252
<212> TYPE: PRT
<213> ORGANISM: Artificial Sequence
<220> FEATURE:
<223> OTHER INFORMATION: TALL-1 inhibitory peptibody TALL-1-12-5-a

<400> SEQUENCE: 116

Met Ser Ala Asp Cys Tyr Phe Asp Ile Leu Thr Lys Ser Asp Val Cys
1               5                   10                  15

Thr Ser Ser Gly Gly Gly Gly Val Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
                100                 105                 110

Val Leu His Gln Asp Trp Leu Asn Gly Lys Glu Tyr Lys Cys Lys Val
            115                 120                 125

Ser Asn Lys Ala Leu Pro Ala Pro Ile Glu Lys Thr Ile Ser Lys Ala
        130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

```
Phe Phe Leu Tyr Ser Lys Leu Thr Val Asp Lys Ser Arg Trp Gln Gln
            210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250

<210> SEQ ID NO 117
<211> LENGTH: 252
<212> TYPE: PRT
<213> ORGANISM: Artificial Sequence
<220> FEATURE:
<223> OTHER INFORMATION: TALL-1 inhibitory peptibody TALL-1-12-8-a

<400> SEQUENCE: 117

Met Ser Asp Asp Cys Met Tyr Asp Gln Leu Thr Arg Met Phe Ile Cys
1               5                   10                  15

Ser Asn Leu Gly Gly Gly Gly Val Asp Lys Thr His Thr Cys Pro
            20                  25                  30

Pro Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250

<210> SEQ ID NO 118
<211> LENGTH: 252
<212> TYPE: PRT
<213> ORGANISM: Artificial Sequence
<220> FEATURE:
<223> OTHER INFORMATION: TALL-1 inhibitory peptibody TALL-1-12-9-a

<400> SEQUENCE: 118

Met Asp Leu Asn Cys Lys Tyr Asp Glu Leu Thr Tyr Lys Glu Trp Cys
1               5                   10                  15
```

```
Gln Phe Asn Gly Gly Gly Gly Val Asp Lys Thr His Thr Cys Pro
             20                  25                  30

Pro Cys Pro Ala Pro Glu Leu Leu Gly Gly Pro Ser Val Phe Leu Phe
         35                  40                  45

Pro Pro Lys Pro Lys Asp Thr Leu Met Ile Ser Arg Thr Pro Glu Val
 50                  55                  60

Thr Cys Val Val Val Asp Val Ser His Glu Asp Pro Glu Val Lys Phe
 65                  70                  75                  80

Asn Trp Tyr Val Asp Gly Val Glu Val His Asn Ala Lys Thr Lys Pro
                 85                  90                  95

Arg Glu Glu Gln Tyr Asn Ser Thr Tyr Arg Val Val Ser Val Leu Thr
             100                 105                 110

Val Leu His Gln Asp Trp Leu Asn Gly Lys Glu Tyr Lys Cys Lys Val
         115                 120                 125

Ser Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                 165                 170                 175

Phe Tyr Pro Ser Asp Ile Ala Val Glu Trp Glu Ser Asn Gly Gln Pro
             180                 185                 190

Glu Asn Asn Tyr Lys Thr Thr Pro Pro Val Leu Asp Ser Asp Gly Ser
         195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                 245                 250

<210> SEQ ID NO 119
<211> LENGTH: 252
<212> TYPE: PRT
<213> ORGANISM: Artificial Sequence
<220> FEATURE:
<223> OTHER INFORMATION: TALL-1 inhibitory peptibody TALL-1-12-10-a

<400> SEQUENCE: 119

Met Phe His Asp Cys Lys Tyr Asp Leu Leu Thr Arg Gln Met Val Cys
1               5                   10                  15

His Gly Leu Gly Gly Gly Gly Val Asp Lys Thr His Thr Cys Pro
             20                  25                  30

Pro Cys Pro Ala Pro Glu Leu Leu Gly Gly Pro Ser Val Phe Leu Phe
         35                  40                  45

Pro Pro Lys Pro Lys Asp Thr Leu Met Ile Ser Arg Thr Pro Glu Val
 50                  55                  60

Thr Cys Val Val Val Asp Val Ser His Glu Asp Pro Glu Val Lys Phe
 65                  70                  75                  80

Asn Trp Tyr Val Asp Gly Val Glu Val His Asn Ala Lys Thr Lys Pro
                 85                  90                  95

Arg Glu Glu Gln Tyr Asn Ser Thr Tyr Arg Val Val Ser Val Leu Thr
             100                 105                 110

Val Leu His Gln Asp Trp Leu Asn Gly Lys Glu Tyr Lys Cys Lys Val
         115                 120                 125

Ser Asn Lys Ala Leu Pro Ala Pro Ile Glu Lys Thr Ile Ser Lys Ala
```

```
                130                 135                 140
Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
                195                 200                 205

Phe Phe Leu Tyr Ser Lys Leu Thr Val Asp Lys Ser Arg Trp Gln Gln
            210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250

<210> SEQ ID NO 120
<211> LENGTH: 252
<212> TYPE: PRT
<213> ORGANISM: Artificial Sequence
<220> FEATURE:
<223> OTHER INFORMATION: TALL-1 inhibitory peptibody TALL-1-12-11-a

<400> SEQUENCE: 120

Met Arg Asn His Cys Phe Trp Asp His Leu Leu Lys Gln Asp Ile Cys
1               5                   10                  15

Pro Ser Pro Gly Gly Gly Gly Val Asp Lys Thr His Thr Cys Pro
            20                  25                  30

Pro Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
        50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
                195                 200                 205

Phe Phe Leu Tyr Ser Lys Leu Thr Val Asp Lys Ser Arg Trp Gln Gln
            210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250
```

<210> SEQ ID NO 121
<211> LENGTH: 252
<212> TYPE: PRT
<213> ORGANISM: Artificial Sequence
<220> FEATURE:
<223> OTHER INFORMATION: TALL-1 inhibitory peptibody TALL-1-12-14-a

<400> SEQUENCE: 121

```
Met Ala Asn Gln Cys Trp Trp Asp Ser Leu Thr Lys Lys Asn Val Cys
1               5                   10                  15

Glu Phe Phe Gly Gly Gly Gly Val Asp Lys Thr His Thr Cys Pro
            20                  25                  30

Pro Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
        50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250
```

<210> SEQ ID NO 122
<211> LENGTH: 252
<212> TYPE: PRT
<213> ORGANISM: Artificial Sequence
<220> FEATURE:
<223> OTHER INFORMATION: TALL-1 inhibitory peptibody consensus sequence

<400> SEQUENCE: 122

```
Met Phe His Asp Cys Lys Trp Asp Leu Leu Thr Lys Gln Trp Val Cys
1               5                   10                  15

His Gly Leu Gly Gly Gly Gly Val Asp Lys Thr His Thr Cys Pro
            20                  25                  30

Pro Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
        50                  55                  60
```

```
Thr Cys Val Val Val Asp Val Ser His Glu Asp Pro Glu Val Lys Phe
 65                  70                  75                  80

Asn Trp Tyr Val Asp Gly Val Glu Val His Asn Ala Lys Thr Lys Pro
                 85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250

<210> SEQ ID NO 123
<211> LENGTH: 293
<212> TYPE: PRT
<213> ORGANISM: Artificial Sequence
<220> FEATURE:
<223> OTHER INFORMATION: TALL-1 inhibitory peptibody 12-3 tandem dimer

<400> SEQUENCE: 123

Met Leu Pro Gly Cys Lys Trp Asp Leu Leu Ile Lys Gln Trp Val Cys
1               5                   10                  15

Asp Pro Leu Gly Ser Gly Ser Ala Thr Gly Gly Ser Gly Ser Thr Ala
                20                  25                  30

Ser Ser Gly Ser Gly Ser Ala Thr His Met Leu Pro Gly Cys Lys Trp
            35                  40                  45

Asp Leu Leu Ile Lys Gln Trp Val Cys Asp Pro Leu Gly Gly Gly Gly
        50                  55                  60

Gly Val Asp Lys Thr His Thr Cys Pro Pro Cys Pro Ala Pro Glu Leu
65                  70                  75                  80

Leu Gly Gly Pro Ser Val Phe Leu Phe Pro Pro Lys Pro Lys Asp Thr
                85                  90                  95

Leu Met Ile Ser Arg Thr Pro Glu Val Thr Cys Val Val Val Asp Val
            100                 105                 110

Ser His Glu Asp Pro Glu Val Lys Phe Asn Trp Tyr Val Asp Gly Val
        115                 120                 125

Glu Val His Asn Ala Lys Thr Lys Pro Arg Glu Glu Gln Tyr Asn Ser
    130                 135                 140

Thr Tyr Arg Val Val Ser Val Leu Thr Val Leu His Gln Asp Trp Leu
145                 150                 155                 160

Asn Gly Lys Glu Tyr Lys Cys Lys Val Ser Asn Lys Ala Leu Pro Ala
                165                 170                 175
```

```
Pro Ile Glu Lys Thr Ile Ser Lys Ala Lys Gly Gln Pro Arg Glu Pro
            180                 185                 190

Gln Val Tyr Thr Leu Pro Pro Ser Arg Asp Glu Leu Thr Lys Asn Gln
            195                 200                 205

Val Ser Leu Thr Cys Leu Val Lys Gly Phe Tyr Pro Ser Asp Ile Ala
    210                 215                 220

Val Glu Trp Glu Ser Asn Gly Gln Pro Glu Asn Asn Tyr Lys Thr Thr
225                 230                 235                 240

Pro Pro Val Leu Asp Ser Asp Gly Ser Phe Phe Leu Tyr Ser Lys Leu
                245                 250                 255

Thr Val Asp Lys Ser Arg Trp Gln Gln Gly Asn Val Phe Ser Cys Ser
            260                 265                 270

Val Met His Glu Ala Leu His Asn His Tyr Thr Gln Lys Ser Leu Ser
        275                 280                 285

Leu Ser Pro Gly Lys
        290

<210> SEQ ID NO 124
<211> LENGTH: 293
<212> TYPE: PRT
<213> ORGANISM: Artificial Sequence
<220> FEATURE:
<223> OTHER INFORMATION: TALL-1 inhibitory peptibody consensus tandem
      dimer

<400> SEQUENCE: 124

Met Phe His Asp Cys Lys Trp Asp Leu Leu Thr Lys Gln Trp Val Cys
1               5                   10                  15

His Gly Leu Gly Ser Gly Ser Ala Thr Gly Gly Ser Gly Ser Thr Ala
            20                  25                  30

Ser Ser Gly Ser Gly Ser Ala Thr His Met Phe His Asp Cys Lys Trp
        35                  40                  45

Asp Leu Leu Thr Lys Gln Trp Val Cys His Gly Leu Gly Gly Gly Gly
    50                  55                  60

Gly Val Asp Lys Thr His Thr Cys Pro Pro Cys Pro Ala Pro Glu Leu
65                  70                  75                  80

Leu Gly Gly Pro Ser Val Phe Leu Phe Pro Pro Lys Pro Lys Asp Thr
                85                  90                  95

Leu Met Ile Ser Arg Thr Pro Glu Val Thr Cys Val Val Val Asp Val
            100                 105                 110

Ser His Glu Asp Pro Glu Val Lys Phe Asn Trp Tyr Val Asp Gly Val
        115                 120                 125

Glu Val His Asn Ala Lys Thr Lys Pro Arg Glu Glu Gln Tyr Asn Ser
    130                 135                 140

Thr Tyr Arg Val Val Ser Val Leu Thr Val Leu His Gln Asp Trp Leu
145                 150                 155                 160

Asn Gly Lys Glu Tyr Lys Cys Lys Val Ser Asn Lys Ala Leu Pro Ala
                165                 170                 175

Pro Ile Glu Lys Thr Ile Ser Lys Ala Lys Gly Gln Pro Arg Glu Pro
            180                 185                 190

Gln Val Tyr Thr Leu Pro Pro Ser Arg Asp Glu Leu Thr Lys Asn Gln
        195                 200                 205

Val Ser Leu Thr Cys Leu Val Lys Gly Phe Tyr Pro Ser Asp Ile Ala
    210                 215                 220

Val Glu Trp Glu Ser Asn Gly Gln Pro Glu Asn Asn Tyr Lys Thr Thr
225                 230                 235                 240
```

```
Pro Pro Val Leu Asp Ser Asp Gly Ser Phe Phe Leu Tyr Ser Lys Leu
            245                 250                 255

Thr Val Asp Lys Ser Arg Trp Gln Gln Gly Asn Val Phe Ser Cys Ser
            260                 265                 270

Val Met His Glu Ala Leu His Asn His Tyr Thr Gln Lys Ser Leu Ser
            275                 280                 285

Leu Ser Pro Gly Lys
        290

<210> SEQ ID NO 125
<211> LENGTH: 14
<212> TYPE: PRT
<213> ORGANISM: Artificial Sequence
<220> FEATURE:
<223> OTHER INFORMATION: Modulator of TALL-1
<220> FEATURE:
<221> NAME/KEY: MISC_FEATURE
<222> LOCATION: (1)..(1)
<223> OTHER INFORMATION: Absent or amino acid residue (one of residues
      1, 2, or 3 preferably Cys when one of residues 12, 13, or 14 is
      Cys, and only one of residues 1, 2, or 3 may be Cys)
<220> FEATURE:
<221> NAME/KEY: MISC_FEATURE
<222> LOCATION: (2)..(2)
<223> OTHER INFORMATION: Absent or amino acid residue (one of residues
      1, 2, or 3 preferably Cys when one of residues 12, 13, or 14 is
      Cys, and only one of residues 1, 2, or 3 may be Cys)
<220> FEATURE:
<221> NAME/KEY: MISC_FEATURE
<222> LOCATION: (3)..(3)
<223> OTHER INFORMATION: Absent or amino acid residue (one of residues
      1, 2, or 3 preferably Cys when one of residues 12, 13, or 14 is
      Cys, and only one of residues 1, 2, or 3 may be Cys)
<220> FEATURE:
<221> NAME/KEY: MISC_FEATURE
<222> LOCATION: (7)..(7)
<223> OTHER INFORMATION: Amino acid residue (Leu preferred)
<220> FEATURE:
<221> NAME/KEY: MISC_FEATURE
<222> LOCATION: (9)..(9)
<223> OTHER INFORMATION: Thr or Ile (Thr preferred)
<220> FEATURE:
<221> NAME/KEY: MISC_FEATURE
<222> LOCATION: (12)..(12)
<223> OTHER INFORMATION: Cys, neutral hydrophobic residue, or basic
      residue (Trp, Cys, or Arg preferred, and only one of residues 12,
      13, or 14 may be Cys)
<220> FEATURE:
<221> NAME/KEY: MISC_FEATURE
<222> LOCATION: (13)..(13)
<223> OTHER INFORMATION: Cys, neutral hydrophobic residue, or absent
      (Val preferred, and only one of residues 12, 13, or 14 may be
      Cys))
<220> FEATURE:
<221> NAME/KEY: MISC_FEATURE
<222> LOCATION: (14)..(14)
<223> OTHER INFORMATION: Absent or amino acid residue (only one of
      residues 12, 13, or 14 may be Cys)

<400> SEQUENCE: 125

Xaa Xaa Xaa Lys Trp Asp Xaa Leu Xaa Lys Gln Xaa Xaa Xaa
1               5                   10

<210> SEQ ID NO 126
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 126

Tyr Lys Gly Arg Gln Met Trp Asp Ile Leu Thr Arg Ser Trp Val Val
1               5                   10                  15
```

-continued

Ser Leu

<210> SEQ ID NO 127
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 127

```
Gln Asp Val Gly Leu Trp Trp Asp Ile Leu Thr Arg Ala Trp Met Pro
1               5                   10                  15

Asn Ile
```

<210> SEQ ID NO 128
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 128

```
Gln Asn Ala Gln Arg Val Trp Asp Leu Leu Ile Arg Thr Trp Val Tyr
1               5                   10                  15

Pro Gln
```

<210> SEQ ID NO 129
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 129

Gly Trp Asn Glu Ala Trp Trp Asp Glu Leu Thr Lys Ile Trp Val Leu
1 5 10 15

Glu Gln

<210> SEQ ID NO 130
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 130

Arg Ile Thr Cys Asp Thr Trp Asp Ser Leu Ile Lys Lys Cys Val Pro
1 5 10 15

Gln Ser

<210> SEQ ID NO 131
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 131

Gly Ala Ile Met Gln Phe Trp Asp Ser Leu Thr Lys Thr Trp Leu Arg
1 5 10 15

Gln Ser

<210> SEQ ID NO 132

<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 132

Trp Leu His Ser Gly Trp Trp Asp Pro Leu Thr Lys His Trp Leu Gln
1 5 10 15

Lys Val

<210> SEQ ID NO 133
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 133

Ser Glu Trp Phe Phe Trp Phe Asp Pro Leu Thr Arg Ala Gln Leu Lys
1 5 10 15

Phe Arg

<210> SEQ ID NO 134
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 134

Gly Val Trp Phe Trp Trp Phe Asp Pro Leu Thr Lys Gln Trp Thr Gln
1 5 10 15

Ala Gly

<210> SEQ ID NO 135
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 135

Met Gln Cys Lys Gly Tyr Tyr Asp Ile Leu Thr Lys Trp Cys Val Thr
1 5 10 15

Asn Gly

<210> SEQ ID NO 136
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 136

Leu Trp Ser Lys Glu Val Trp Asp Ile Leu Thr Lys Ser Trp Val Ser
1 5 10 15

Gln Ala

<210> SEQ ID NO 137
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 137

Lys Ala Ala Gly Trp Trp Phe Asp Trp Leu Thr Lys Val Trp Val Pro
1               5                   10                  15

Ala Pro

<210> SEQ ID NO 138
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 138

Ala Tyr Gln Thr Trp Phe Trp Asp Ser Leu Thr Arg Leu Trp Leu Ser
1               5                   10                  15

Thr Thr

<210> SEQ ID NO 139
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 139

Ser Gly Gln His Phe Trp Trp Asp Leu Leu Thr Arg Ser Trp Thr Pro
1               5                   10                  15

Ser Thr

<210> SEQ ID NO 140
<211> LENGTH: 18
<212> TYPE: PRT
<213> ORGANISM: Artificial Sequence
<220> FEATURE:
<223> OTHER INFORMATION -continued Gly Arg
<210> SEQ ID NO 143
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 143

Gly Gln Ala Ile Arg His Trp Asp Val Leu Thr Lys Gln Trp Val Asp
1               5                   10                  15

Ser Gln

<210> SEQ ID NO 144
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 144

Arg Gly Pro Cys Gly Ser Trp Asp Leu Leu Thr Lys His Cys Leu Asp
1               5                   10                  15

Ser Gln

<210> SEQ ID NO 145
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 145

Trp Gln Trp Lys Gln Gln Trp Asp Leu Leu Thr Lys Gln Met Val Trp
1               5                   10                  15

Val Gly

<210> SEQ ID NO 146
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 146

Pro Ile Thr Ile Cys Arg Lys Asp Leu Leu Thr Lys Gln Val Val Cys
1               5                   10                  15

Leu Asp

<210> SEQ ID NO 147
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 147

Lys Thr Cys Asn Gly Lys Trp Asp Leu Leu Thr Lys Gln Cys Leu Gln
1               5                   10                  15

Gln Ala

<210> SEQ ID NO 148

<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 148

Lys Cys Leu Lys Gly Lys Trp Asp Leu Leu Thr Lys Gln Cys Val Thr
1 5 10 15

Glu Val

<210> SEQ ID NO 149
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 149

Arg Cys Trp Asn Gly Lys Trp Asp Leu Leu Thr Lys Gln Cys Ile His
1 5 10 15

Pro Trp

<210> SEQ ID NO 150
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 150

Asn Arg Asp Met Arg Lys Trp Asp Pro Leu Ile Lys Gln Trp Ile Val
1 5 10 15

Arg Pro

<210> SEQ ID NO 151
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 151

Gln Ala Ala Ala Ala Thr Trp Asp Leu Leu Thr Lys Gln Trp Leu Val
1 5 10 15

Pro Pro

<210> SEQ ID NO 152
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 152

Pro Glu Gly Gly Pro Lys Trp Asp Pro Leu Thr Lys Gln Phe Leu Pro
1 5 10 15

Pro Val

<210> SEQ ID NO 153
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 153

Gln Thr Pro Gln Lys Lys Trp Asp Leu Leu Thr Lys Gln Trp Phe Thr
1 5 10 15

Arg Asn

<210> SEQ ID NO 154
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 154

Ile Gly Ser Pro Cys Lys Trp Asp Leu Leu Thr Lys Gln Met Ile Cys
1 5 10 15

Gln Thr

<210> SEQ ID NO 155
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 155

Cys Thr Ala Ala Gly Lys Trp Asp Leu Leu Thr Lys Gln Cys Ile Gln
1 5 10 15

Glu Lys

<210> SEQ ID NO 156
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 156

Val Ser Gln Cys Met Lys Trp Asp Leu Leu Thr Lys Gln Cys Leu Gln
1 5 10 15

Gly Trp

<210> SEQ ID NO 157
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 157

Val Trp Gly Thr Trp Lys Trp Asp Leu Leu Thr Lys Gln Tyr Leu Pro
1 5 10 15

Pro Gln

<210> SEQ ID NO 158
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 158

Gly Trp Trp Glu Met Lys Trp Asp Leu Leu Thr Lys Gln Trp Tyr Arg
1 5 10 15

Pro Gln

<210> SEQ ID NO 159
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 159

Thr Ala Gln Val Ser Lys Trp Asp Leu Leu Thr Lys Gln Trp Leu Pro
1               5                   10                  15

Leu Ala

<210> SEQ ID NO 160
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 160

Gln Leu Trp Gly Thr Lys Trp Asp Leu Leu Thr Lys Gln Tyr Ile Gln
1               5                   10                  15

Ile Met

<210> SEQ ID NO 161
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 161

Trp Ala Thr Ser Gln Lys Trp Asp Leu Leu Thr Lys Gln Trp Val Gln
1 5 10 15

Asn Met

<210> SEQ ID NO 162
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 162

Gln Arg Gln Cys Ala Lys Trp Asp Leu Leu Thr Lys Gln Cys Val Leu
1 5 10 15

Phe Tyr

<210> SEQ ID NO 163
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 163

Lys Thr Thr Asp Cys Lys Trp Asp Leu Leu Thr Lys Gln Arg Ile Cys
1 5 10 15

Gln Val

<210> SEQ ID NO 164

<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 164

Leu Leu Cys Gln Gly Lys Trp Asp Leu Leu Thr Lys Gln Cys Leu Lys
1 5 10 15

Leu Arg

<210> SEQ ID NO 165
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 165

Leu Met Trp Phe Trp Lys Trp Asp Leu Leu Thr Lys Gln Leu Val Pro
1 5 10 15

Thr Phe

<210> SEQ ID NO 166
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 166

Gln Thr Trp Ala Trp Lys Trp Asp Leu Leu Thr Lys Gln Trp Ile Gly
1 5 10 15

Pro Met

<210> SEQ ID NO 167
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 167

Asn Lys Glu Leu Leu Lys Trp Asp Leu Leu Thr Lys Gln Cys Arg Gly
1 5 10 15

Arg Ser

<210> SEQ ID NO 168
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 168

Gly Gln Lys Asp Leu Lys Trp Asp Leu Leu Thr Lys Gln Tyr Val Arg
1 5 10 15

Gln Ser

<210> SEQ ID NO 169
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 169

Pro Lys Pro Cys Gln Lys Trp Asp Leu Leu Thr Lys Gln Cys Leu Gly
1               5                   10                  15
Ser Val

<210> SEQ ID NO 170
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 170

Gly Gln Ile Gly Trp Lys Trp Asp Leu Leu Thr Lys Gln Trp Ile Gln
1               5                   10                  15
Thr Arg

<210> SEQ ID NO 171
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 171

Val Trp Leu Asp Trp Lys Trp Asp Leu Leu Thr Lys Gln Trp Ile His
1               5                   10                  15
Pro Gln

<210> SEQ ID NO 172
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 172

Gln Glu Trp Glu Tyr Lys Trp Asp Leu Leu Thr Lys Gln Trp Gly Trp
1               5                   10                  15
Leu Arg

<210> SEQ ID NO 173
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 173

His Trp Asp Ser Trp Lys Trp Asp Leu Leu Thr Lys Gln Trp Val Val
1               5                   10                  15
Gln Ala

<210> SEQ ID NO 174
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 174

Thr Arg Pro Leu Gln Lys Trp Asp Leu Leu Thr Lys Gln Trp Leu Arg
1               5                   10                  15

Val Gly

<210> SEQ ID NO 175
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 175

Ser Asp Gln Trp Gln Lys Trp Asp Leu Leu Thr Lys Gln Trp Phe Trp
1               5                   10                  15

Asp Val

<210> SEQ ID NO 176
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 176

Gln Gln Thr Phe Met Lys Trp Asp Leu Leu Thr Lys Gln Trp Ile Arg
1               5                   10                  15

Arg His

<210> SEQ ID NO 177
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 177

Gln Gly Glu Cys Arg Lys Trp Asp Leu Leu Thr Lys Gln Cys Phe Pro
1 5 10 15

Gly Gln

<210> SEQ ID NO 178
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 178

Gly Gln Met Gly Trp Arg Trp Asp Pro Leu Ile Lys Met Cys Leu Gly
1 5 10 15

Pro Ser

<210> SEQ ID NO 179
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 179

Gln Leu Asp Gly Cys Lys Trp Asp Leu Leu Thr Lys Gln Lys Val Cys
1 5 10 15

Ile Pro

<210> SEQ ID NO 180

<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 180

His Gly Tyr Trp Gln Lys Trp Asp Leu Leu Thr Lys Gln Trp Val Ser
1 5 10 15

Ser Glu

<210> SEQ ID NO 181
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 181

His Gln Gly Gln Cys Gly Trp Asp Leu Leu Thr Arg Ile Tyr Leu Pro
1 5 10 15

Cys His

<210> SEQ ID NO 182
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 182

Leu His Lys Ala Cys Lys Trp Asp Leu Leu Thr Lys Gln Cys Trp Pro
1 5 10 15

Met Gln

<210> SEQ ID NO 183
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 183

Gly Pro Pro Gly Ser Val Trp Asp Leu Leu Thr Lys Ile Trp Ile Gln
1 5 10 15

Thr Gly

<210> SEQ ID NO 184
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 184

Ile Thr Gln Asp Trp Arg Phe Asp Thr Leu Thr Arg Leu Trp Leu Pro
1 5 10 15

Leu Arg

<210> SEQ ID NO 185
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 185

Gln Gly Gly Phe Ala Ala Trp Asp Val Leu Thr Lys Met Trp Ile Thr
1               5                   10                  15

Val Pro

<210> SEQ ID NO 186
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 186

Gly His Gly Thr Pro Trp Trp Asp Ala Leu Thr Arg Ile Trp Ile Leu
1               5                   10                  15

Gly Val

<210> SEQ ID NO 187
<211> LENGTH: 18
<212> TYPE: PRT
<213> ORGANISM: Artificial Sequence
<220> FEATURE:
<223> OTHER INFORMATION: Preferred TALL-1 modulating domain

<400> SEQUENCE: 187

Val Trp Pro Trp Gln Lys Trp Asp Leu Leu Thr Lys Gln Phe Val Phe
1               5                   10                  15

Gln Asp

<210> SEQ ID NO 188
<211> LENGTH: 19
<212> TYPE: PRT
<213> ORGANISM: Artificial Sequence
<220> FEATURE:
<223> OTHER INFORMATION: Preferred TALL-1 modulating domain

<400> SEQUENCE: 188

Trp Gln Gln Trp Ser Trp Lys Trp Asp Leu Leu Thr Arg Gln Tyr Ile
1               5                   10                  15

Ser Ser Ser

<210> SEQ ID NO 189
<211> LENGTH: 882
<212> TYPE: DNA
<213> ORGANISM: Artificial Sequence
<220> FEATURE:
<223> OTHER INFORMATION: TALL-1 inhibitory peptibody 12-3 tandem dimer
<220> FEATURE:
<221> NAME/KEY: CDS
<222> LOCATION: (1)..(879)

<400> SEQUENCE: 189 atg ctt cca ggc tgc aag tgg gat ctt ctt att aag caa tgg gta tgc 48
Met Leu Pro Gly Cys Lys Trp Asp Leu Leu Ile Lys Gln Trp Val Cys
1 5 10 15 gat cca ctt gga tcc ggt tct gct act ggt ggt tcc ggc tcc acc gca 96
Asp Pro Leu Gly Ser Gly Ser Ala Thr Gly Gly Ser Gly Ser Thr Ala
20 25 30 agc tct ggt tca ggc agt gcg act cat atg ctg ccg ggt tgt aaa tgg 144
Ser Ser Gly Ser Gly Ser Ala Thr His Met Leu Pro Gly Cys Lys Trp
35 40 45 gac ctg ctg atc aaa cag tgg gtt tgt gac ccg ctg ggt gga ggc ggt 192
Asp Leu Leu Ile Lys Gln Trp Val Cys Asp Pro Leu Gly Gly Gly Gly

```
              50                  55                  60
ggg gtc gac aaa act cac aca tgt cca cct tgt cca gct ccg gaa ctc    240
Gly Val Asp Lys Thr His Thr Cys Pro Pro Cys Pro Ala Pro Glu Leu
 65                  70                  75                  80 ctg ggg gga ccg tca gtc ttc ctc ttc ccc cca aaa ccc aag gac acc    288
Leu Gly Gly Pro Ser Val Phe Leu Phe Pro Pro Lys Pro Lys Asp Thr
                 85                  90                  95 ctc atg atc tcc cgg acc cct gag gtc aca tgc gtg gtg gtg gac gtg    336
Leu Met Ile Ser Arg Thr Pro Glu Val Thr Cys Val Val Val Asp Val
            100                 105                 110 agc cac gaa gac cct gag gtc aag ttc aac tgg tac gtg gac ggc gtg    384
Ser His Glu Asp Pro Glu Val Lys Phe Asn Trp Tyr Val Asp Gly Val
        115                 120                 125 gag gtg cat aat gcc aag aca aag ccg cgg gag gag cag tac aac agc    432
Glu Val His Asn Ala Lys Thr Lys Pro Arg Glu Glu Gln Tyr Asn Ser
    130                 135                 140 acg tac cgt gtg gtc agc gtc ctc acc gtc ctg cac cag gac tgg ctg    480
Thr Tyr Arg Val Val Ser Val Leu Thr Val Leu His Gln Asp Trp Leu
145                 150                 155                 160 aat ggc aag gag tac aag tgc aag gtc tcc aac aaa gcc ctc cca gcc    528
Asn Gly Lys Glu Tyr Lys Cys Lys Val Ser Asn Lys Ala Leu Pro Ala
                165                 170                 175 ccc atc gag aaa acc atc tcc aaa gcc aaa ggg cag ccc cga gaa cca    576
Pro Ile Glu Lys Thr Ile Ser Lys Ala Lys Gly Gln Pro Arg Glu Pro
            180                 185                 190 cag gtg tac acc ctg ccc cca tcc cgg gat gag ctg acc aag aac cag    624
Gln Val Tyr Thr Leu Pro Pro Ser Arg Asp Glu Leu Thr Lys Asn Gln
        195                 200                 205 gtc agc ctg acc tgc ctg gtc aaa ggc ttc tat ccc agc gac atc gcc    672
Val Ser Leu Thr Cys Leu Val Lys Gly Phe Tyr Pro Ser Asp Ile Ala
    210                 215                 220 gtg gag tgg gag agc aat ggg cag ccg gag aac aac tac aag acc acg    720
Val Glu Trp Glu Ser Asn Gly Gln Pro Glu Asn Asn Tyr Lys Thr Thr
225                 230                 235                 240 cct ccc gtg ctg gac tcc gac ggc tcc ttc ttc ctc tac agc aag ctc    768
Pro Pro Val Leu Asp Ser Asp Gly Ser Phe Phe Leu Tyr Ser Lys Leu
                245                 250                 255 acc gtg gac aag agc agg tgg cag cag ggg aac gtc ttc tca tgc tcc    816
Thr Val Asp Lys Ser Arg Trp Gln Gln Gly Asn Val Phe Ser Cys Ser
            260                 265                 270 gtg atg cat gag gct ctg cac aac cac tac acg cag aag agc ctc tcc    864
Val Met His Glu Ala Leu His Asn His Tyr Thr Gln Lys Ser Leu Ser
        275                 280                 285 ctg tct ccg ggt aaa taa                                            882
Leu Ser Pro Gly Lys
    290

<210> SEQ ID NO 190
<211> LENGTH: 23
<212> TYPE: PRT
<213> ORGANISM: Artificial Sequence
<220> FEATURE:
<223> OTHER INFORMATION: Preferred linker sequence

<400> SEQUENCE: 190

Gly Ser Gly Ser Ala Thr Gly Gly Ser Gly Ser Thr Ala Ser Ser Gly
1               5                   10                  15

Ser Gly Ser Ala Thr Gly Met
            20

<210> SEQ ID NO 191
```

```
<211> LENGTH: 23
<212> TYPE: PRT
<213> ORGANISM: Artificial Sequence
<220> FEATURE:
<223> OTHER INFORMATION: Preferred linker sequence

<400> SEQUENCE: 191

Gly Ser Gly Ser Ala Thr Gly Gly Ser Gly Ser Thr Ala Ser Ser Gly
1               5                   10                  15

Ser Gly Ser Ala Thr Gly Ser
            20

<210> SEQ ID NO 192
<211> LENGTH: 46
<212> TYPE: PRT
<213> ORGANISM: Artificial Sequence
<220> FEATURE:
<223> OTHER INFORMATION: Preferred linker sequence

<400> SEQUENCE: 192

Gly Ser Gly Ser Ala Thr Gly Gly Ser Gly Ser Thr Ala Ser Ser Gly
1               5                   10                  15

Ser Gly Ser Ala Thr His Met Gly Ser Gly Ser Ala Thr Gly Gly Ser
            20                  25                  30

Gly Ser Thr Ala Ser Ser Gly Ser Gly Ser Ala Thr His Met
        35                  40                  45

<210> SEQ ID NO 193
<211> LENGTH: 23
<212> TYPE: PRT
<213> ORGANISM: Artificial Sequence
<220> FEATURE:
<223> OTHER INFORMATION: Preferred linker sequence
<220> FEATURE:
<221> NAME/KEY: MISC_FEATURE
<222> LOCATION: (22)..(22)
<223> OTHER INFORMATION: Basic or hydrophobic residue
<220> FEATURE:
<221> NAME/KEY: MISC_FEATURE
<222> LOCATION: (23)..(23)
<223> OTHER INFORMATION: Hydrophobic residue

<400> SEQUENCE: 193

Gly Ser Gly Ser Ala Thr Gly Gly Ser Gly Ser Thr Ala Ser Ser Gly
1               5                   10                  15

Ser Gly Ser Ala Thr Xaa Xaa
            20

<210> SEQ ID NO 194
<211> LENGTH: 46
<212> TYPE: PRT
<213> ORGANISM: Artificial Sequence
<220> FEATURE:
<223> OTHER INFORMATION: Preferred linker sequence
<220> FEATURE:
<221> NAME/KEY: MISC_FEATURE
<222> LOCATION: (22)..(22)
<223> OTHER INFORMATION: Basic or hydrophobic residue
<220> FEATURE:
<221> NAME/KEY: MISC_FEATURE
<222> LOCATION: (23)..(23)
<223> OTHER INFORMATION: Hydrophobic residue
<220> FEATURE:
<221> NAME/KEY: MISC_FEATURE
<222> LOCATION: (45)..(45)
<223> OTHER INFORMATION: Basic or hydrophobic residue
<220> FEATURE:
<221> NAME/KEY: MISC_FEATURE
<222> LOCATION: (46)..(46)
<223> OTHER INFORMATION: Hydrophobic residue
```

```
<400> SEQUENCE: 194

Gly Ser Gly Ser Ala Thr Gly Gly Ser Gly Ser Thr Ala Ser Ser Gly
1               5                   10                  15

Ser Gly Ser Ala Thr Xaa Xaa Gly Ser Gly Ser Ala Thr Gly Gly Ser
            20                  25                  30

Gly Ser Thr Ala Ser Ser Gly Ser Gly Ser Ala Thr Xaa Xaa
        35                  40                  45

<210> SEQ ID NO 195
<211> LENGTH: 38
<212> TYPE: PRT
<213> ORGANISM: Homo sapiens

<400> SEQUENCE: 195

Met Arg Arg Gly Pro Arg Ser Leu Arg Gly Arg Asp Ala Pro Val Pro
1               5                   10                  15

Thr Pro Cys Val Pro Thr Glu Cys Tyr Asp Leu Leu Val Arg Lys Cys
            20                  25                  30

Val Asp Cys Arg Leu Leu
        35

<210> SEQ ID NO 196
<211> LENGTH: 41
<212> TYPE: PRT
<213> ORGANISM: Homo sapiens

<400> SEQUENCE: 196

Thr Ile Cys Asn His Gln Ser Gln Arg Thr Cys Ala Ala Phe Cys Arg
1               5                   10                  15

Ser Leu Ser Cys Arg Lys Glu Gln Gly Lys Phe Tyr Asp His Leu Leu
            20                  25                  30

Arg Asp Cys Ile Ser Cys Ala Ser Ile
        35                  40

<210> SEQ ID NO 197
<211> LENGTH: 42
<212> TYPE: PRT
<213> ORGANISM: Homo sapiens

<400> SEQUENCE: 197

Phe Val Ser Pro Ser Gln Glu Ile Arg Gly Arg Phe Arg Arg Met Leu
1               5                   10                  15

Gln Met Ala Gly Gln Cys Ser Gln Asn Glu Tyr Phe Asp Ser Leu Leu
            20                  25                  30

His Ala Cys Ile Pro Cys Gln Leu Arg Cys
        35                  40
```

What is claimed is:

1. A TALL-1 binding composition of matter having the formula:

$$P^2\text{-}(L^2)\text{-}P^1\text{-}(L^1)\text{-}V^1$$

wherein:
 $P^1$ comprises the amino acid sequence of SEQ ID NO: 33;
 $P^2$ comprises the amino acid sequence of SEQ ID NO: 125; and
 $L^1$ and $L^2$ are peptide linkers; and
 $V^1$ is a vehicle
and multimers thereof.

2. The TALL-1 binding composition of claim 1, wherein $P^1\text{-}(L^1)\text{-}V^1$ comprises the amino acid sequence of SEQ ID NO: 44.

3. The TALL-1 binding composition of claim 2, wherein $L^1$ comprises a $Gly_5$ peptide linker.

4. The TALL-1 binding composition of claim 3, wherein $P^1\text{-}(L^1)$ comprises the amino acid sequence of SEQ ID NO: 12.

5. The TALL-1 binding composition of claim 3, wherein $V^1$ is an Fc domain.

6. The TALL-1 binding composition of claim 5, wherein $P^1\text{-}(L^1)\text{-}V^1$ comprises the amino acid sequence of SEQ ID NO: 115.

7. The TALL-1 binding composition of claim 1, wherein $L^2$ comprises an amino acid sequence selected from the group consisting of SEQ ID NO: 59 and SEQ ID NO: 193.

* * * * *